(12) United States Patent
Kim

(10) Patent No.: US 11,859,175 B2
(45) Date of Patent: Jan. 2, 2024

(54) CELL REPROGRAMMING METHOD USING PHYSICAL STIMULATION-MEDIATED ENVIRONMENTAL INFLUX

(71) Applicant: STEMON INC., Seongnam-si (KR)

(72) Inventor: Soon Hag Kim, Seongnam-si (KR)

(73) Assignee: STEMON INC., Seongnam-si (KR)

( * ) Notice: Subject to any disclaimer, the term of this patent is extended or adjusted under 35 U.S.C. 154(b) by 623 days.

(21) Appl. No.: 16/082,926

(22) PCT Filed: Aug. 9, 2016

(86) PCT No.: PCT/KR2016/008754
§ 371 (c)(1),
(2) Date: Dec. 26, 2018

(87) PCT Pub. No.: WO2017/155166
PCT Pub. Date: Sep. 14, 2017

(65) Prior Publication Data
US 2019/0119666 A1    Apr. 25, 2019

(30) Foreign Application Priority Data

Mar. 11, 2016  (KR) .................. 10-2016-0029611
Jun. 9, 2016   (KR) .................. 10-2016-0071852

(51) Int. Cl.
| | |
|---|---|
| *C12N 5/00* | (2006.01) |
| *C12N 13/00* | (2006.01) |
| *C12N 5/0797* | (2010.01) |
| *C12N 5/077* | (2010.01) |
| *C12N 5/071* | (2010.01) |

(52) U.S. Cl.
CPC ............ *C12N 13/00* (2013.01); *C12N 5/067* (2013.01); *C12N 5/0623* (2013.01); *C12N 5/0656* (2013.01); *C12N 5/0658* (2013.01); *C12N 2521/10* (2013.01); *C12N 2523/00* (2013.01); *C12N 2529/00* (2013.01)

(58) Field of Classification Search
CPC .... C12N 13/00; C12N 5/0623; C12N 5/0656; C12N 5/0658; C12N 5/067; C12N 2521/10; C12N 2523/00; C12N 2529/00; C12N 5/0696; C12N 5/0618; C12N 5/0653
See application file for complete search history.

(56) References Cited

U.S. PATENT DOCUMENTS

| 7,052,720 B1 | 5/2006 | Jones |
| 2015/0044751 A1 | 2/2015 | Chiou et al. |
| 2015/0110749 A1 | 4/2015 | Vacanti et al. |

FOREIGN PATENT DOCUMENTS

| JP | 2014-512821 A | 5/2014 | |
| JP | 2014-230521 A | 12/2014 | |
| JP | 2017-536853 A | 12/2017 | |
| JP | 2019-508069 A | 3/2019 | |
| KR | 10-2014-0031943 A | 3/2014 | |
| KR | 10-2015-0045935 A | 4/2015 | |
| WO | WO-2013163296 A1 * | 10/2013 | ............... A61P 7/06 |
| WO | 2015-143125 A1 | 9/2015 | |

OTHER PUBLICATIONS

Yong et al., Biotechnol. J. 9:1081-1087, 2014, including Supporting information. (Year: 2014).*
Luo et al., Nanoscale Research Letters (2015) 10:496 (Year: 2015).*
Hunter, Ultrasonics Sonochemistry. 15: 101-109, 2008. (Year: 2008).*
Huang et al., Cell Stem Cell, .14: 370-384, 2014, including Supplemental Experimental Procedures (Year: 2014).*
Simeonov et al., PLOS ONE, 9(6), e100134: 1-11, 2014.*
International Search Report for PCT/KR2016/008754 dated Dec. 9, 2016 from Korean Intellectual Property Office.
Uchugonova, Aisada et al., "Optical reprogramming of human cells in an ultrashort femtosecond laser microfluidic transfection platform", Journal of Biophotonics, (E-pub.) Nov. 5, 2015, vol. 9, No. 9, pp. 942-947.
Lv, Yonggang et al., "Effects of low-intensity pulsed ultrasound on cell viability, proliferation and neural differentiation of induced pluripotent stem cells-derived neural crest stem cells", Biotechnology Letters, (E-pub.) Sep. 28, 2013, vol. 35, No. 12, pp. 2201-2212.
J Ratajczak et al., "Embryonic stem cell-derived microvesicles reprogram hematopoietic progenitors: evidence for horizontal transfer of mRNA and protein delivery", Leukemia, Nature publishing Group UK, London, vol. 20, No. 5, May 1, 2006, pp. 847-856.
Peter J. Quesenberry et al, "Role of extracellular RNA-carrying vesicles in cell differentiation and reprogramming", Stem Cell Research & Therapy, vol. 6, No. 1, Sep. 3, 2015 (Sep. 3, 2015).
Guan-Qun Ju et al., "Microvesicles Derived from Human Umbilical Cord Mesenchymal Stem Cells Facilitate Tubular Epithelial Cell Dedifferentiation and Growth via Hepatocyte Growth Factor Induction", PLOS ONE, vol. 10, No. 3, Mar. 20, 2015 (Mar. 20, 2015), pp. 1-16.

(Continued)

*Primary Examiner* — Marcia S Noble
(74) *Attorney, Agent, or Firm* — Revolution IP, PLLC

(57) ABSTRACT

The present invention relates to a cell reprogramming method using a physical stimulation-mediated environmental influx, and more specifically, by subjecting differentiated or non-differentiated cells to physical stimulation which can promote an environmental influx, such as ultrasonic waves, laser or heat shock, without the introduction of a reprogramming-inducing factor or a chemical substance to the differentiated cells, the cells can be reprogrammed with just the imposition of an external environmental influx into pluripotent cells or arbitrary differentiated cells having a different expression type from the differentiated or non-differentiated cells, and as such an inducement has a simple and effective production process, the possibility of an autogenic cell therapy can be made greater.

4 Claims, 45 Drawing Sheets

Specification includes a Sequence Listing.

(56) References Cited

OTHER PUBLICATIONS

Malin Hedlund et al., "Thermal- and Oxidative Stress Causes Enhanced Release of NKG2D Ligand-Bearing Immunosuppressive Exosomes in LeukemiajLymphoma T and B Cell s", PLOS ONE, vol. 6, No. 2, Feb. 25, 2011 (Feb. 25, 2011), p. e16899.

Haruko Obokata et al., "Bidirectional developmental potential in reprogrammed cells with acquired pluripotency", Nature, vol. 505, No. 7485, Jan. 29, 2014 (Jan. 29, 2014), pp. 676-680.

Hitoshi Niwa, "Investigation of the cellular reprogramming phenomenon referred to as stimulus-triggered acquisition of pluripotency (STAP)", Scientific Reports, vol. 6, Jun. 13, 2016 (Jun. 13, 2016), p. 28003.

Konno Daijiro et al., "STAP derived from ES cells.", Nature Sep. 24, 2015, vol. 525, No. 7570, Sep. 24, 2015 (Sep. 24, 2015), pp. E4-E5.

Haruko Obokata et al., "Retraction: Stimulus-triggered fate conversion somatic cell into pluripotency", Nature, vol. 511, No. 7507, Jul. 2, 2014 (Jul. 2, 2014), pp. 112-112.

Y. Lee et al., "Exosomes and microvesicles: extracellular vesicles genetic information transfer and gene therapy", Human Molecular Genetics, vol. 21, No. R1, Oct. 15, 2012 (Oct. 15, 2012), R125-R134.

Yong Seung Lee et al., "Exosome-Mediated Ultra-Effective Direct Conversion of Human Fibroblasts into Neural Progenitor-like Cells", ACS Nano, vol. 12, No. 3, Feb. 20, 2018 (Feb. 2, 2018), 2531-2538.

* cited by examiner

HDF direct differentiation method

Method
Cell: Human dermal fibroblast (HDF)
Process:
 – Cell treatment:
 – Medium treatment:

a b a — Live photographing image in n/ENTER sphere proliferation process b — Cell ICC after live photographing

Hepatocyte direct differentiation

Cell: Human dermal fibroblasts (HDF), uterine cancer cells (HeLa),
 liver cancer cells (Hep3B)

Method
- Cell treatment: 1X10$^6$ cell, Ultrasonic wave 1 w/cm$^2$, 5 sec
- Medium treatment: 5 W/cm$^2$, 10 min
- Culture medium: Hepatocyte differentiation-inducing medium
  (using Laminin coating dish)

```
                             SEQUENCE LISTING

<160> NUMBER OF SEQ ID NOS: 128

<210> SEQ ID NO 1
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 1-P2X4-Forward

<400> SEQUENCE: 1
tctcaacagg caggtgcgta gctt                                              24

<210> SEQ ID NO 2
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table 1-P2X7-Forward

<400> SEQUENCE: 2
cagaaggcca agagcagcgg tt                                                22

<210> SEQ ID NO 3
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y1-Forward

<400> SEQUENCE: 3
cttggtgctg attctgggct g                                                 21

<210> SEQ ID NO 4
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y2-Forward

<400> SEQUENCE: 4
ccgctcgctg gacctcagct g                                                 21

<210> SEQ ID NO 5
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y11-Forward

<400> SEQUENCE: 5
gaggcctgca tcaagtgtct g                                                 21
```

```
<210> SEQ ID NO 6
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table2-Oc4(POU5F1)-Forward

<400> SEQUENCE: 6
gacaggggga ggggaggagc tagg                                          24

<210> SEQ ID NO 7
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table2-Sox2-Forward

<400> SEQUENCE: 7
gggaaatggg aggggtgcaa aagagg                                        26

<210> SEQ ID NO 8
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table2-Nanog-Forward

<400> SEQUENCE: 8
cagccccgat tcttccacca gtccc                                         25

<210> SEQ ID NO 9
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table2-Utf1-Forward

<400> SEQUENCE: 9
ccgtcgctga acaccgccct gctg                                          24

<210> SEQ ID NO 10
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table2-Lin28a-Forward

<400> SEQUENCE: 10
agcgcagatc aaaaggagac a                                             21

<210> SEQ ID NO 11
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table2-Rex1-Forward
```

```
<400> SEQUENCE: 11
cagatcctaa acagctcgca gaat                                              24

<210> SEQ ID NO 12
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table2-Fgf4-Forward

<400> SEQUENCE: 12
ctacaacgcc tacgagtcct aca                                               23

<210> SEQ ID NO 13
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table2-Foxd3-Forward

<400> SEQUENCE: 13
aagctggtcg agcaaactca                                                   20

<210> SEQ ID NO 14
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table2-Esg1-Forward

<400> SEQUENCE: 14
atatcccgcc gtgggtgaaa gttc                                              24

<210> SEQ ID NO 15
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table2-Tdgf1-Forward

<400> SEQUENCE: 15
ctgctgcctg aatgggggaa cctgc                                             25

<210> SEQ ID NO 16
<211> LENGTH: 28
<212> TYPE: DNA
<213> ORGANISM: Homo sapiens
<220> FEATURE:
<221> NAME/KEY: primer_bind
<222> LOCATION: (1)..(28)
<223> OTHER INFORMATION: Table2-cMyc-Forward

<400> SEQUENCE: 16
aatgaaaagg cccccaaggt agttatcc                                          28

<210> SEQ ID NO 17
<211> LENGTH: 20
<212> TYPE: DNA
<213> ORGANISM: Homo sapiens
```

```
<220> FEATURE:
<221> NAME/KEY: primer_bind
<222> LOCATION: (1)..(20)
<223> OTHER INFORMATION: Table2-Klf4-Forward

<400> SEQUENCE: 17
cccacatgaa gcgacttccc                                           20

<210> SEQ ID NO 18
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Oct4-Foward

<400> SEQUENCE: 18
ccaggttcaa tggattctcc                                           20

<210> SEQ ID NO 19
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Nanog-Foward

<400> SEQUENCE: 19
ttctctcctc ctccctctcc                                           20

<210> SEQ ID NO 20
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Tdgf1_1-Foward

<400> SEQUENCE: 20
gtgggtcctc ttcagtgcat                                           20

<210> SEQ ID NO 21
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Tdgf1_2-Foward

<400> SEQUENCE: 21
gaccctcgcc ttatcctttc                                           20

<210> SEQ ID NO 22
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Tdfg1_3-Foward

<400> SEQUENCE: 22
gcacagaggg tgtccatctt                                           20
```

<210> SEQ ID NO 23
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Afp-Foward

<400> SEQUENCE: 23
cagtccagca acaagccttt                                            20

<210> SEQ ID NO 24
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Gata4-Foward

<400> SEQUENCE: 24
taggatgcct gctggatttc                                            20

<210> SEQ ID NO 25
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table4-Acta2-Foward

<400> SEQUENCE: 25
ggagcacttg agaagcaaag a                                          21

<210> SEQ ID NO 26
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Msx1-Foward

<400> SEQUENCE: 26
gtagacgcgg tttgtggaac                                            20

<210> SEQ ID NO 27
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Pax6-Foward

<400> SEQUENCE: 27
gttgcagctg gtgtgttgac                                            20

<210> SEQ ID NO 28
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table4-Nestin-Foward

```
<400> SEQUENCE: 28
gggtcaagtg gactttcctg                                               20

<210> SEQ ID NO 29
<211> LENGTH: 20
<212> TYPE: DNA
<213> ORGANISM: Homo sapiens
<220> FEATURE:
<221> NAME/KEY: protein_bind
<222> LOCATION: (1)..(20)
<223> OTHER INFORMATION: Table5-Afp-Forward

<400> SEQUENCE: 29
agcagcttgg tggtggatga                                               20

<210> SEQ ID NO 30
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-Foxa2-Forward

<400> SEQUENCE: 30
ttcaggcccg gctaactctg                                               20

<210> SEQ ID NO 31
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table5-Gata6-Forward

<400> SEQUENCE: 31
tgtgcgttca tggagaagat ca                                            22

<210> SEQ ID NO 32
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table5-Nestin-Forward

<400> SEQUENCE: 32
gaaacagcca tagagggcaa a                                             21

<210> SEQ ID NO 33
<211> LENGTH: 28
<212> TYPE: DNA
<213> ORGANISM: Homo sapiens
<220> FEATURE:
<221> NAME/KEY: primer_bind
<222> LOCATION: (1)..(28)
<223> OTHER INFORMATION: Table5-Pax6-Forward

<400> SEQUENCE: 33
acccattatc cagatgtgtt tgcccgag                                      28

<210> SEQ ID NO 34
<211> LENGTH: 21
<212> TYPE: DNA
```

```
<213> ORGANISM: Homo sapiens
<220> FEATURE:
<221> NAME/KEY: primer_bind
<222> LOCATION: (1)..(21)
<223> OTHER INFORMATION: Table5-Acta2(a-SMA)-Forward

<400> SEQUENCE: 34
ctatgagggc tatgccttgc c                                          21

<210> SEQ ID NO 35
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table5-Brachury(T)-Forward

<400> SEQUENCE: 35
gccctctccc tccctccac gcacag                                      26

<210> SEQ ID NO 36
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table5-Msx1-Forward

<400> SEQUENCE: 36
cgagaggacc ccgtggatgc agag                                       24

<210> SEQ ID NO 37
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table5-Myl7-Forward

<400> SEQUENCE: 37
gggccccatc aacttcaccg tcttcc                                     26

<210> SEQ ID NO 38
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-Nkx2-5-Forward

<400> SEQUENCE: 38
ccaaggaccc tagagccgaa                                            20

<210> SEQ ID NO 39
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table5-TnTc-Forward

<400> SEQUENCE: 39
atgagcggga gaaggagcgg cagaac                                     26
```

<210> SEQ ID NO 40
<211> LENGTH: 30
<212> TYPE: DNA
<213> ORGANISM: Homo sapiens
<220> FEATURE:
<221> NAME/KEY: primer_bind
<222> LOCATION: (1)..(30)
<223> OTHER INFORMATION: Table5-Map2-Forward

<400> SEQUENCE: 40
caggtggcgg acgtgtgaaa attgagagtg                                     30

<210> SEQ ID NO 41
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table5-TuJ1-Forward

<400> SEQUENCE: 41
gagcggatca gcgtctacta caa                                            23

<210> SEQ ID NO 42
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table5-Gfap-Forward

<400> SEQUENCE: 42
cctctccctg gctcgaatg                                                 19

<210> SEQ ID NO 43
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-Vglut1-Forward

<400> SEQUENCE: 43
cgacgacagc cttttgtggt                                                20

<210> SEQ ID NO 44
<211> LENGTH: 18
<212> TYPE: DNA
<213> ORGANISM: Homo sapiens
<220> FEATURE:
<221> NAME/KEY: primer_bind
<222> LOCATION: (1)..(18)
<223> OTHER INFORMATION: Table5-Vmat2-Forward

<400> SEQUENCE: 44
ctttggagtt ggttttgc                                                  18

<210> SEQ ID NO 45
<211> LENGTH: 20
<212> TYPE: DNA
<213> ORGANISM: Homo sapiens
<220> FEATURE:
<221> NAME/KEY: primer_bind
<222> LOCATION: (1)..(20)

```
<223> OTHER INFORMATION: Table5-Pparc2-Forward

<400> SEQUENCE: 45
attgacccag aaagcgattc                                              20

<210> SEQ ID NO 46
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-C/ebpa-Forward

<400> SEQUENCE: 46
gcaaactcac cgctccaatg                                              20

<210> SEQ ID NO 47
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table5-aP2-Forward

<400> SEQUENCE: 47
aaccttagat gggggtgtcc tg                                           22

<210> SEQ ID NO 48
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-Fabp4-Forward

<400> SEQUENCE: 48
actgggccag gaatttgacg                                              20

<210> SEQ ID NO 49
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table5-Alb-Forward

<400> SEQUENCE: 49
agctgttatg gatgatttcg cag                                          23

<210> SEQ ID NO 50
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table5-Cyp3a4-Forward

<400> SEQUENCE: 50
gtgactttgc ccattgttta gaaag                                        25

<210> SEQ ID NO 51
<211> LENGTH: 23
```

```
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table5-Cyp3a7-Forward

<400> SEQUENCE: 51
gattctgtac gtgcattgtg ctc                                              23

<210> SEQ ID NO 52
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table5-Tat-Forward

<400> SEQUENCE: 52
ccacacccac actcagatcc t                                                21

<210> SEQ ID NO 53
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table5-A1AT-Forward

<400> SEQUENCE: 53
ggtcacagag gaggcaccc                                                   19

<210> SEQ ID NO 54
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table5-Sox7-Forward

<400> SEQUENCE: 54
tgcccacttc atgcaactcc                                                  20

<210> SEQ ID NO 55
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table5-beta-actin-Forward

<400> SEQUENCE: 55
catgtacgtt gctatccagg c                                                21

<210> SEQ ID NO 56
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table5-Gapdh-Forward

<400> SEQUENCE: 56
```
atggggaagg tgaaggtcg                    19

<210> SEQ ID NO 57
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table6-Oct4-Forward

<400> SEQUENCE: 57
gggtttttgg gattaagttc ttca              24

<210> SEQ ID NO 58
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table6-Sox2-Forward

<400> SEQUENCE: 58
caaaaatggc catgcaggtt                   20

<210> SEQ ID NO 59
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table6-Nanog-Forward

<400> SEQUENCE: 59
acaactggcc gaagaatagc a                 21

<210> SEQ ID NO 60
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table6-Sox1-Forward

<400> SEQUENCE: 60
tctgttaact caccgggacc                   20

<210> SEQ ID NO 61
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table6-Sox2-Forward

<400> SEQUENCE: 61
ggagtgcaat agggcggaat                   20

<210> SEQ ID NO 62
<211> LENGTH: 20
<212> TYPE: DNA
<213> ORGANISM: Homo sapiens
<220> FEATURE:
<221> NAME/KEY: primer_bind

```
<222> LOCATION: (1)..(20)
<223> OTHER INFORMATION: Table6-Pax6-Forward

<400> SEQUENCE: 62
gtccatcttt gcttgggaaa                                              20

<210> SEQ ID NO 63
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table6-Nestin-Forward

<400> SEQUENCE: 63
ctccagaaac tcaagcacc                                               19

<210> SEQ ID NO 64
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table6-Gapdh-Forward

<400> SEQUENCE: 64
atggggaagg tgaaggtcg                                               19

<210> SEQ ID NO 65
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table 1-P2X4-Bacward

<400> SEQUENCE: 65
gctcaacgtc ccgtgtatcg agg                                          23

<210> SEQ ID NO 66
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table 1-P2X7-Backward

<400> SEQUENCE: 66
ggacacgttg gtggtcttgt cgtca                                        25

<210> SEQ ID NO 67
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y1-Backward

<400> SEQUENCE: 67
gctcgggaga gtctccttct g                                            21

<210> SEQ ID NO 68
```

```
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y2-Backward

<400> SEQUENCE: 68
ctcactgctg cccaacacat c                                              21

<210> SEQ ID NO 69
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 1-P2Y11-Backward

<400> SEQUENCE: 69
acgttgagca cccgcatgat g                                              21

<210> SEQ ID NO 70
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 2-Oct4(POU5F1)-Backward

<400> SEQUENCE: 70
cttccctcca accagttgcc ccaaac                                         26

<210> SEQ ID NO 71
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 2-Sox2-Backward

<400> SEQUENCE: 71
ttgcgtgagt gtggatggga ttggtg                                         26

<210> SEQ ID NO 72
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table 2-Nanog-Backward

<400> SEQUENCE: 72
cggaagattc ccagtcgggt tcacc                                          25

<210> SEQ ID NO 73
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 2-Utf1-Backward

<400> SEQUENCE: 73
```

```
cgcgctgccc agaatgaagc ccac                                              24
```

<210> SEQ ID NO 74
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 2-Lin28a-Backward

<400> SEQUENCE: 74

```
cctctcgaaa gtaggttggc t                                                 21
```

<210> SEQ ID NO 75
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table 2-Rex1-Backward

<400> SEQUENCE: 75

```
gcgtacgcaa attaaagtcc aga                                               23
```

<210> SEQ ID NO 76
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 2-Fgf4-Backward

<400> SEQUENCE: 76

```
gttgcaccag aaaagtcaga gttg                                              24
```

<210> SEQ ID NO 77
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 2-Foxd3-Backward

<400> SEQUENCE: 77

```
ctcccatccc cacggtacta                                                   20
```

<210> SEQ ID NO 78
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 2-Esg1-Backward

<400> SEQUENCE: 78

```
actcagccat ggactggagc atcc                                              24
```

<210> SEQ ID NO 79
<211> LENGTH: 27
<212> TYPE: DNA
<213> ORGANISM: Homo sapiens
<220> FEATURE:

```
<221> NAME/KEY: primer_bind
<222> LOCATION: (1)..(27)
<223> OTHER INFORMATION: Table 2-Tdgf1-Backward

<400> SEQUENCE: 79
gccacgaggt gctcatccat cacaagg                                       27

<210> SEQ ID NO 80
<211> LENGTH: 25
<212> TYPE: DNA
<213> ORGANISM: Homo sapiens
<220> FEATURE:
<221> NAME/KEY: primer_bind
<222> LOCATION: (1)..(25)
<223> OTHER INFORMATION: Table 2-cMyc-Backward

<400> SEQUENCE: 80
gtcgtttccg caacaagtcc tcttc                                         25

<210> SEQ ID NO 81
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 2-Klf4-Backward

<400> SEQUENCE: 81
caggtccagg agatcgttga a                                             21

<210> SEQ ID NO 82
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Oct4-Backward

<400> SEQUENCE: 82
gtatccgacc agggttaggg                                               20

<210> SEQ ID NO 83
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Nanog-Backward

<400> SEQUENCE: 83
ctcccaaaat gctgggatta                                               20

<210> SEQ ID NO 84
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Tdgf1_1-Backward

<400> SEQUENCE: 84
gctgctggag aggtgcttag                                               20
```

-continued

```
<210> SEQ ID NO 85
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Tdgf1_2-Backward

<400> SEQUENCE: 85
cactgcccta ctgcttggtt                                               20

<210> SEQ ID NO 86
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Tdgf1_3-Backward

<400> SEQUENCE: 86
ctgcccctct cactcatctc                                               20

<210> SEQ ID NO 87
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Afp-Backward

<400> SEQUENCE: 87
actggagtca ctgggaggaa                                               20

<210> SEQ ID NO 88
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Gata4-Backward

<400> SEQUENCE: 88
cattcattcg ccctctcttc                                               20

<210> SEQ ID NO 89
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Acta2-Backward

<400> SEQUENCE: 89
ctcaggaaag cctccctctt                                               20

<210> SEQ ID NO 90
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Msx1-Backward
```

```
<400> SEQUENCE: 90
ttggggctct gttttttaacg                                              20

<210> SEQ ID NO 91
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Pax6-Backward

<400> SEQUENCE: 91
gcattgttgt gaatgctgct                                               20

<210> SEQ ID NO 92
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 4-Nestin-Backward

<400> SEQUENCE: 92
caccctcctt gtcactcctc                                               20

<210> SEQ ID NO 93
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 5-Afp-Backward

<400> SEQUENCE: 93
cctgagcttg gcacagatcc                                               20

<210> SEQ ID NO 94
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 5-Foxa2-Backward

<400> SEQUENCE: 94
ccttgcgtct ctgcaacacc                                               20

<210> SEQ ID NO 95
<211> LENGTH: 27
<212> TYPE: DNA
<213> ORGANISM: Homo sapiens
<220> FEATURE:
<221> NAME/KEY: primer_bind
<222> LOCATION: (1)..(27)
<223> OTHER INFORMATION: Table 5-Gata6-Backward

<400> SEQUENCE: 95
tttgataaga gacctcatga accgact                                       27

<210> SEQ ID NO 96
<211> LENGTH: 23
<212> TYPE: DNA
<213> ORGANISM: Homo sapiens
```

```
<220> FEATURE:
<221> NAME/KEY: primer_bind
<222> LOCATION: (1)..(23)
<223> OTHER INFORMATION: Table 5-Nestin-Backward

<400> SEQUENCE: 96
tggttttcca gagtcttcag tga                                            23

<210> SEQ ID NO 97
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 5-Pax6-Backward

<400> SEQUENCE: 97
atggtgaagc tgggcatagg cggcag                                         26

<210> SEQ ID NO 98
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table 5-Acta2(a-SMA)-Backward

<400> SEQUENCE: 98
gctcagcagt agtaacgaag ga                                             22

<210> SEQ ID NO 99
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 5-Brachyury(T)-Backward

<400> SEQUENCE: 99
cggcgccgtt gctcacagac cacagg                                         26

<210> SEQ ID NO 100
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 5-Msx1-Backward

<400> SEQUENCE: 100
ggcggccatc ttcagcttct ccag                                           24

<210> SEQ ID NO 101
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 5-My17-Backward

<400> SEQUENCE: 101
tgtagtcgat gttccccgcc aggtcc                                         26
```

```
<210> SEQ ID NO 102
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 5-Nkx2-5-Backward

<400> SEQUENCE: 102
ataggcgggg taggcgttat                                                 20

<210> SEQ ID NO 103
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 5-TnTc-Backward

<400> SEQUENCE: 103
tcaatggcca gcaccttcct cctctc                                          26

<210> SEQ ID NO 104
<211> LENGTH: 26
<212> TYPE: DNA
<213> ORGANISM: Homo sapiens
<220> FEATURE:
<221> NAME/KEY: primer_bind
<222> LOCATION: (1)..(26)
<223> OTHER INFORMATION: Table 5-Map2-Backward

<400> SEQUENCE: 104
cacgctggat ctgcctgggg actgtg                                          26

<210> SEQ ID NO 105
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table 5-TuJ1-Backward

<400> SEQUENCE: 105
gatactcctc acgcaccttg ct                                              22

<210> SEQ ID NO 106
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table 5-Gfap-Backward

<400> SEQUENCE: 106
ggaagcgaac cttctcgatg ta                                              22

<210> SEQ ID NO 107
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 5-Vglut1-Backward
```

<400> SEQUENCE: 107
gccgagacgt agaaaacaga g                                              21

<210> SEQ ID NO 108
<211> LENGTH: 18
<212> TYPE: DNA
<213> ORGANISM: Homo sapiens
<220> FEATURE:
<221> NAME/KEY: primer_bind
<222> LOCATION: (1)..(18)
<223> OTHER INFORMATION: Table 5-Vmat2-Backward

<400> SEQUENCE: 108
gcagttgtgg tccatgag                                                  18

<210> SEQ ID NO 109
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 5-Pparc2-Backward

<400> SEQUENCE: 109
caaaggagtg ggagtggtct                                                20

<210> SEQ ID NO 110
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 5-C/ebpa-Backward

<400> SEQUENCE: 110
ttaggttcca agccccaagt c                                              21

<210> SEQ ID NO 111
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 5-aP2-Backward

<400> SEQUENCE: 111
tcgtggaagt gacgcctttc                                                20

<210> SEQ ID NO 112
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table 5-Fabp4-Backward

<400> SEQUENCE: 112
ctcgtggaag tgacgcctt                                                 19

<210> SEQ ID NO 113
<211> LENGTH: 19
<212> TYPE: DNA

<213> ORGANISM: Homo sapiens
<220> FEATURE:
<221> NAME/KEY: primer_bind
<222> LOCATION: (1)..(19)
<223> OTHER INFORMATION: Table 5-Alb-Backward

<400> SEQUENCE: 113
cctcggcaaa gcaggtctc                                                    19

<210> SEQ ID NO 114
<211> LENGTH: 18
<212> TYPE: DNA
<213> ORGANISM: Homo sapiens
<220> FEATURE:
<221> NAME/KEY: primer_bind
<222> LOCATION: (1)..(18)
<223> OTHER INFORMATION: Table 5-Cyp3a4-Backward

<400> SEQUENCE: 114
caggcgtgag ccactgtg                                                     18

<210> SEQ ID NO 115
<211> LENGTH: 29
<212> TYPE: DNA
<213> ORGANISM: Homo sapiens
<220> FEATURE:
<221> NAME/KEY: primer_bind
<222> LOCATION: (1)..(29)
<223> OTHER INFORMATION: Table 5-Cyp3a7-Backward

<400> SEQUENCE: 115
atttggtcat ctcctctata ttaccaagt                                         29

<210> SEQ ID NO 116
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 5-Tat-Backward

<400> SEQUENCE: 116
attagtgagt cactctagca gcgc                                              24

<210> SEQ ID NO 117
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 5-A1AT-Backward

<400> SEQUENCE: 117
agtccctttc tcgtcgatgg t                                                 21

<210> SEQ ID NO 118
<211> LENGTH: 22
<212> TYPE: DNA
<213> ORGANISM: Homo sapiens
<220> FEATURE:
<221> NAME/KEY: primer_bind
<222> LOCATION: (1)..(22)
<223> OTHER INFORMATION: Table 5-Sox7-Backward

<400> SEQUENCE: 118
aggtaccctg ggtctttggt ca                                                22

```
<210> SEQ ID NO 119
<211> LENGTH: 21
<212> TYPE: DNA
<213> ORGANISM: Homo sapiens
<220> FEATURE:
<221> NAME/KEY: primer_bind
<222> LOCATION: (1)..(21)
<223> OTHER INFORMATION: Table 5-beta-actin-Backward

<400> SEQUENCE: 119
ctccttaatg tcacgcacga t                                             21

<210> SEQ ID NO 120
<211> LENGTH: 23
<212> TYPE: DNA
<213> ORGANISM: Homo sapiens
<220> FEATURE:
<221> NAME/KEY: primer_bind
<222> LOCATION: (1)..(23)
<223> OTHER INFORMATION: Table 5-Gapdh-Backward

<400> SEQUENCE: 120
gggtcattga tggcaacaat atc                                           23

<210> SEQ ID NO 121
<211> LENGTH: 18
<212> TYPE: DNA
<213> ORGANISM: Homo sapiens
<220> FEATURE:
<221> NAME/KEY: primer_bind
<222> LOCATION: (1)..(18)
<223> OTHER INFORMATION: Table 6-Oct4-Backward

<400> SEQUENCE: 121
gcccccaccc tttgtgtt                                                 18

<210> SEQ ID NO 122
<211> LENGTH: 24
<212> TYPE: DNA
<213> ORGANISM: Homo sapiens
<220> FEATURE:
<221> NAME/KEY: primer_bind
<222> LOCATION: (1)..(24)
<223> OTHER INFORMATION: Table 6-Sox2-Backward

<400> SEQUENCE: 122
agttgggatc gaacaaaagc tatt                                          24

<210> SEQ ID NO 123
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table 6-Nanog-Backward

<400> SEQUENCE: 123
ggttcccagt cgggttcac                                                19

<210> SEQ ID NO 124
<211> LENGTH: 20
<212> TYPE: DNA
<213> ORGANISM: Homo sapiens
<220> FEATURE:
<221> NAME/KEY: primer_bind
<222> LOCATION: (1)..(20)
```

```
<223> OTHER INFORMATION: Table 6-Sox1-Backward

<400> SEQUENCE: 124
actccagggt acacacaggg                                          20

<210> SEQ ID NO 125
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 6-Sox2-Backward

<400> SEQUENCE: 125
ccagttgtag acacgcacct                                          20

<210> SEQ ID NO 126
<211> LENGTH: 20
<212> TYPE: DNA
<213> ORGANISM: Homo sapiens
<220> FEATURE:
<221> NAME/KEY: primer_bind
<222> LOCATION: (1)..(20)
<223> OTHER INFORMATION: Table 6-Pax6-Backward

<400> SEQUENCE: 126
tagccaggtt gcgaagaact                                          20

<210> SEQ ID NO 127
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table 6-Nestin-Backward

<400> SEQUENCE: 127
tcctgattct cctcttcca                                           19

<210> SEQ ID NO 128
<211> LENGTH: 19
<212> TYPE: DNA
<213> ORGANISM: Homo sapiens
<220> FEATURE:
<221> NAME/KEY: primer_bind
<222> LOCATION: (1)..(19)
<223> OTHER INFORMATION: Table 6-Gapdh-Backward

<400> SEQUENCE: 128
atggggaagg tgaaggtcg                                           19
```

CELL REPROGRAMMING METHOD USING PHYSICAL STIMULATION-MEDIATED ENVIRONMENTAL INFLUX

CROSS-REFERENCE TO RELATED APPLICATIONS

This application is a National Stage Application of PCT International Patent Application No. PCT/KR2016/008754 filed on Aug. 9, 2016, under 35 U.S.C. § 371, which claims priority to Korean Patent Application Nos. 10-2016-0071852 and 10-2016-0029611 filed on Jun. 9, 2016 and Mar. 11, 2016, respectively, which are all hereby incorporated by reference in their entirety.

SEQUENCE LISTING

This application contains a Sequence Listing submitted via EFS-Web and hereby incorporated by reference in its entirety. The Sequence Listing is named SEQCRF_2550-031-rev2.txt, created on Jan. 9, 2022, and 32,768 bytes in size.

TECHNICAL FIELD

The present invention relates to a cell reprogramming method using a physical stimulation-mediated environmental influx such as ultrasonic waves, laser, heat shock, etc.

The national research and development project that supports the present invention is a high-tech medical technology development project sponsored by the Ministry of Health and Welfare and the Korea Health Industry Development Institute. The project has a unique number "HI14C3297", and a research project title "Development of stem cell distribution and neural differentiation monitoring method in vivo using microRNA tracing system in ischemic brain injury model" and is supported by the Catholic Kwandong University Industry Cooperation Foundation which is a managing department.

In addition, the national research and development project supporting the present invention is a researcher support project supported by the Ministry of Science, ICT and Future Planning and the Korea Research Foundation, and has a unique number "2013R1A2A2A01068140", and a research project title "Development of microRNA-based stem cell differentiation tracking radiation biomolecule imaging method" and is supported by the Catholic Kwandong University Industry Cooperation Foundation which is a managing department.

BACKGROUND ART

A method for reprogramming somatic cells into other types of cells, progenitor cells, and stem cells is a clinically important technique in cell therapy, disease models, and transplantation. These techniques have been currently attempted through molecular and chemical methods targeting several pluripotent genes, a variety of differentiation-specific expression genes, and the like. However, existing methods are pointed out in terms of stability and efficiency, and have a disadvantage of a complicated process.

Cells are exposed to a variety of environments, which influence the gene expression of the cells in a short or long time as the cells pass through the generation, and a gene expression program of cells is regulated by stress due to an environmental change. In a cell culture environment, a medium ingredient contains various substances and ions, and the intracellular influx of such an environment may be a revolutionary method to promote cell change. However, the cells are not well transduced and infused due to the degree of polarity and size of the various components of the cell culture medium due to the cell membrane composed of phospholipids. Recently, it has been reported that the microbubbles and a cavitation effect generated by the ultrasonic wave cause the intracellular influx of the external environment, and the ultrasonic wave stimulation has a positive effect on the cell development. It is also reported that ATP is induced by ultrasonic waves and such ATP reacts with receptors of the cell membrane to induce substance transport.

In this respect, the inventors of the present invention have contrived a method of delivering various substances into a cell by temporarily damaging the somatic cell membrane using physical stimulation such as an ultrasonic wave and utilizing a cavitation effect of the medium due to the ultrasonic wave. The inventors completed the present invention by developing a cell reprogramming method using a physical stimulation-mediated environmental influx, a so-called "physical stimulation-mediated permeation of Environmental transition guided cellular reprogramming, ENTER cells".

SUMMARY OF INVENTION

Technical Problem

A purpose of the present invention is to provide a method for reprogramming differentiated cells through physical stimulation which can promote an environmental influx.

Solution to Problem

In order to achieve the above purpose, an exemplary embodiment of the present invention provides a cell reprogramming method including subjecting a mixture of differentiated or non-differentiated cells and a culture medium to physical stimulation which can promote an environmental influx, and culturing the mixture subjected to the physical stimulation for a predetermined time to obtain reprogrammed cells.

Another exemplary embodiment of the present invention provides a cell reprogramming method including subjecting a mixture of differentiated or non-differentiated cells and a culture medium to physical stimulation which can promote an environmental influx, culturing the mixture subjected to the physical stimulation for 1 day to 6 days, and mixing the differentiated or non-differentiated cells with extracellular vesicles containing exosomes isolated from the culture medium and culturing the mixture for a predetermined time to obtain reprogrammed cells.

Advantageous Effects of Invention

By subjecting differentiated cells to physical stimulation which can promote an environmental influx, such as ultrasonic waves, laser or heat shock, without the introduction of a reprogramming-inducing factor or a chemical substance to the differentiated cells, the cells can be reprogrammed with just the influx of an external environmental influx into pluripotent cells or arbitrary differentiated cells having a different expression type from the differentiated cells, and as such induction has a simple and effective production process, the possibility of an autogenic cell therapy can be made greater.

DESCRIPTION OF EMBODIMENTS

Figure 1:
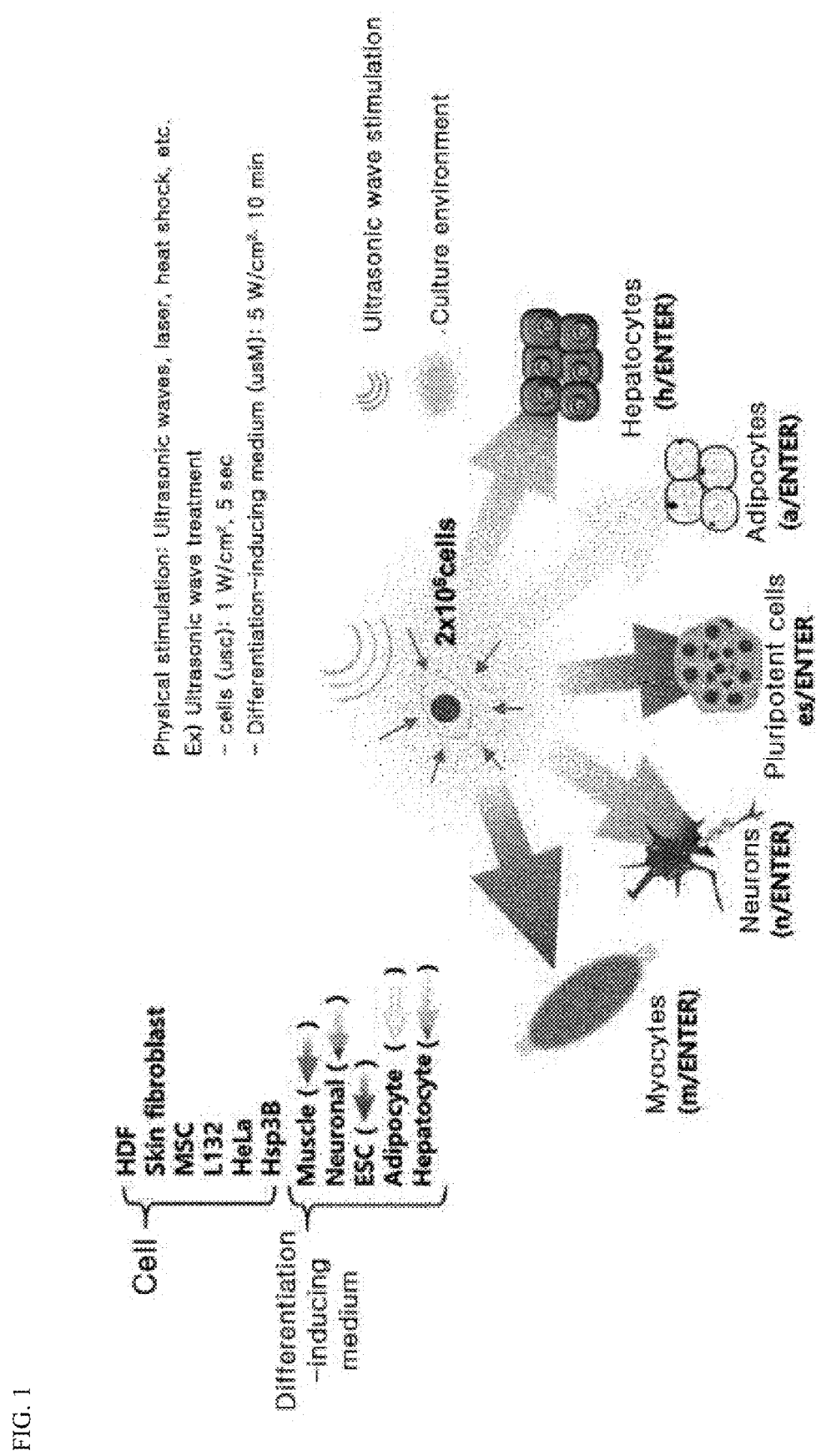
FIG. 1 is a schematic diagram showing a reprogramming method to various environmental transition guided cellular reprogramming cells according to the present invention.

Hereinafter, configurations of the present invention will be described in detail.

The present invention provides a cell reprogramming method including subjecting a mixture of differentiated or non-differentiated cells and a culture medium to physical stimulation which can promote an environmental influx, and culturing the mixture subjected to the physical stimulation for a predetermined time to obtain reprogrammed cells.

The present invention is characterized in that the differentiated or non-differentiated cells are cultured in any medium capable of inducing desired reprogrammed cells while subjecting differentiated or non-differentiated cells to physical stimulation which can promote an environmental influx such as ultrasonic waves, laser, heat shock, etc. to induce reprogramming of cells into pluripotent cells; or arbitrary differentiated cells having a different expression type from the differentiated or non-differentiated cells, for example, hepatocytes, osteoblasts, adipocytes, myocytes, neurons, astrocytes, keratinocytes, hair follicle cells, pancreatic beta cells or cardiomyocytes.

For example, if pluripotent cells are intended as reprogrammed cells, the differentiated cells may be reprogrammed into pluripotent cells by mixing the differentiated cells with a stem cell culture medium and culturing the mixture for a predetermined time by subjecting the mixture to physical stimulation.

As another example, when arbitrary differentiated cells having an expression type different from that of the differentiated cells are intended as the reprogrammed cells, the differentiated cells may be reprogrammed into arbitrary differentiated cells having a different expression type by mixing the differentiated cells with a differentiation-inducing medium of desired differentiated cells and culturing the mixture for a predetermined time by subjecting the mixture to physical stimulation.

As yet another example, the differentiated cells may be reprogrammed into desired differentiated cells with improved differentiation rate as compared with the related art by mixing the non-differentiated cells such as induced pluripotent stem cells or embryonic stem cells with a differentiation-inducing medium of desired differentiated cells and culturing the mixture for a predetermined time by subjecting the mixture to physical stimulation.

In the cell reprogramming method of the present invention, the reprogramming of the differentiated or the non-differentiated cells may be induced according to an environmental influx other than the cells through physical stimulation to the differentiated or non-differentiated cells. Such an environmental influx means an influx into the adjacent differentiated or non-differentiated cells of genetic materials, chemicals, small molecules, exosomes, or extracellular vesicles containing exosomes released from the differentiated cells subjected to the physical stimulation; or culture medium components.

According to the cell reprogramming method of the present invention, the environmental influx into the differentiated or non-differentiated cells may determine reprogramming directivity into pluripotent cells stably expressing a pluripotent marker or a triploblastic marker and differentiated cells having a different expression type from the differentiated or non-differentiated cells.

In addition, the reprogramming directivity may be determined by a kind of culture medium.

That is, as described above, the reprogramming from the differentiated or non-differentiated cells into pluripotent cells may be induced by subjecting the mixture of the differentiated cells and the stem cell culture medium to the physical stimulation, and the reprogramming from the differentiated cells into arbitrary differentiated cells having a different expression type may be induced by subjecting the mixture of the differentiated cells and the differentiation-inducing medium of the arbitrary differentiated cells to the physical stimulation, and the non-differentiated cells may be reprogrammed into arbitrary differentiated cells by subjecting the mixture of the non-differentiated cells and the differentiation-inducing medium of the arbitrary differentiated cells to the physical stimulation.

With regard to the environmental influx into the differentiated or non-differentiated cells, the present inventors have particularly considered cell membrane damage by physical stimulation and cellular secretion materials (exosomes or extracellular vesicles containing exosomes). That is, the ultrasonic waves, laser, heat shock, etc. induce temperature rise by energy, oscillation of microbubbles generated by ultrasonic waves, and induction of liquid flow generation, that is, generation of microstream along the cell membrane to apply minute damage to the cell membrane due to such an effect and induce generation of holes so that absorption of external materials is increased. It is confirmed that in a change of cytosol $Ca^{2+}$ concentration, that is, analysis of a change of cytosol $Ca^{2+}$ concentration, when the damage to the cell membrane or cell membrane fluidity is increased, a cytosol $Ca^{2+}$ concentration is instantaneously increased and thus the cell membrane fluidity is increased. According to one embodiment of the present invention, it can be seen that the $Ca^{2+}$ concentration immediately after ultrasonic wave treatment is rapidly increased and then gradually decreased to be decreased to a level of a control group not treated with ultrasonic waves and restored after the damage to the cell membrane is induced. It is also known that ATP generation and increase due to ultrasonic waves induce response on various cellular stresses and endocytosis by reacting with ATP receptors in the cell membrane. In other words, there is a relation between ATP concentration and cell damage and intracellular substance influx, and in order to verify the relation, as a result of analyzing ATP concentration in cells after ultrasonic wave treatment, the ATP concentration was higher than that in the untreated control group. In addition, expression of ionic P2X receptors and metabolic P2Y receptors in ATP-affected cell membranes is also activated in the cells treated with ultrasonic waves compared to the control group. These results indicate the possibility of influx of extracellular environment as well as intracellular damage by ultrasonic waves.

Meanwhile, it is known that the exosomes or the extracellular vesicles containing exosomes include genetic information materials (DNA, mRNA, microRNA, protein) therein, and when the exosomes or the extracellular vesicles containing exosomes released outside the cell membrane through the cell membrane damage enter other neighboring cells again, the genetic information materials in the exosomes or the extracellular vesicles containing exosomes may be delivered. Accordingly, due to ultrasonic wave stimulation, expression of pluripotent markers, triploblastic markers, or differentiated cell markers which have been maintained in a low expression state or expression-suppressed state in the cells is induced and promoted and simultaneously, the damage to the cell membrane occurs, and thus, the exosomes or the extracellular vesicles containing exosomes present in the cells including the pluripotent markers, triploblastic markers, or differentiated cell markers of which the expression is induced or promoted are released outside to be delivered to the neighboring cells. Since the neighboring cells are also in a state where the cell membrane is partially damaged, the cell membrane fluidity is increased and thus it is estimated that the efficiency in which the exosomes or the extracellular vesicles containing exosomes enter the inside of the cells is higher than that in a normal state, and it is considered that the expression-induced and promoted pluripotency, generation, differentiation-related genetic information present in the exosomes or the extracellular vesicles containing exosomes is delivered so that pluripotent cells or arbitrary differentiated cells are produced. In one embodiment of the present invention, during a pluripotent cell inducing process, the culture medium is recovered, the exosomes or the extracellular vesicles containing exosomes in the medium are extracted, and then it is confirmed whether the pluripotent cell-related pluripotent markers or differentiation markers are present therein, and as a result, it is confirmed that known pluripotent markers and differentiation markers exhibit a high expression degree and thus it is considered that the hypothesis of the present inventors is supported. In addition, it has also been shown that even in ultrasonic waves, laser, or heat shock, the exosomes or the extracellular vesicles containing exosomes are normal without malformation of karyotypes.

This hypothesis makes it possible to produce pluripotent cells or differentiated cells by inducing the release of exosomes or extracellular vesicles containing exosomes due to cell membrane damage.

As the differentiated cells, somatic cells including mammalian-derived dermal fibroblasts, skin fibroblasts, and the like; cancer cells including uterine cancer cells (HeLa), liver cancer cells (Hep3B), and the like; or endotracheal cells including pulmonary epithelial cells (L132 cells), and the like may be used.

In this specification, the term "somatic cell" refers to a cell constituting an adult and having limited differentiation potency and autopoiesis. According to one embodiment, the somatic cells may be somatic cells constituting the skin, hair, and fat of a mammal, preferably, mammalian-derived fibroblasts, but are not limited thereto.

In this specification, the term "non-differentiated cell" refers to a cell having differentiation potency and autopoiesis. Examples of the non-differentiated cells may include induced pluripotent stem cells, embryonic stem cells, progenitor cells, and the like.

In this specification, the term "pluripotent cells" refer to cells having pluripotency after physical stimulation, strictly, ultrasonic waves, laser, magnetic fields, plasma, light-emitting diodes, electrical stimulation, chemical exposure, heat shock, or acid treatment. In this specification, the pluripotency refers to a state in which pluripotent markers expressed in stem cells comprehensively are stably expressed. In addition, the pluripotency refers to a state in which triploblastic markers of endoderm, ectoderm, and mesoderm are expressed. The pluripotent cells may be used as "embryonic stem cell media-based environmental transition-guided cellular reprogramming (es/ENTER) cells.

The pluripotent cells according to the present invention are differentiated from known induced pluripotent stem cells in that the differentiation is induced well according to an external environment and a property of progenitor cell having a higher differentiation property than the property of a stem cell is higher. That is, when embryonic stem cells such as induced pluripotent stem cells are used as a cell therapeutic agent, a preparation step is required to undergo a certain degree of differentiation, and a risk factor that can be transformed into cancer is implicated, and a safety problem from using viral vectors to introduce a reprogramming inducing factor is raised. However, since the pluripotent cells of the present invention are induced without introducing a reprogramming inducing factor for genetic mutation or a reprogramming inducing substance such as a chemical material, culture through co-culture with different types of cells is not required, and thus, there is no cell contamination (problem of mixing with other cells) problem, and there is no problem in cancer generation without forming teratoma similar to cancer cells in an in-vivo experiment, thereby ensuring safety. In other words, the pluripotent cells of the present invention have an advantage that the induction process is simple and short, and the time for transplantation may be drastically shortened by treating autologous cells.

The pluripotent cell is characterized to stably express a pluripotent marker of any one of Oct3/4, S0X2, NANOG, c-MYC, KLF4, TDGF1, SSEA4, TRA-1-60, PAX6, Nestin, Brachyury, SMA, GATA4, or AFP or a triploblastic marker gene consisting of mesoderm or endoderm.

In this specification, the term "reprogramming" means a process of restoring or converting differentiated cells present in different types such as cells having no differentiation potency or cells having partial differentiation potency to final new type of cells or a state having new type of differentiation potency. In addition, a process of converting cells having differentiation potency to final new type of cells is also included. According to the present invention, when the differentiated cells are subjected to the physical stimulation which can promote the environmental influx, the differentiated cells may be reprogrammed to pluripotent cells or desired arbitrary differentiated cells having an expression type different from differentiated cells. Further, the non-differentiated cells may be reprogrammed to arbitrary differentiated cells having significantly excellent differentiation rate when being subjected to the physical stimulation which can promote the environmental influx.

Examples of the differentiated cells may include neurons (referred to as "neuronal stem cell media-based ENTER, n/ENTER") expressing any one of PAX6, SOX1, SOX2, Nestin, MAP2, TuJ1, GFAP, or 04; myocytes (referred to as "muscle differentiation media-based ENTER, m/ENTER") expressing any one of Desmin, Pax3, Actinin, SMA, GATA4, or NKX2-5; hepatocytes (referred to as "hepatocyte differentiation media-based ENTER, h/ENTER") expressing any one of AFP, HNF1a, HNF4a, CK18, or ALB, and adipocytes (referred to as "adipocyte differentiation media-based ENTER, a/ENTER") expressing any one of Pparc2, C/ebpa, aP2, or Fabp4, but are not limited thereto.

In this specification, the "culture medium" is a medium used for cell culture in vitro in a comprehensive sense, and in the present invention, the "culture medium" means a stem cell culture medium or a differentiation-inducing medium, and the stem cell culture medium more particularly means an embryonic stem cell culture medium. In addition, the "differentiation-inducing medium" is a medium used for induction to differentiated cells of general stem cells, and for example, may be a multipotent cell differentiation-inducing medium, a hepatocyte differentiation-inducing medium, an osteogenic differentiation-inducing medium, an adipocyte differentiation-inducing medium, a myocyte differentiation-inducing medium, an astrocyte differentiation-inducing medium, a neuronal cell differentiation-inducing medium, an endothelial cell differentiation-inducing medium, a keratinocyte differentiation-inducing medium, a pancreatic beta cell differentiation-inducing medium, a cardiomyocyte differentiation-inducing medium, or the like, but is not limited thereto.

The cell reprogramming method of the present invention will be described in detail with reference to FIG. 1.

First, the culture medium is mixed with differentiated or non-differentiated cells, and the mixture is subjected to the physical stimulation.

The reprogramming efficiency of the cells may be enhanced by subjecting the culture medium to the physical stimulation before subjecting the mixture including the differentiated or non-differentiated cells to the physical stimulation.

The physical stimulation may be any one of ultrasonic waves, laser, plasma, light-emitting diodes, electrical stimulation, chemical exposure, heat shock, or acid treatment.

The ultrasonic wave treatment for the culture medium may be performed by applying ultrasonic waves having an output intensity of 1 $W/cm^2$ to 20 $W/cm^2$ for 1 to minutes, specifically ultrasonic waves having an output intensity of 2 $W/cm^2$ to 10 $W/cm^2$ for 5 to 15 minutes, and more specifically ultrasonic waves having an output intensity of 3 $W/cm^2$ to 7 $W/cm^2$ for 7 to 13 minutes.

The laser treatment for the culture medium may be performed by irradiating a pulsed laser beam with a wavelength band of 300 to 900 nm for 1 minute to 20 minutes, more specifically the pulsed laser beam with the wavelength band for 3 minutes to 10 minutes, and much more specifically the pulsed laser beam with the wavelength band for 4 to 6 minutes. The wavelength band may use, for example, wavelengths of 400 nm, 808 nm, and 880 nm.

The heat shock for the culture medium may be performed at a temperature of to 50° C. for 5 to 20 minutes.

When the differentiated or non-differentiated cells are subjected to the physical stimulation, it is preferable to exposure the differentiated or non-differentiated cells at a predetermined intensity, and a cell survival rate may be reduced out of the above range.

Accordingly, the ultrasonic wave treatment for the mixture of the culture medium and the differentiated or non-differentiated cells may be performed by applying ultrasonic waves having an output intensity of 0.5 $W/cm^2$ to 3 $W/cm^2$ for 1 to 5 seconds, specifically ultrasonic waves having an output intensity of 0.7 $W/cm^2$ to 2 $W/cm^2$ for 1 to 5 seconds, and more specifically ultrasonic waves having an output intensity of 0.8 $W/cm^2$ to 1.5 $W/cm^2$ for 1 to 5 seconds.

The laser treatment for the mixture of the culture medium and the differentiated or non-differentiated cells may be performed by irradiating a pulsed laser beam with a wavelength band of 300 to 900 nm for 1 second to 20 seconds, more specifically the pulsed laser beam with the wavelength band for 3 seconds to 10 seconds, and much more specifically the pulsed laser beam with the wavelength band for 4 to 6 seconds. The wavelength band may use, for example, wavelengths of 400 nm, 808 nm, and 880 nm.

The heat shock for the mixture of the culture medium and the differentiated or non-differentiated cells may be performed by exposure for 1 to 10 minutes at a temperature condition of 40 to 50° C. and then exposure for 5 to 10 seconds at a temperature condition of 0 to 4° C.

Next, the mixture subjected to the physical stimulation is cultured for a predetermined time to obtain reprogrammed cells.

The culture of the mixture subjected to the physical stimulation may be performed for a period during which spheroid stably expressing the pluripotent marker or the differentiation marker is formed through a suspended culture or monolayer culture method, that is, for 2 to 10 days, but is not particularly limited thereto.

According to one embodiment of the present invention, the suspended culture exhibits efficiency of spheroid formation higher than that of the monolayer culture. In addition, the suspended culture has a larger number and size of spheroid than that of the monolayer culture and exhibits a constant size distribution.

According to one embodiment of the present invention, the expression of the pluripotent marker or the differentiation marker is increased or stabilized from about 3 days during the suspended culture of ultrasonic waves or laser-treated human skin fibroblasts, and reprogramming is started from this point. In addition, the expression of the pluripotent marker is increased or stabilized at about 8 days during the suspended culture of heat-treated human skin fibroblasts, and reprogramming is started from this period.

The pluripotency of the spheroid can be confirmed by expression of the pluripotent marker such as Oct3/4, SOX2, NANOG, c-MYC, KLF4, TDGF1, SSEA4, and TRA-1-60. The confirmation of the pluripotency marker may be analyzed through RT-PCR or immunocytochemistry, but is not particularly limited thereto.

In addition, the pluripotent cells of the present invention have a feature of a high level of expression of triploblastic markers, that is, ectodermal (PAX6, Nestin), mesenchymal (Brachyury, SMA), and endodermal (GATA4, AFP) markers.

In another embodiment, when the skin fibroblasts are subjected to the physical stimulation in the differentiation-inducing medium, the spheroid may be formed between about 1 to 20 days after the culture.

The differentiation marker may be at least one of PAX6, SOX1, SOX2, Nestin, MAP2, TuJ1, GFAP, or O4 when reprogrammed into neurons.

The differentiation marker may be at least one of Desmin, Actinin, Pax3, SMA, GATA4, or NKX2-5 when reprogrammed into myocytes.

The differentiation marker may be at least one of AFP, HNF1a, HNF4a, CK18, or ALB when reprogrammed into hepatocytes.

The differentiation marker may be stained with oil red O and may be at least one of Pparc2, C/ebpa, aP2, or Fabp4 when reprogrammed into adipocytes.

Further, the pluripotent cells of the present invention are characterized by having proliferation ability by expressing a proliferation marker protein, Ki-67.

In addition, when the reprogrammed pluripotent cells are co-cultured with nutritious cells, proliferation of the pluripotent cells may be increased.

Further, the cell reprogramming method of the present invention may further include culturing the pluripotent cells in the differentiation-inducing medium. Depending on a type of differentiation-inducing medium, the pluripotent cells may be differentiated into desired differentiated cells.

Examples of the differentiation-inducing medium may include a multipotent cell differentiation-inducing medium, a hepatocyte differentiation-inducing medium, an osteogenic differentiation-inducing medium, an adipocyte differentiation-inducing medium, a myocyte differentiation-inducing medium, an astrocyte differentiation-inducing medium, a neuronal cell differentiation-inducing medium, an endothelial cell differentiation-inducing medium, a keratinocyte differentiation-inducing medium, a pancreatic beta cell differentiation-inducing medium, a cardiomyocyte differentiation-inducing medium, or the like, but are not particularly limited thereto.

The present invention provides a cell reprogramming method including subjecting a mixture of differentiated or non-differentiated cells and a culture medium to physical stimulation which can promote an environmental influx, culturing the mixture subjected to the physical stimulation for 1 day to 6 days, and mixing the differentiated or non-differentiated cells with extracellular vesicles containing exosomes isolated from the culture medium and culturing the mixture for a predetermined time to obtain reprogrammed cells.

The cell reprogramming method of the present invention is characterized in that culturing the extracellular vesicles containing exosomes isolated from the differentiated or non-differentiated cells subjected to the physical stimulation with the differentiated or non-differentiated cells for a predetermined time may reprogram the extracellular vesicles containing exosomes to arbitrary differentiated cells.

The extracellular vesicles containing exosomes may be recovered through centrifugation by subjecting the mixture of the differentiated or non-differentiated cells and the culture medium to the physical stimulation which can promote an environmental influx and culturing the mixture subjected to the physical stimulation for 1 to 6 days.

The physical stimulation of the differentiated or non-differentiated cells is described above and will be omitted to avoid the duplicated disclosure.

The extracellular vesicles containing exosomes may express any one pluripotent marker or a triploblastic marker of Oct3/4, SOX2, NANOG, c-MYC, KLF4, TDGF1, SSEA4, TRA-1-60, PAX6, Nestin, Brachyury, SMA, GATA4, or AFP; any one neuronal cell marker of PAX6, Nestin, Sox1, Sox2, MAP2, TuJ1, GFAP, or O4; any one of myocyte marker of Desmin, Pax3, Actinin, SMA, GATA4, or NKX2-5; any one hepatocyte marker of AFP, HNF1a, HNF4a, CK18, or ALB; or may be stained with oil red O and express any one adipocyte marker of Pparc2, C/ebpa, aP2, or Fabp4.

For example, when the extracellular vesicles containing exosomes contain a pluripotent marker, the differentiated cells may be reprogrammed into pluripotent cells when cultured with the differentiated cells. In addition, when the extracellular vesicles containing exosomes contain a differentiation marker, the differentiated cells may be reprogrammed into arbitrary differentiated cells having a different expression type when cultured with the differentiated cells. In addition, when the extracellular vesicles containing exosomes contain the differentiation marker, the differentiated cells may be reprogrammed into arbitrary differentiated cells when cultured with the non-differentiated cells.

According to an embodiment of the present invention, the expression of various pluripotent markers in extracellular vesicles (EVs) stained with CD63, which was an exosomal marker recovered upon induction of es/ENTER, was confirmed, and in EV-treated normal human somatic cells, after 3 days of culture, pluripotent markers Oct4, Sox2, and Nanog are expressed, and thus the cell reprogramming is confirmed.

In addition, the expression of markers of neural stem cells such as Pax6 was confirmed in EVs stained with CD63, which was an exosomal marker recovered in the induction of n/ENTER, and in EV-treated normal human somatic cells, after 3 days of culture, the expression of neural stem cell markers Sox1, Sox2, Pax6, and Nestin was confirmed.

In addition, expression of a myocyte marker such as Pax3 was confirmed in EVs stained with CD63, which was an exosomal marker recovered in the induction of m/ENTER, and expression of a hepatocyte marker such as HNF1a was confirmed in EVs stained with CD63, which was an exosomal marker recovered in the induction of h/ENTER.

Thus, it can be seen that the differentiated or non-differentiated cells subjected to the physical stimulation secrete the extracellular vesicles containing the reprogramming factor. The differentiated or non-differentiated cells are treated with the extracellular vesicles and cultured for 1 to 20 days through a suspended culture or monolayer culture method. Thus they can be reprogrammed into arbitrary pluripotent or differentiated cells.

The cells that can be reprogrammed by the cell reprogramming method of the present invention may be the above-mentioned kinds of pluripotent cells or differentiated cells, and the disclosure thereof will be omitted to avoid the duplicated disclosure.

Hereinafter, the present invention will be described in detail by Examples below. However, the following Examples are just illustrative of the present invention, and the contents of the present invention are not limited to the following Examples.

EXAMPLES

<Example 1> Experiment for Verifying Intracellular Environmental Influx by Physical Stimulation This Example is an experiment for verifying intracellular environmental influx by physical stimulation, and to this end, the cells, primary HDF cells purchased from Invitrogen, were cultured in a DMEM added with 10% FBS (Gibco) and 1% penicillin/streptomycin (Gibco), the ultrasonic wave treatment for the culture medium was performed at 5 W/cm$^2$ for 10 minutes, the cell treatment was performed in 1×10$^6$ cells at 1 W/cm$^2$ for 5 seconds, and then 2×10$^5$ cells were cultured in a 35 mm culture dish with the treated culture medium.

For SEM image analysis, untreated HDF cells and cells immediately after the above treatment and cultured for 2 hours in a 5% CO$_2$ incubator at 37° C. were fixed with 4% paraformaldehyde at 4° C. for 12 hours, and then treated with a 0.1% tannic acid solution for 1 hour and a 1% osmium tetroxide solution for 2 hours and dehydrated with acetone for each concentration step. Thereafter, the cells were dried with liquid CO$_2$ and fixed on a surface coated with gold-palladium to be observed by an electron microscope (1555 VP-FESEM, Carl Zeiss).

For live/dead image analysis, untreated HDF and cells immediately after ultrasonic wave treatment and cultured for 2 hours in a 5% CO$_2$ incubator at 37° C. were stained with a live/dead viability/cytotoxicity assay kit (Molecular Probes, Eugene, OR, USA). In the straining process, after 2 μM calcein (live cell staining dye) and 4 μM ethidium homodimer-1 (EthD-1, dead cell staining dye) were added to a cell culture medium, living cells were cultured at 37° C. in a 5% CO$_2$ incubator for 30 minutes, and then red fluorescence (EthD-1 staining, dead or damaged cells, excitation/emission, 528/617 nm) and green fluorescence (calcein staining, living cells, excitation/emission, 494/517 nm) were analyzed by a fluorescence microscope (IX3-ZDC, Olympus).

As shown in FIG. 2A, the cell membrane was damaged by the ultrasonic waves and a hole capable of introducing the external environment was formed, and such damage was recovered after 2 hours.

The cells were stained using a live/dead kit, which was used to analyze cell death, in order to confirm the damaged cells after ultrasonic wave stimulation and recovery of the cells.

As shown in FIG. 2B, the cells were treated with ultrasonic waves, stained immediately after treatment, and stained 2 hours later. As a result, the cells with both green fluorescence and red fluorescence were observed immediately after treatment, and although the number of cells showing red fluorescence after 2 hours was significantly reduced, the red fluorescence was reduced since the cell membrane was recovered as shown in FIG. 2A.

It is considered that the cell damage is generated by the ultrasonic wave stimulation, but can be restored, and a medium environmental influx can be possible due to the cell membrane damage by such stimulation, and a phenomenon caused by influx of intracellular substances was analyzed.

Figure 2:
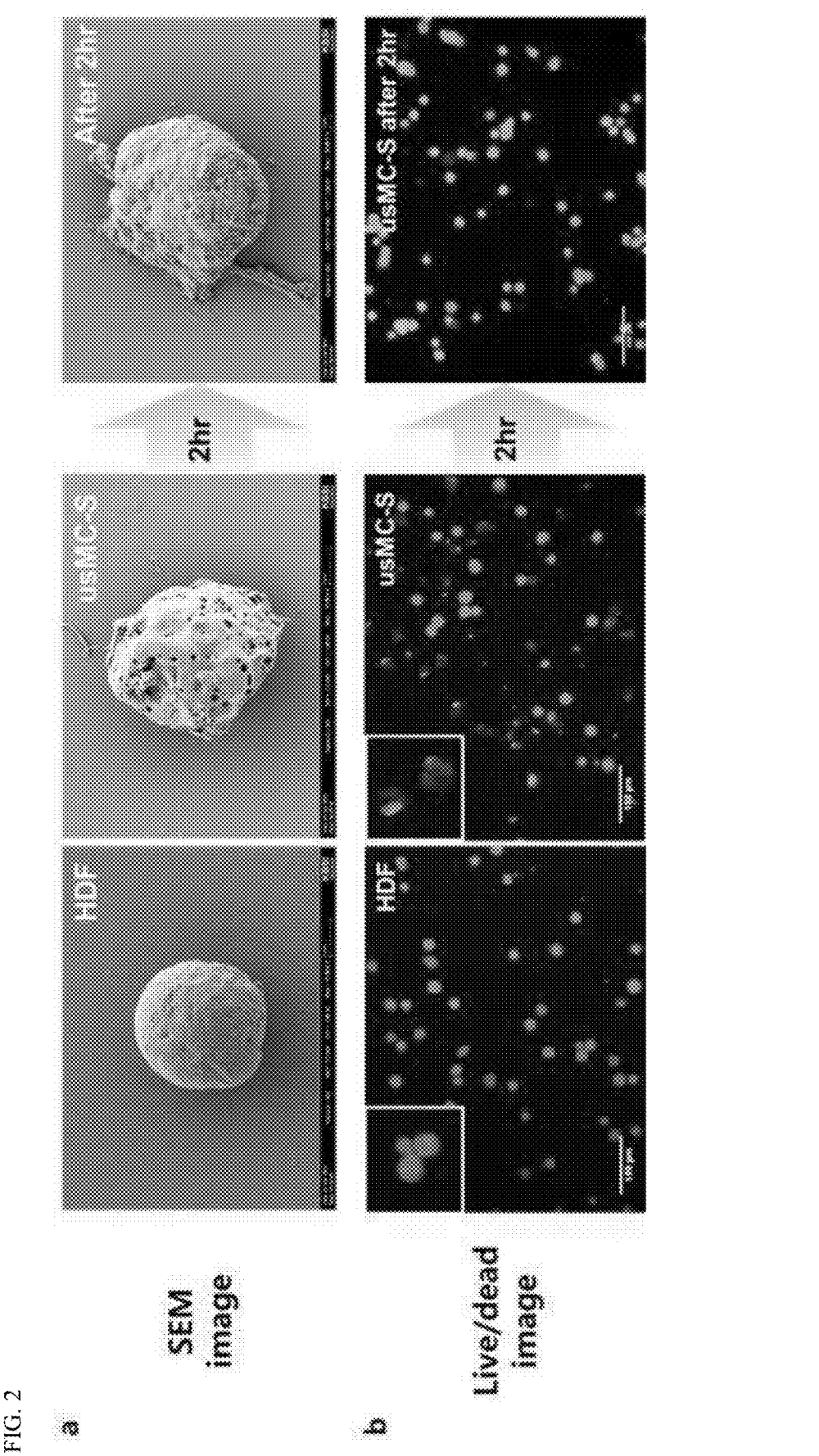
FIG. 2 shows results of cell membrane damage by ultrasonic wave stimulation and recovery, in which (A) is a cell surface image photographed by an SEM, and (B) is a live/dead kit staining image.

On the other hand, in FIG. 2, ultrasound-exposed medium and cells (usMC) refers to a case in which ultrasonic waves are treated to each of the cells and the culture medium, and usMC-S means usMC in the suspended culture.

<Example 2> Experiment for Verifying Influx of External Substances to Cells by Physical Stimulation A change in intracellular calcium concentration sensitive to the influx of the external substances in the cells was measured, and in order to confirm the possibility of substance influx according to ATP generation by ultrasonic waves, the expression of ATP receptors, which have been known that the receptor in the cell membrane opens an external substance influx passage on a cell membrane by the ATP measurement and the ATP reaction in the cells, was analyzed by RT-PCR.

Calcium concentration was analyzed using a Fluo-4 NW Calcium Assay Kit (Molecular Probes). Untreated HDF cells and cells (usMC-S) exposed to a medium treated with ultrasonic waves after being directly treated with ultrasonic waves (1 W/cm$^2$, 5 seconds) were mixed with an assay buffer among the components in the kit, respectively, divided with 3×10$^4$ cells per well of a 96-well plate, and then mixed with 50 μl of Fluo-4 NW per well, and thereafter, fluorescence in a range of an excitation wavelength of 494 nm and an emission wavelength of 516 nm was measured at 10-second intervals for 15 minutes by a Varioskan flash fluorescent microplate fluorometer (Thermo Fisher Scientific, Waltham, MA, USA).

ATP was measured using an adenosine 5'-triphosphate (ATP) bioluminescent assay kit. After the untreated cells and the cells (usMC-S) exposed to a medium treated with ultrasonic waves after being directly treated with ultrasonic waves (1 W/cm$^2$, 5 seconds) were divided with 3×10$^4$ cells per well of a 96-well plate, the cells were cultured at room temperature for 3 minutes by dividing 100 μl of an ATP assay mix and ATP standard material per well, and thereafter, the luminescence intensity was measured by a Varioskan flash fluorescent microplate fluorometer (Thermo Fisher Scientific).

For the RT-PCR for ATP receptor expression analysis, RNA was extracted from the treated cells by using an RNeasy plus mini kit (Qiagen, Hilden, Germany) and cDNA was synthesized by a Super ScripII kit (Invitrogen, Carlsbad CA, USA). The PCR was performed, after mixing cDNA and primers with a PCR premix (Bioneer, Daejeon, Korea), under conditions of denaturation at 95° C. for 5 min, 35 cycles at 95° C. for 30 sec, and gradient (50 to 65° C.) for 30 sec, and at 72° C. for 1 min, and at 72° C. for 15 min using a thermal cycler dice PCR machine (TP600, TAKARA, Otsu, Japan).

TABLE 1

PCR primer list of P2 receptors

| Gene code | Primer sequence (5'-3') | |
|---|---|---|
| | Forward | Backward |
| P2X4 | TCTCAACAGGCAGGTGCGTAG CTT (SEQ ID NO: 1) | GCTCAACGTCCCGTGTATCGA GG (SEQ ID NO: 65) |
| P2X7 | CAGAAGGCCAAGAGCAGCGG TT (SEQ ID NO: 2) | GGACACGTTGGTGGTCTTGTC GTCA (SEQ ID NO: 66) |
| P2Y1 | CTTGGTGCTGATTCTGGGCTG (SEQ ID NO: 3) | GCTCGGGAGAGTCTCCTTCTG (SEQ ID NO: 67) |
| P2Y2 | CCGCTCGCTGGACCTCAGCTG (SEQ ID NO: 4) | CTCACTGCTGCCCAACACATC (SEQ ID NO: 68) |
| P2Y11 | GAGGCCTGCATCAAGTGTCTG (SEQ ID NO: 5) | ACGTTGAGCACCCGCATGATG (SEQ ID NO: 69) |

Figure 3:
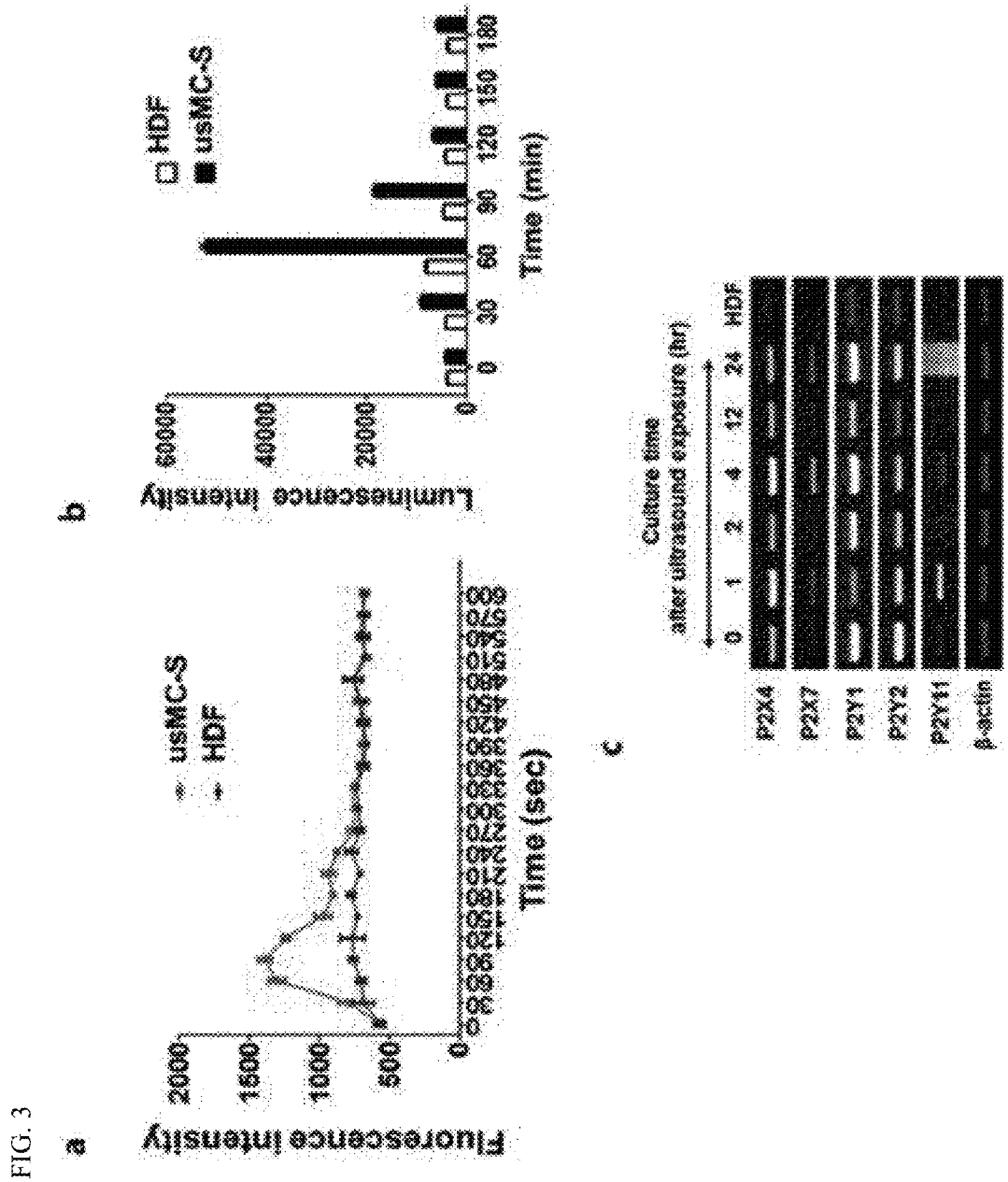
FIG. 3 shows an (A) intracellular Ca influx analysis, (B) ATP reaction analysis, and (C) a RT-PCR analysis result for ATP receptor gene expression.

As shown in FIG. 3, the intracellular calcium influx after the ultrasonic wave stimulation was increased up to 60 seconds, the intracellular ATP concentration was maximally increased at 60 minutes, and the expression of the ATP receptors in the cell membrane was also increased at 1 hour and 4 hours, respectively. It was confirmed by the increase of calcium concentration that the external substance was introduced into the early cells by the ultrasonic wave stimulation, and it can be seen that the ATP was generated by the ultrasonic wave and as a result, the ATP receptor reacted, and then the cell membrane passage was opened and thus, the external substances can be introduced.

<Example 3> Experiment for Verifying Influx of External Substances into Cells by Physical Stimulation Using QD605

QD605 was set as an external substance and whether the QD605 was introduced into the cells by ultrasonic waves was confirmed. QD605 is a fluorescent nano-material that is known to be poorly permeable in living cells, and the influx of the external substance into the cells by the ultrasonic waves using QD605 was confirmed.

To this end, like Example 1, HDF was subjected to the ultrasonic wave stimulation and treated with 100 pmol of QD605, and presence of QD605 in a single cell and spheroid was confirmed after 24 hours.

Figure 4:
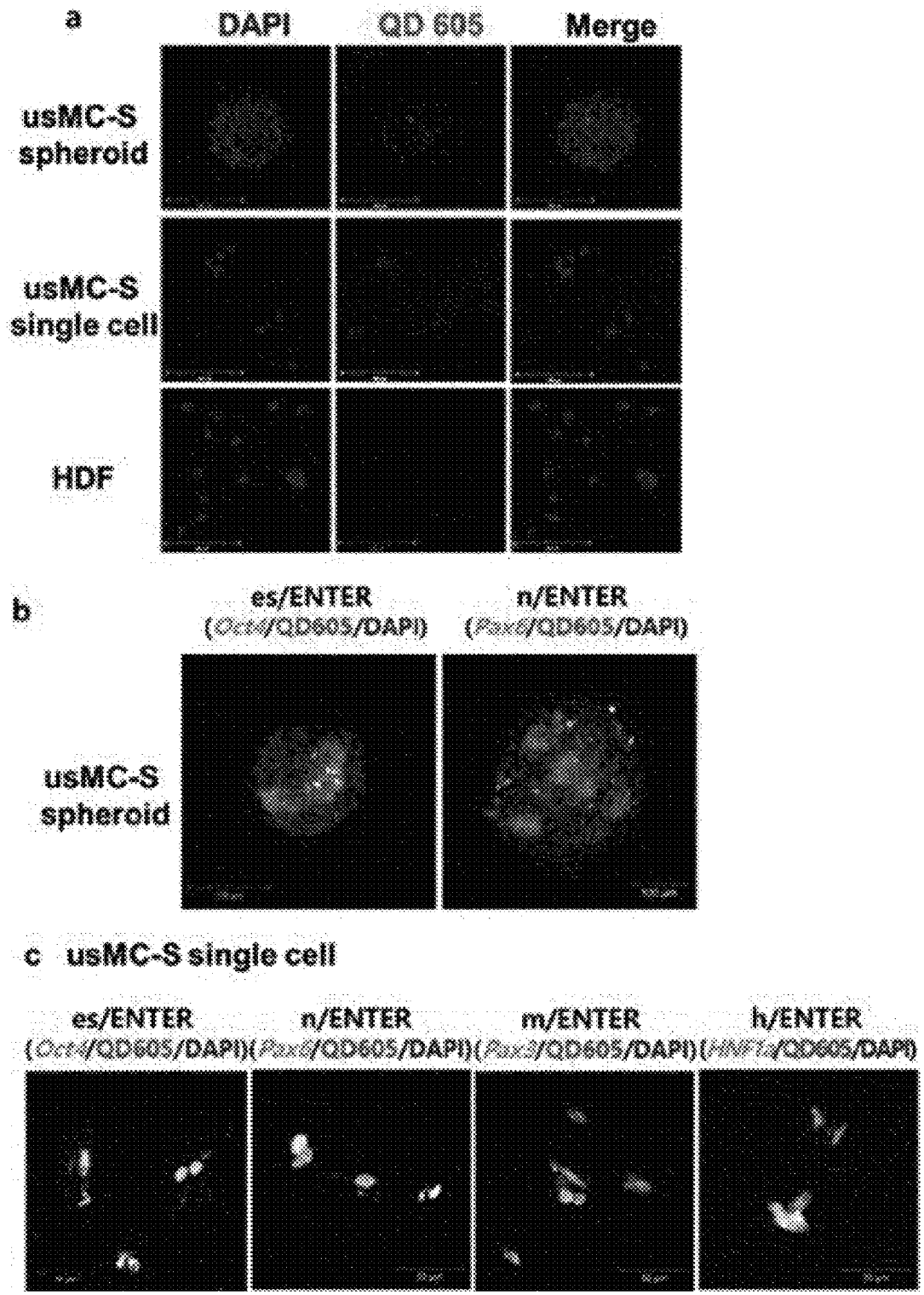
FIG. 4 shows results of showing a possibility of influx of external substances into cells by ultrasonic wave stimulation using QD605, in which (A) shows a QD605 influx analysis result in ultrasound-exposed medium and cells (usMC-S) spheroids and single cells, and (B) and (C) show QD605 influx analysis and expression of transcription factors results in (B) a usMC-S spheroid and (C) single cells for each environmental.

As shown in FIG. 4, no fluorescence was observed in HDF that was not subjected to ultrasonic wave stimulation. However, fluorescence was observed in the HDF subjected to ultrasonic wave stimulation.

In order to confirm the possibility of cell changes due to the influx of external substances, 100 pmol of QD605 was added after treating ultrasonic waves in each medium environment (ES, neuroprogenitor, hepatocyte, muscle), and after 24 hours, expression of transcription factors (ES: Oct4, Neuroprogenitor: Pax6, Hepatocyte: HNF1a, Muscle: Pax3) during each differentiation process was confirmed through ICC.

As shown in FIGS. 4B and 4C, the transcription factors were observed in each of the cells and spheroid containing the external substance (QD605). This is a result indicating the possibility of cell reprogramming due to the influx of external substances.

During the experiment, only es/ENTER and n/ENTER among four environmental influx samples formed spheroids. However, m/ENTER and h/ENTER did not form spheroids. The reason lies in the characteristics of the cells and the medium composition. In the case of ES and neuroprogenitors, spheroid or sphere was formed in the suspended culture process, but in the case of myocytes or hepatocytes, the spheroid was not formed. This is because the cells were adhered and cultured in a coated culture dish during the differentiation induction process, and particularly, FBS was contained in the medium of myocytes, but since the FBS increased cell adhesion, the spheroid was not formed.

<Example 4> Analysis of Exosomes in Cell Culture Medium Subjected to Physical Stimulation Since the cell stimulation by the ultrasonic waves is not equally stimulated in all cells, reprogramming of the cells may occur in some cells, and the possibility of cell exchange between these changed cells and non-changed cells was considered. Recently, with reference to the possibility of intercellular material exchange by exosomes, there is a possibility that the exosomes in the culture media released from the cells treated with ultrasonic waves contain genetic materials. There is a possibility that the material secreted from the reprogrammed cells contains a genetic material which plays an important role in the reprogramming, and the exosomes in the culture medium cultured after ultrasonic wave treatment were recovered during medium exchange for each culture time, RNAs of the exosomes in the culture medium were extracted by Amicon Ultra-0.5 kit (Millipore), and the cDNA synthesis was performed by Super ScripII kit (Invitrogen, Carlsbad CA, USA). The PCR was performed, after mixing cDNA and primers with a PCR premix (Bioneer, Daejeon, Korea), under conditions of denaturation at 95° C. for 5 min, 35 cycles at 95° C. for 30 sec, and gradient for 30 sec, and at 72° C. for 1 min, and at 72° C. for 15 min using a thermal cycler dice PCR machine (TP600, TAKARA, Otsu, Japan) (Table 2).

Figure 5:
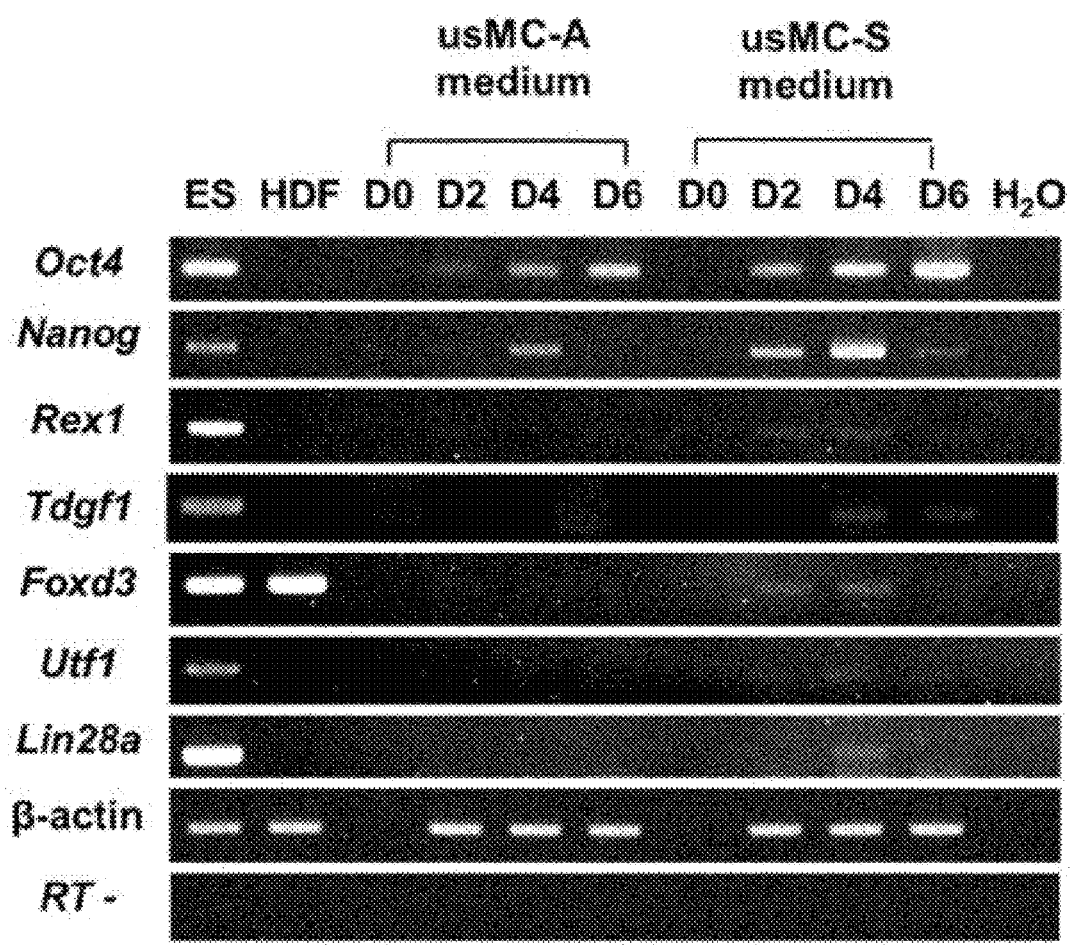
FIG. 5 shows a RT-PCR analysis result of RNA of exosomes in a culture medium treated with ultrasonic wave.

As shown in FIG. 5, the expression of pluripotent RNA in RNAs of the exosomes was confirmed.

Meanwhile, in FIG. 5, usMC refers to a case where the cells and the culture medium are treated with ultrasonic waves, respectively, and usMC-A means monolayer-cultured usMC.

TABLE 2

| Gene code | Primer sequence (5'-3') Forward | Primer sequence (5'-3') Backward | Annealing temperature (° C.) |
|---|---|---|---|
| Oct4 (POU5F1) | GACAGGGGAGGGGAGG AGCTAGG (SEQ ID NO: 6) | CTTCCCTCCAACCAGTTGC CCCAAAC (SEQ ID NO: 70) | 60 |
| Sox2 | GGGAAATGGGAGGGTGC AAAAGAGG (SEQ ID NO: 7) | TTGCGTGAGTGTGGATGG GATTGGTG (SEQ ID NO: 71) | 63 |
| Nanog | CAGCCCCGATTCTTCCACC AGTCCC (SEQ ID NO: 8) | CGGAAGATTCCCAGTCGG GTTCACC (SEQ ID NO: 72) | 64 |
| Utf1 | CCGTCGCTGAACACCGCC CTGCTG (SEQ ID NO: 9) | CGCGCTGCCCAGAATGAA GCCCAC (SEQ ID NO: 73) | 65 |
| Lin28a | AGCGCAGATCAAAAGGAG ACA (SEQ ID NO: 10) | CCTCTCGAAAGTAGGTTG GCT (SEQ ID NO: 74) | 50 |
| Rex1 | CAGATCCTAAACAGCTCG CAGAAT (SEQ ID NO: 11) | GCGTACGCAAATTAAAGTC CAGA (SEQ ID NO: 75) | 52 |
| Fgf4 | CTACAACGCCTACGAGTC CTACA (SEQ ID NO: 12) | GTTGCACCAGAAAAGTCA GAGTTG (SEQ ID NO: 76) | 55 |
| Foxd3 | AAGCTGGTCGAGCAAACT CA (SEQ ID NO: 13) | CTCCCATCCCCACGGTACT A (SEQ ID NO: 77) | 50 |
| Esg1 | ATATCCCGCCGTGGGTGA AAGTTC (SEQ ID NO: 14) | ACTCAGCCATGGACTGGA GCATCC (SEQ ID NO: 78) | 60 |
| Tdgf1 | CTGCTGCCTGAATGGGGG AACCTGC (SEQ ID NO: 15) | GCCACGAGGTGCTCATCCA TCACAAGG (SEQ ID NO: 79) | 65 |
| c-Myc | AATGAAAAGGCCCCCAAG GTAGTTATCC (SEQ ID NO: 16) | GTCGTTTCCGCAACAAGTC CTCTTC (SEQ ID NO: 80) | 50 |
| Klf4 | CCCACATGAAGCGACTTC CC (SEQ ID NO: 17) | CAGGTCCAGGAGATCGTT GAA (SEQ ID NO: 81) | 54 |

<Example 5> Experiment for Verifying Material Delivery by Exosomes

Since the expression of a pluripotent marker was confirmed in exosomes in the culture medium of cells treated with ultrasonic wave treatment in Example 4 above, whether a genetic material and a protein were delivered by the exosomes was confirmed.

Figure 6:
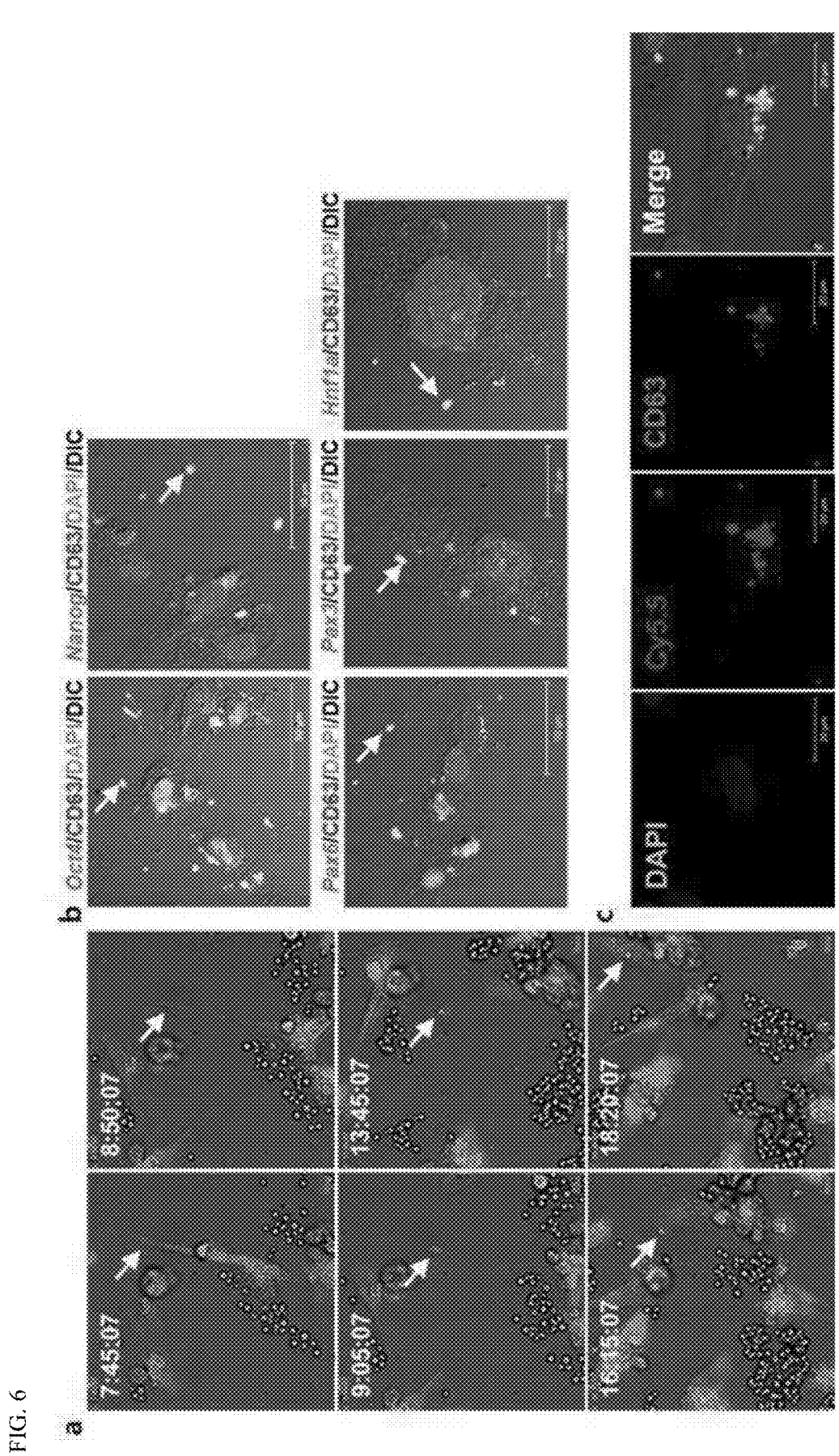
FIG. 6 shows results of material delivery by exosomes, in which (A) is an image capturing a process of moving QD605 to another cell by exosomes, (B) shows the expression of a protein marker in exosomes, and (C) shows a result of a poly(A)$_{27}$-Cy5.5 delivery experiment by exosomes.

As a result of photographing images of living cells by adding QD605 after ultrasonic wave treatment, as shown in FIG. 6A, it was confirmed that QD605 of the cells introduced with QD605 on 7 hours and 45 minutes was separated with a part of the cytoplasm to be moved to other cells.

The separated part of the cytoplasm was expected to be exosomes, and the usMC-treated cells were exposed to various medium environments, immobilized in 4% paraformaldehyde for 10 minutes, and embedded in PBS containing 0.1% Triton X-100 for 40 minutes. The cells were blocked with a PBS solution containing 5% (v/v) goat serum for 1 hour and an exosome marker CD63 (1:100, Santa Cruz Biotechnology) and initial expression markers of cells induced by each differentiation-inducing medium, such as embryonic stem cells (Oct4 1:200; Nanog 1:200; abeam), neural stem cells (Pax6, 1:200; abeam), myocytes (Pax3, 1:200; abeam), and hepatocytes (HNF1a, 1:200; Cell Signaling Technology) were stained overnight at 4° C. with primary antibodies. The cells were washed with a PBS buffer containing 0.03% Triton X-100, stained with secondary antibodies, Alexa-488 or -594 binding anti-rabbit, and anti-mouse antibodies (1:1000, Thermo, excitation/emission, 495/519 nm, excitation/emission, 590/617 nm) at room temperature for about 1 hour and 30 minutes, washed with a PBS buffer containing 0.03% Triton X-100, and then mounted on a mounting sol containing DAPI (Vector Laboratories, Inc., Burlingame, CA, excitation/emission, 420/480 nm), and images were analyzed with a confocal laser fluorescence microscope (LSM 700; Carl Zeiss).

As shown in FIG. 6B, those estimated to be a part of the cytoplasm that was released around the cells were stained with CD63, and the expression of the pluripotent cell marker such as Oct4 and Nanog was confirmed in extracellular vesicles (EVs) stained with CD63, which was an exosome marker, during es/ENTER induction, the expression of the neural stem cell marker such as Pax6 was confirmed in the EVs stained with CD63, which was the exosome marker, during n/ENTER induction, the expression of the myocyte marker such as Pax3 was confirmed in the EVs stained with CD63, which was the exosome marker, during m/ENTER induction, and the expression of the hepatocyte marker such as Hnf1a was confirmed in the EVs stained with CD63, which was the exosome marker, during h/ENTER induction.

From the above results, it was hypothesized that the exosomes were separated from the cytoplasm and contained genetic materials and proteins to be delivered to the surrounding cells so as to induce changes in surrounding cells. In order to prove this hypothesis, it was considered that the poly(A)$_{27}$-Cy5.5 may be delivered by the exosomes when the exosomes were extracted and stained with CD63 (stained to distinguish the newly injected exosomes because the exosomes existed even in the cultured cells), introduced with a genetic material expressed by poly(A)$_{27}$-Cy5.5 and cultured with untreated HDF.

As shown in FIG. 6C, it was confirmed that the exosomes stained with CD63 were found in the cells, and cy5.5 was expressed like CD63. This means that the gene (poly-A) injected by the exosomes was delivered.

<Example 7> Co-Culture of Cells Subjected to Physical Stimulation and Normal Cells Since the genetic material may be delivered by the exosomes, it has been hypothesized that the exosomes secreted from the cells cultured in a human ES medium may change the properties of surrounding cells or untreated cells. To verify this, the exosomes were extracted from the 2-day cultured medium of cells treated with ultrasonic wave cultured in the human ES medium environment, and the exosome extract was mixed and cultured for 6 days in a process of culturing the untreated cells in the human ES medium and a fibroblast culture medium, DMEM.

Figure 7:
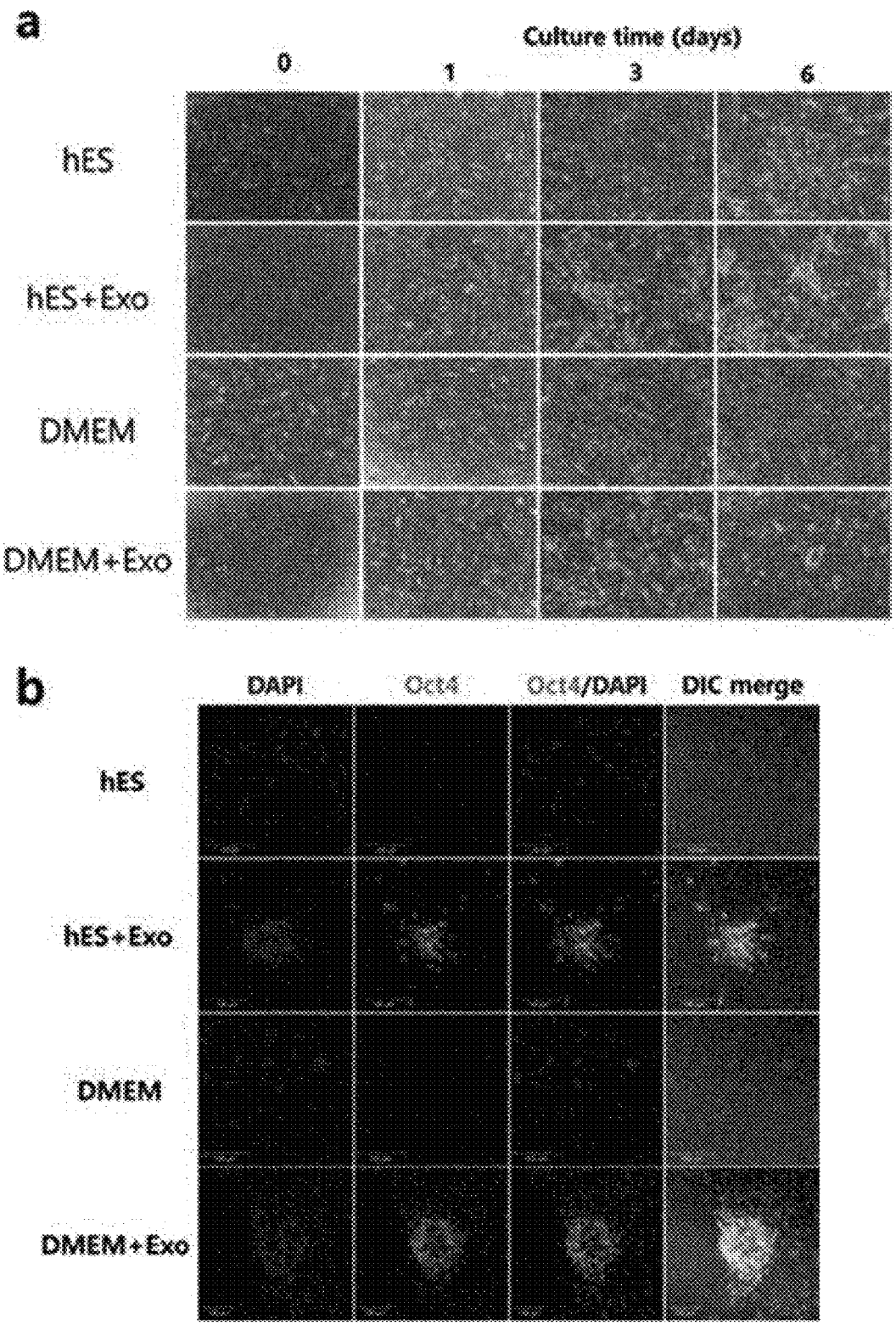
FIG. 7 shows changes in cells according to co-culture of exosomes in a culture medium of cells treated with ultrasonic waves and cells not treated with ultrasonic waves, in which (A) shows a change in cell morphology according to a culture time and (B) shows a result of Oct4 expression in exosomes and cells cultured for 6 days.

As a result, spheroid was produced in a group added with exosomes (FIG. 7A), and as a result of verifying the Oct4 expression in the cells, the expression of a pluripotent marker, Oct4, was observed (FIG. 7B). This indicates that the delivery of the genetic material by the exosomes may induce the cell reprogramming.

<Example 8> Direct Reprogramming of Fibroblasts

In Examples 1 to 7 above, a possibility of cell reprogramming and reprogramming up to surrounding cells by a change in medium environment was verified, and based on this, the reprogramming of cells was confirmed by applying various medium environments.

Figure 8:
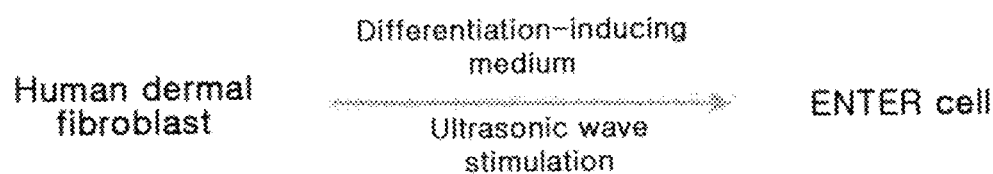
FIG. 8 shows a direct differentiation method of human dermal fibroblasts according to the present invention.

To this end, as shown in FIG. 8, human fibroblasts were collected into 1×10$^6$ cells in a 1 mL differentiation-inducing medium, treated with ultrasonic waves at an intensity of 1 W/cm$^2$ for 5 seconds, divided into 2×10$^5$/Well in a 35 mm culture dish or 6-well plate, and then cultured in a 2 mL differentiation-inducing medium treated with the ultrasonic waves at an intensity of 10 W/cm$^2$ for 10 minutes.

Although there is a difference depending on a type of differentiation-inducing medium, spheroid was formed between about 2 days and 6 days after culturing.

In addition, it was observed that intracellular bubbles were formed by culturing for 20 days after usMC treatment using the adipocyte differentiation-inducing medium, and oil red O, a lipid staining reagent for discriminating adipocytes, was stained by analysis of the bubbles. This is an indicator that cells produce fat (FIG. 9A).

Figure 9:
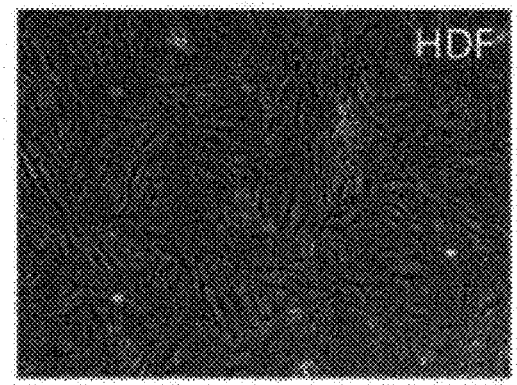
FIG. 9 shows results of differentiation of human dermal fibroblasts treated with ultrasonic waves in an adipocyte differentiation-inducing medium into adipocytes, in which (A) shows a change in cells on day 20 after induction of differentiation and an oil red O staining result of adipocytes and (B) shows a RT-PCR analysis result for adipocyte marker gene expression of differentiation-induced cells.
Figure 9:
Figure 9:
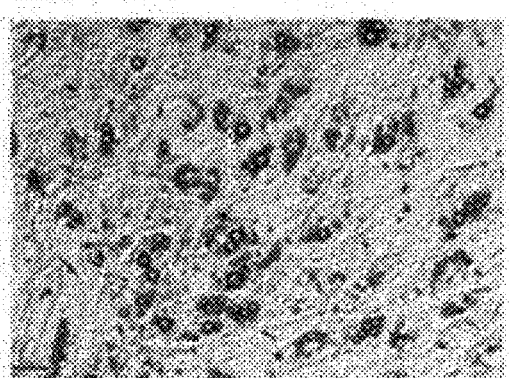
Figure 9:
Figure 9:
Figure 9:
Figure 9:
Figure 9:
Figure 9:

The expression of adipocyte marker genes, Pparc2, C/ebpa, aP2, and Fabp4 was confirmed by RT-PCR after the cell RNA was extracted, and as a result, the expression after differentiation induction was increased (FIG. 9B).

In addition, in order to confirm the differentiation of HDF into neuroprogenitors by a neural stem cell (neuroprogenitor) differentiation-inducing medium and ultrasonic waves, the expression of neuroprogenitor markers, Oct4, Sox2, Pax6, and Nestin were confirmed by staining by immunocytochemistry in spheroids produced on day 3 after differentiation induction and attached cells.

Figure 10:
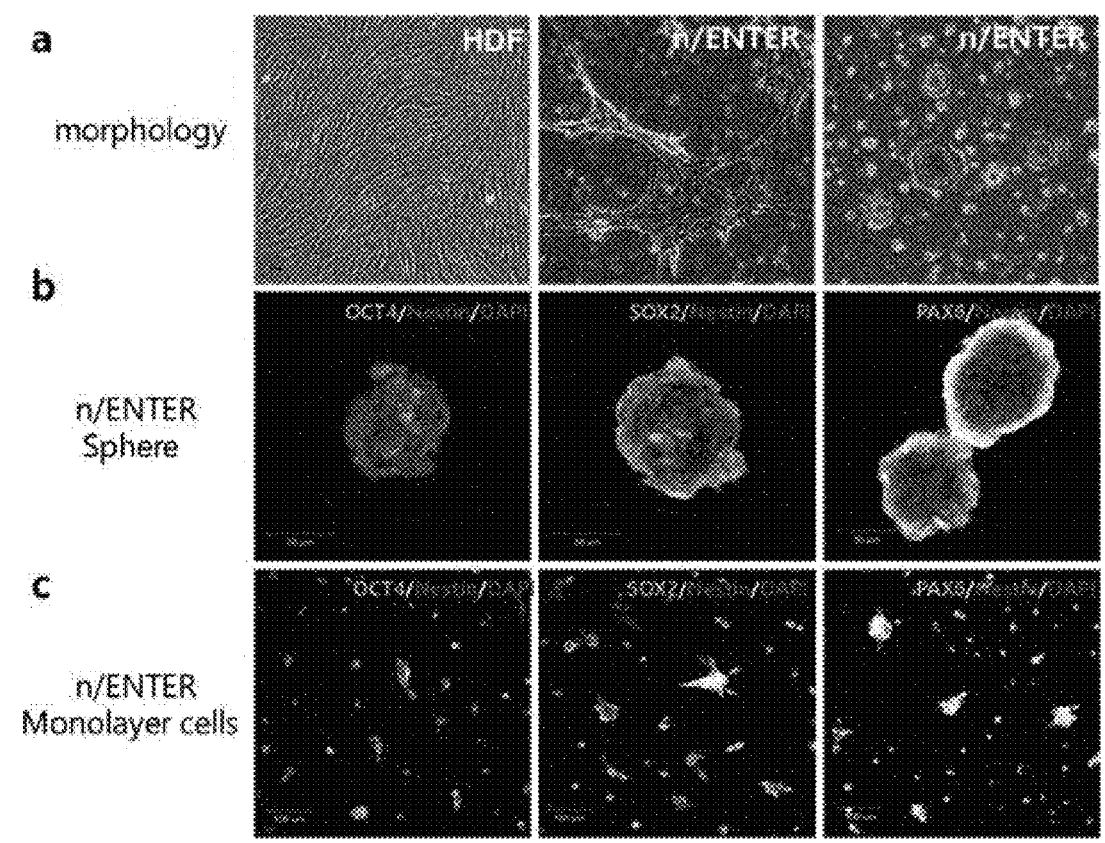
FIG. 10 shows results of differentiation of human dermal fibroblasts treated with a neural stem cell differentiation-inducing medium and ultrasonic waves into neuroprogenitors, in which (A) shows a result of analyzing changes in cells on day 3 after induction of differentiation, (B) shows a result of analyzing expressions of a differentiation-induced neuroprogenitor marker, and (C) shows a result of analyzing expressions of a neuroprogenitor marker in attached cells.

FIG. 10A shows the morphology of the differentiated cells and FIG. 10B shows the neuroprogenitor markers in the spheroid, in which it was confirmed that if differentiation was induced, the expression of Oct4 was reduced and the expression of Sox2, Pax6, and Nestin was high. FIG. 10C shows the expression in the attached cells, and is the same expression pattern as above. At this time, the markers of neuroprogenitors and neural stem cells are Sox2, Pax6, and Nestin. Oct4 is a pluripotent marker, and the expression of Oct4 is decreased in adult stem cells and progenitor cells.

TABLE 3

| Composition of differentiation-inducing medium | | |
|---|---|---|
| | Components | Content |
| Neuroprogenitor differentiation- inducing medium | DMEM F12 bFGF EGF B27 supplement (×50) N2 supplement (×100) | 20 ng/ml 20 ng/ml 1/50 1/100 |

Figure 11:
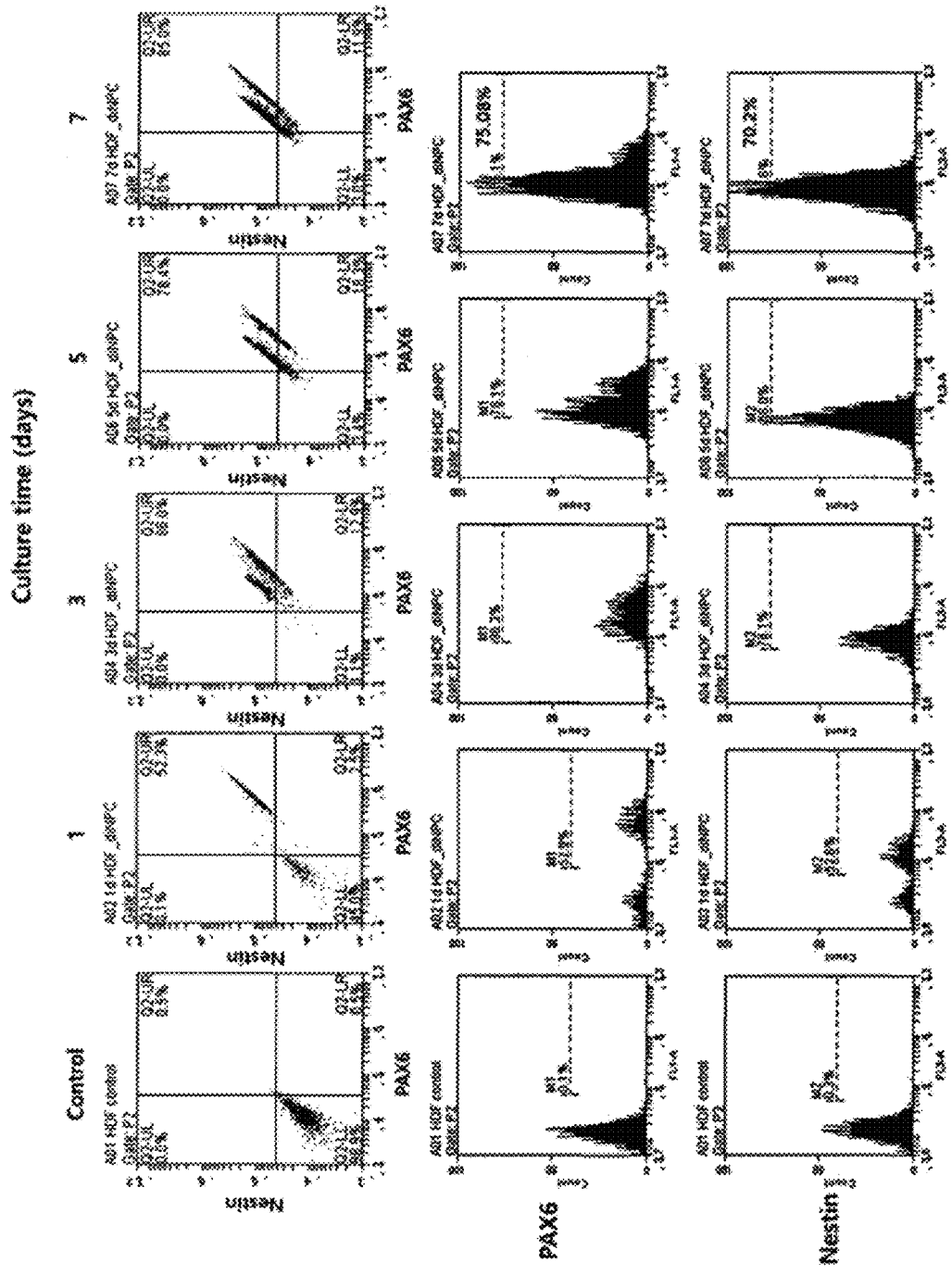
FIG. 11 shows a flow cytometry analysis result which analyzed expression of Pax6 and Nestin in cells (n/ENTER cells) differentiation-induced into neuroprogenitors.

FIG. 11 shows a result of analyzing an expression pattern of Pax6/Nestin in the cells differentiation-induced for 7 days after induction of differentiation through flow cytometry, in which the expression of Pax6 and Nestin was relatively 50% or more on day 1 after the treatment, and the expression of Pax6 and Nestin was the highest on day 3.

Figure 12:
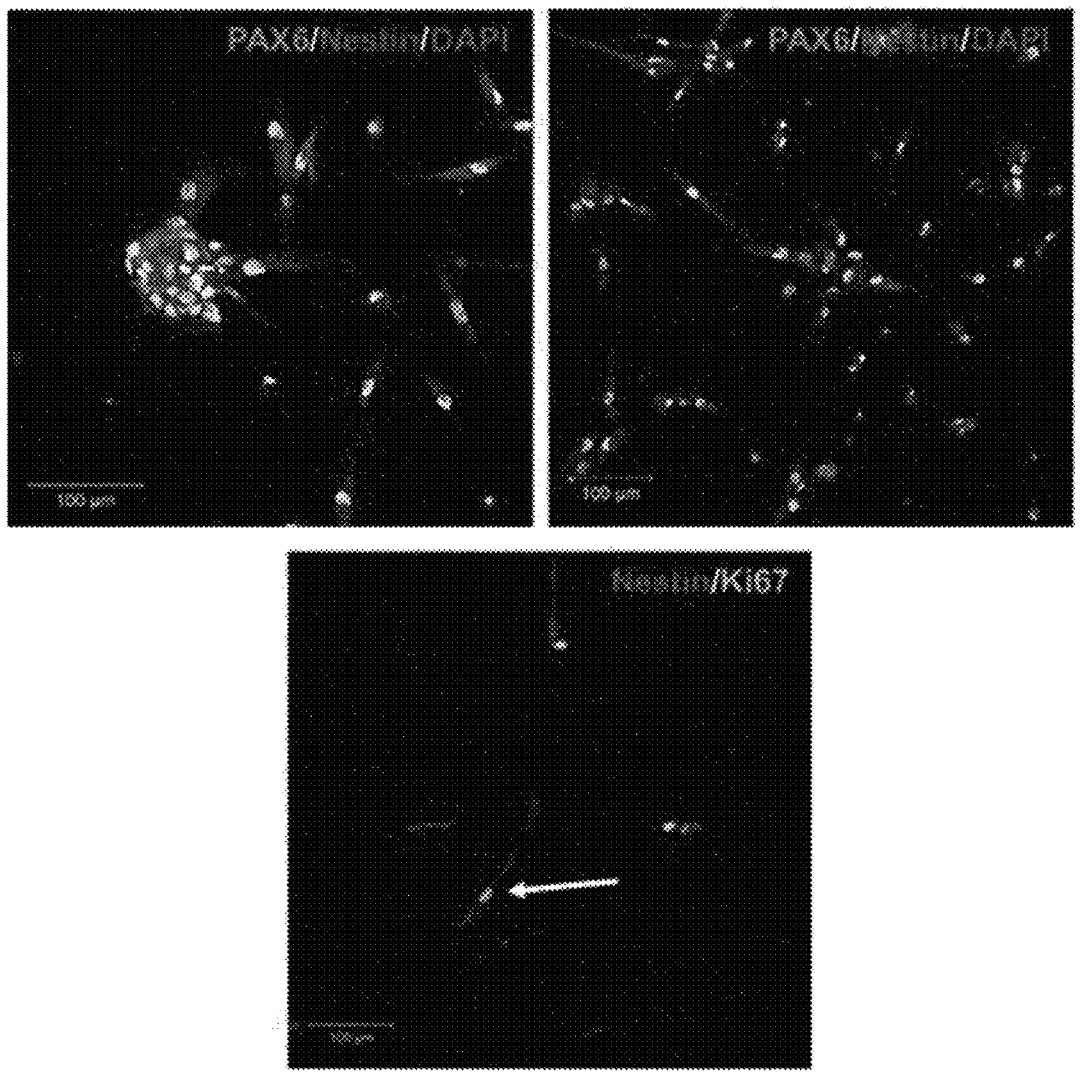
FIG. 12 shows expression of a proliferation marker, Ki67, in n/ENTER cells.

FIG. 12 shows the expression of ki67 to confirm the proliferation of cells expressing the neuroprogenitor marker (Pax6/nestin) on day 3 after induction of differentiation, in which in cells indicated by a white arrow, the expression of ki67 in the cells where Nestin was expressed may be confirmed. This result indicates that the differentiation-induced cells have proliferation ability. In FIG. 12, the arrow is a marker indicating that the Nestin-stained cells are proliferating.

Figure 13:
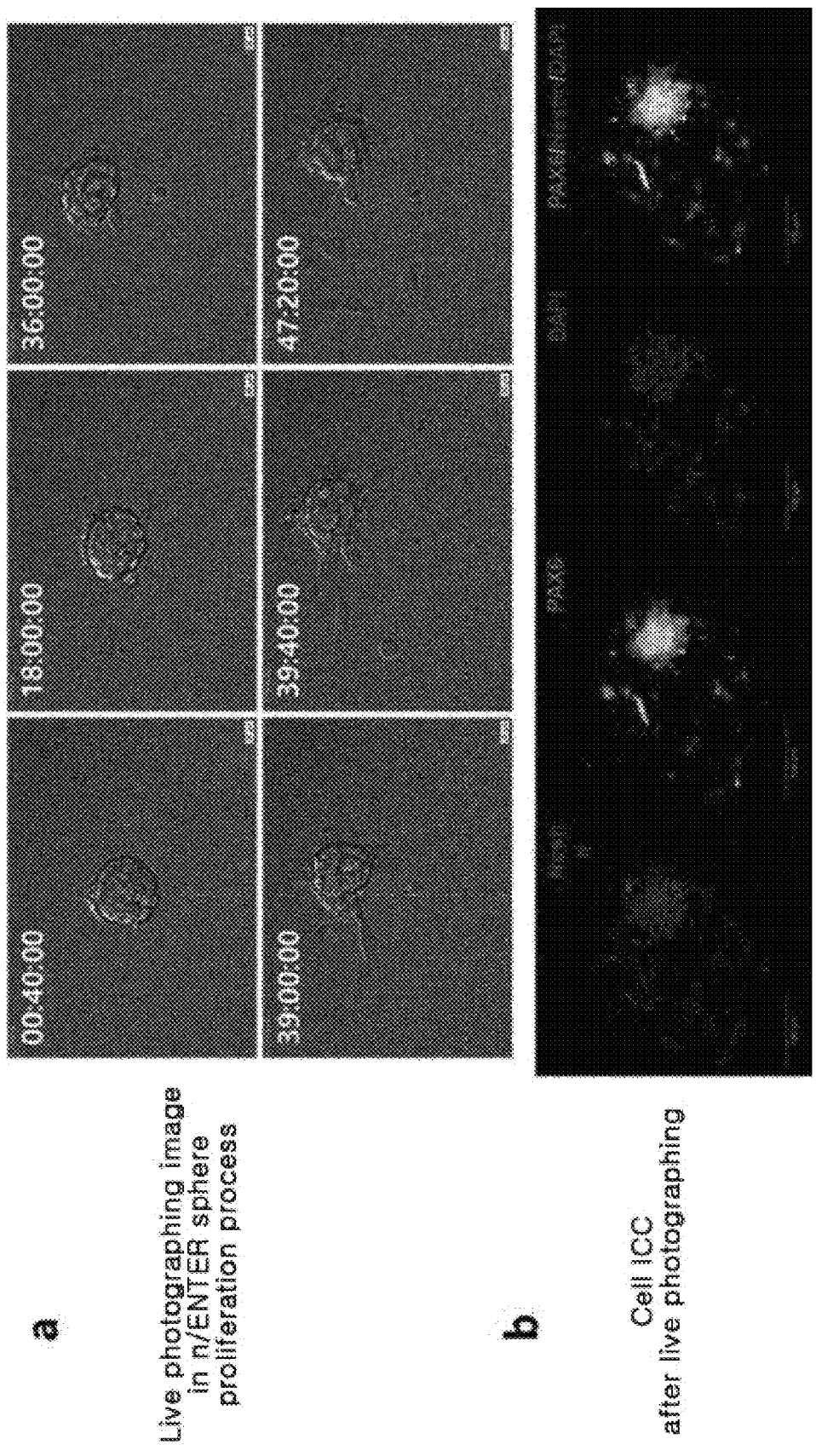
FIG. 13 shows (A) a process of proliferating cells in a single sphere of n/ENTER cells and (B) a result of maintaining properties of a neuroprogenitor in proliferated cells.

FIG. 13 shows an experimental result of confirming self-renewal of differentiation-induced cells (n/ENTER cells), and in FIG. 13A, it was confirmed through a video that the cells proliferated from one spheroid express Pax6 and Nestin and thus it can be seen that the properties of neuroprogenitors are transmitted to the proliferated cells.

Next, differentiation-induced cells (n/ENTER cells) were injected into the brain of 5-week-old mice, and after 4 weeks, the brain was recovered and the differentiation of the injected cells into surrounding cells was confirmed, and the function of the differentiated cells was confirmed.

Figure 14:
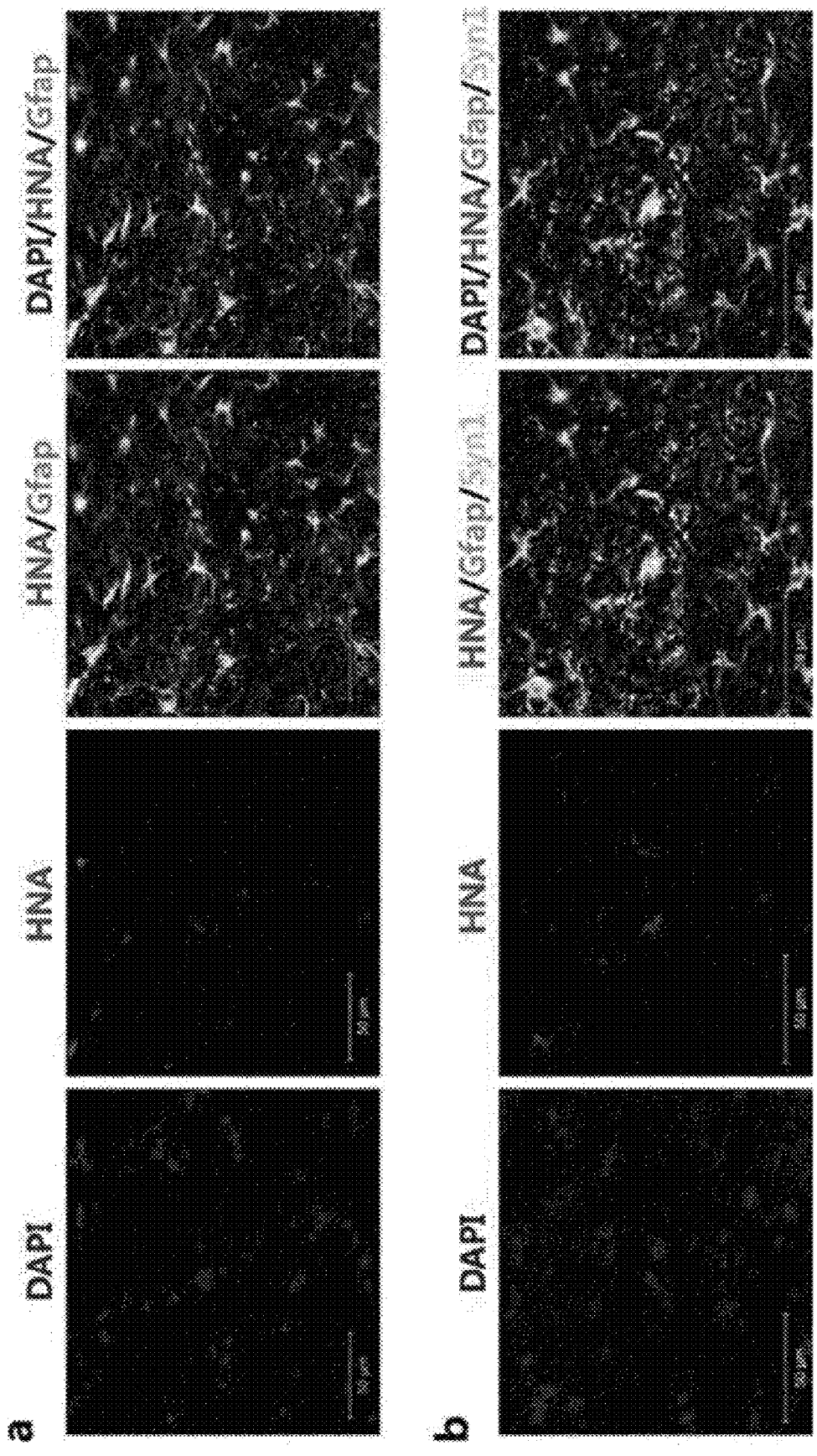
FIG. 14 shows results of differentiation after transplanting n/ENTER cells into the brain of a mouse, in which (A) shows expressions of an astrocyte marker (Gfap) in transplanted cells (HNA-stained cells) and (B) shows secretion of synapsin (Syn1) in differentiated cells after transplantation.

As shown in FIG. 14A, when the cells injected into the brain (n/ENTER cells) were stained with a human nuclear antigen (HNA) and marked, and the marked cells were stained with a Gfap antibody, it was confirmed that Gfap was expressed in the injected cells.

In order to confirm whether the cells expressing Gfap have a normal function, the cells were stained with a synapsin 1 antibody (1:500, R&D system) to confirm whether synapsin was secreted. As a result, the expression of synapsin 1 was observed in the cells expressing Gfap among the cells expressing HNA (FIG. 14B).

Next, the expression of neuroprogenitor markers (Oct4, Sox2, Pax6, and Nestin) in the spheroid generated on day 3 after induction of differentiation was confirmed by immunocytochemical staining.

To this end, the spheroid and attached cells were immobilized in 4% paraformaldehyde for 10 minutes and embedded in PBS containing 0.1% Triton X-100 for 40 minutes. The cells were blocked with a PBS containing 5% (v/v) goat serum for 1 hour and Oct4 (1:200), Sox2 (1:200), Pax6 (1:200), Nestin (1:200, Cell Signaling Technology), and the like were stained with a primary antibody overnight at 4° C. The cells were washed with a PBS buffer containing 0.03% Triton X-100, stained with secondary antibodies, Alexa-488 or -594 binding anti-rabbit, and anti-mouse antibodies (1:1000, Thermo, excitation/emission, 495/519 nm, excitation/emission, 590/617 nm) at room temperature for about 1 hour and 30 minutes, washed with a PBS buffer containing 0.03% Triton X-100, and then mounted on a mounting sol containing DAPI (Vector Laboratories, Inc., Burlingame, CA, excitation/emission, 420/480 nm), and images were analyzed with a confocal laser fluorescence microscope (LSM 700; Carl Zeiss).

Figure 15:
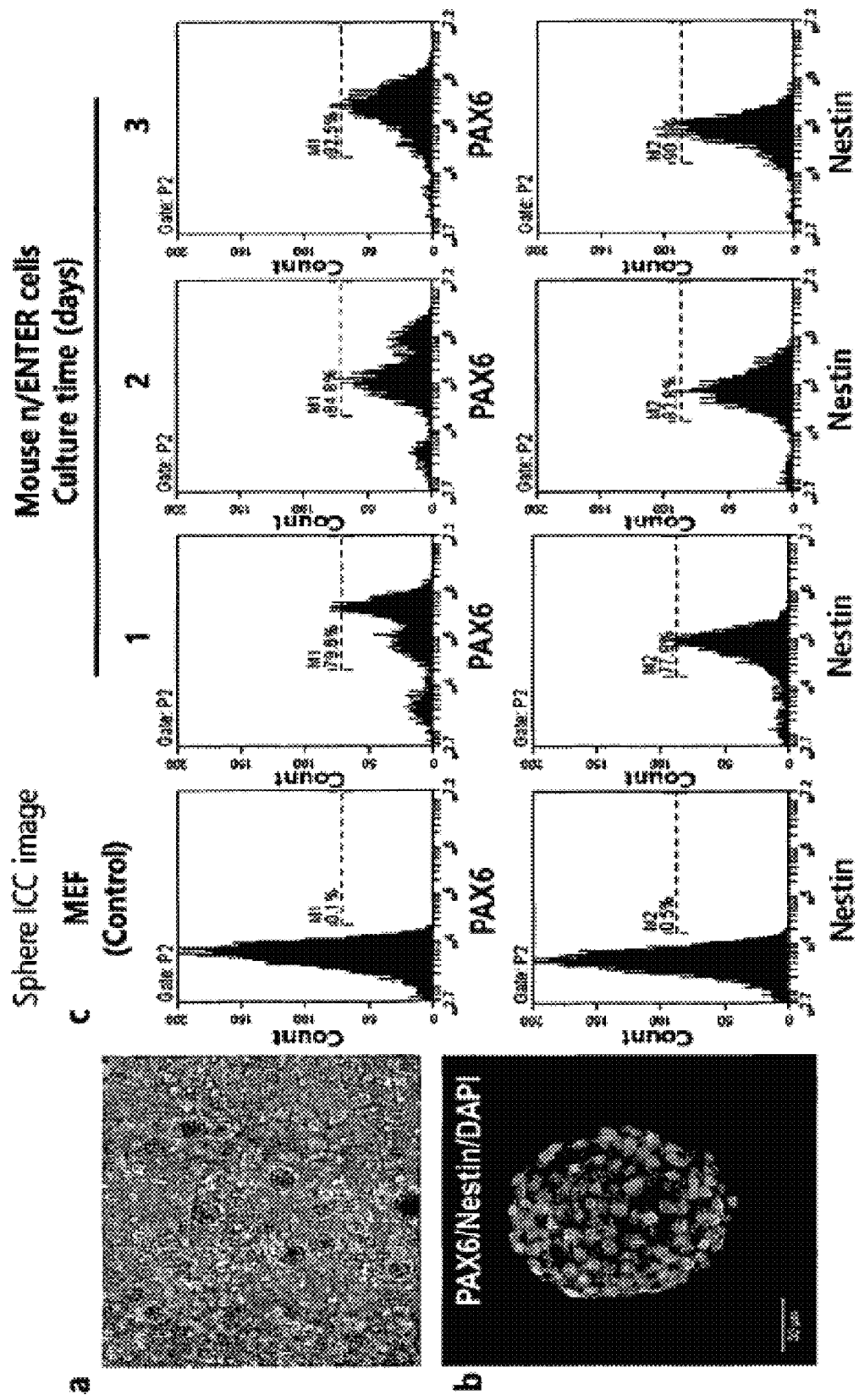
FIG. 15 shows results of differentiation of MEF into neuroprogenitors by a neural stem cell differentiation-inducing medium and ultrasonic wave stimulation, in which (A) shows a result of analyzing a change in cell morphology, (B) shows a result of analyzing expressions of a neuroprogenitor marker of a sphere, and (C) shows a result of analyzing expressions of a neuroprogenitor marker using flow cytometry.

In FIG. 15A, the spheroid formation was confirmed and the expression of neuroprogenitor makers Pax6 and Nestin was highly expressed in spheroid (FIG. 15B).

FIG. 15C shows a result of analyzing an expression pattern of Pax6/Nestin in the cells differentiation-induced for 3 days after induction of differentiation through flow cytometry, in which the expression of Pax6 and Nestin was relatively 70% or more on day 1 after the treatment, and the expression of Pax6 and Nestin was the highest on day 3.

Figure 16:
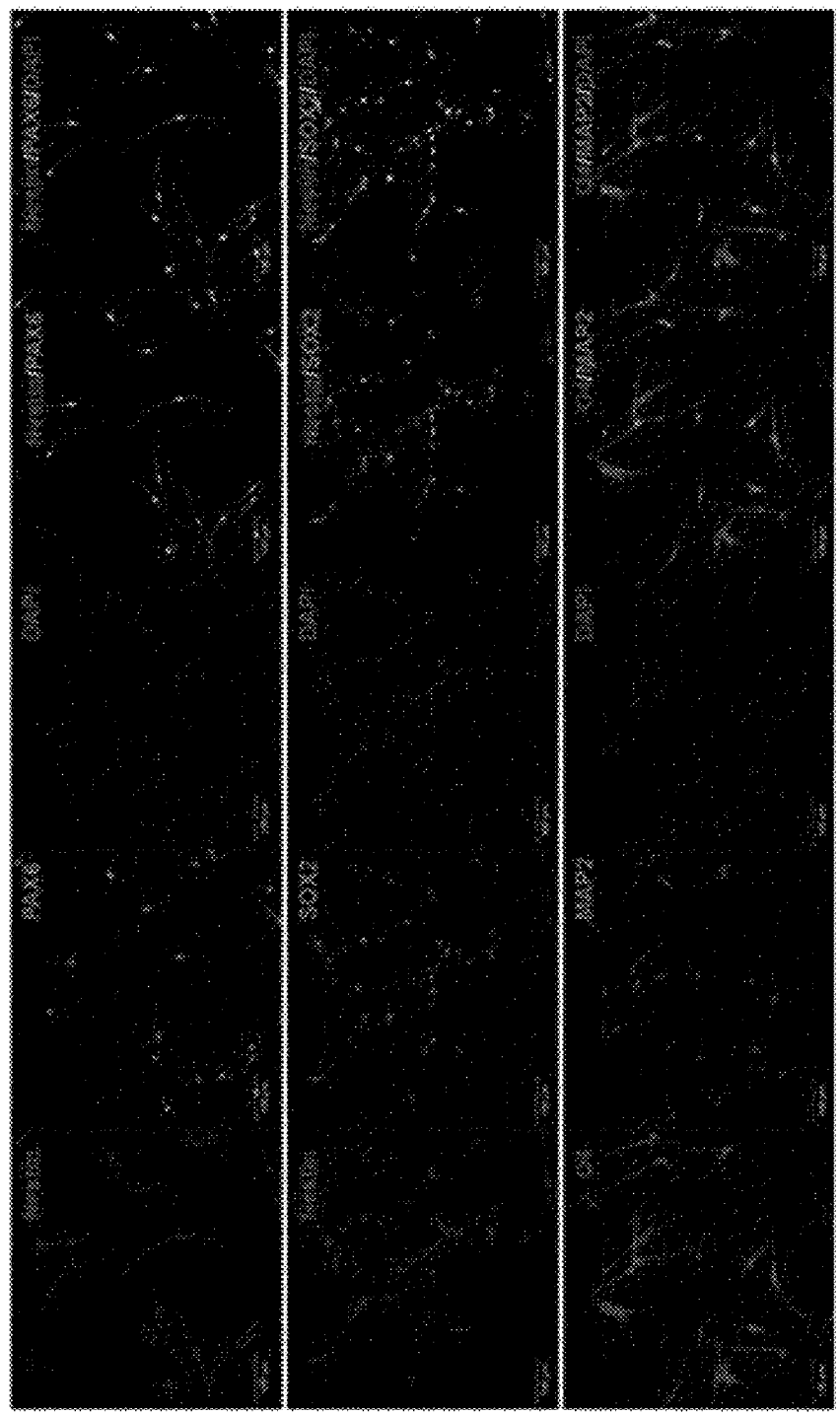
FIG. 16 shows a result of analyzing expression of differentiation markers of neuroprogenitors (mouse n/ENTER cells) differentiation-induced from MEF.

FIG. 16 shows a result of confirming that the expression of neuroprogenitor markers (Sox2, Pax6 and Nestin) is confirmed in cells after 20 days after induction of differentiation by immunocytochemical staining, in which the top and middle photographs show that the expression of Sox2, Pax6 and Nestin is high and the bottom photograph shows the same expression pattern as above as a result of confirming expression of an oligodendrocyte marker.

This result indicates that differentiation-induced cells have differentiation potency similar to neuroprogenitor differentiation potency.

<Example 9> Direct Hepatocyte Differentiation

Figure 17:
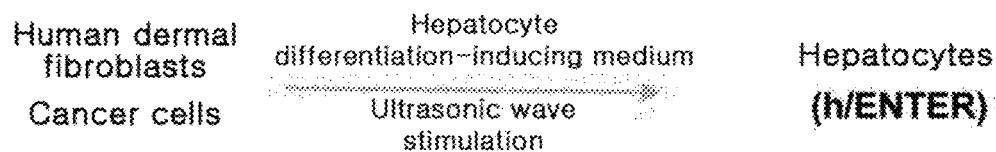
FIG. 17 is a schematic diagram showing direct differentiation of hepatocytes.

Like the schematic diagram of FIG. 17, HDF cells, HeLa cells, and Hep3B cells were collected into $1 \times 10^6$ cells in a 1 mL differentiation-inducing medium, treated with ultrasonic waves at an intensity of 1 W/cm$^2$ for 5 seconds, divided into $2 \times 10^5$ in a 35 mm Laminin coating culture dish, treated with ultrasonic waves at an intensity of 10 W/cm$^2$ for 10 minutes, and then cultured in a 2 mL hepatocyte differentiation-inducing medium. Differentiation-induced cells using a hepatocyte differentiation-inducing medium were named as h/ENTER.

Figure 18:
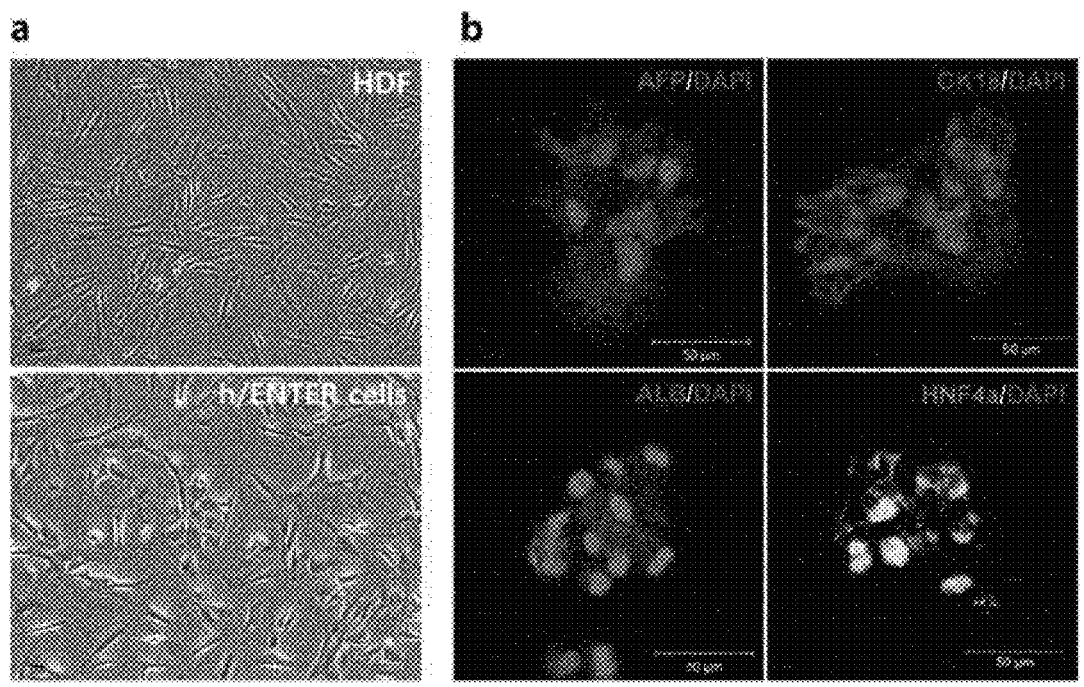
FIG. 18 shows results of differentiation of HDF treated with a hepatocyte differentiation-inducing medium and ultrasonic waves into hepatocytes, in which (A) shows a change in cell morphology and (B) shows expressions of a hepatocyte marker.

FIG. 18 induced differentiation of HDF treated with a hepatocyte differentiation-inducing medium and ultrasonic waves into hepatocytes (h/ENTER). FIG. 18 shows a change in cell appearance after 20 days of induction of HDF differentiation, and as a result of confirming hepatocyte markers (AFP, HNF4a, CK18, and ALB) after 20 days of induction of HDF differentiation through immunocytochemistry, the expression of the hepatocyte markers was confirmed in the h/ENTER cells.

Next, differentiation of HeLa cells treated with a hepatocyte differentiation-inducing medium and ultrasonic waves into hepatocytes (HeLa h/ENTER) was induced. A change in cell (HeLa h/ENTER) appearance after 19 days of the induction of HeLa cell differentiation, and hepatocyte markers (ALB, HNF4a, CYP3A4F, CYP3A7F, AIAT, SOX7, and GATA6) were confirmed through (HeLa h/ENTER) qPCR after 20 days of the induction of HeLa cell differentiation.

Figure 19:
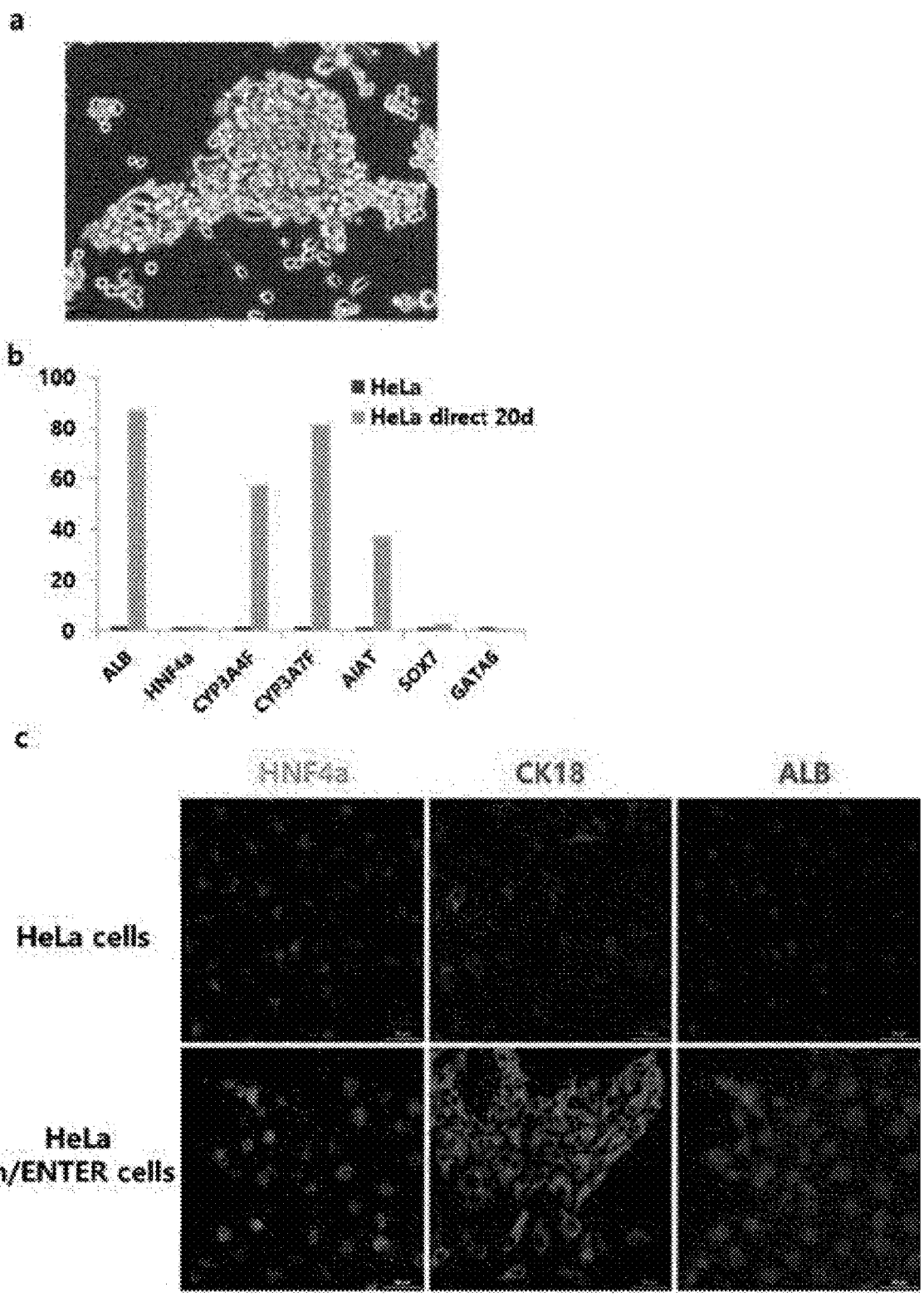
FIG. 19 shows results of differentiation of HeLa cells treated with a hepatocyte differentiation-inducing medium and ultrasonic waves into hepatocytes (HeLa h/ENTER), in which (A) shows a change in cell morphology, (B) shows a result of expressions of a hepatocyte marker using qPCR, and (C) shows a result of expressions of a hepatocyte marker using immunocytochemistry.

As shown in FIG. 19A, it was confirmed that most of hepatocyte markers were increased in differentiation-induced HeLa cells compared to HeLa cells.

In addition, hepatocyte markers (HNF4a, CK18, and ALB) were confirmed by immunocytochemistry after 3 weeks of the induction of HeLa cell differentiation, and as a result, it was confirmed that the expression of the hepatocyte markers was increased in differentiated HeLa cells (HeLa h/ENTER) compared with the HeLa cells (FIG. 19B).

The hepatocyte markers (HNF4a, CK18, and ALB) were confirmed by immunocytochemistry after 3 weeks of the induction of HeLa cell differentiation, and as a result, it was confirmed that the expression of the hepatocyte markers was increased in differentiated HeLa cells (HeLa h/ENTER) compared with the HeLa cells (FIG. 19C).

Next, differentiation of Hep3B cells treated with a hepatocyte differentiation-inducing medium and ultrasonic waves into hepatocytes (Hep3B h/ENTER cell) was induced. A change in cell appearance after 19 days of induction of Hep3B cell differentiation is shown, and expression of hepatocyte markers (HNF4a, CK18, and ALB) after 3 weeks of induction of Hep3B cell differentiation by immunocytochemistry were confirmed.

Figure 20:
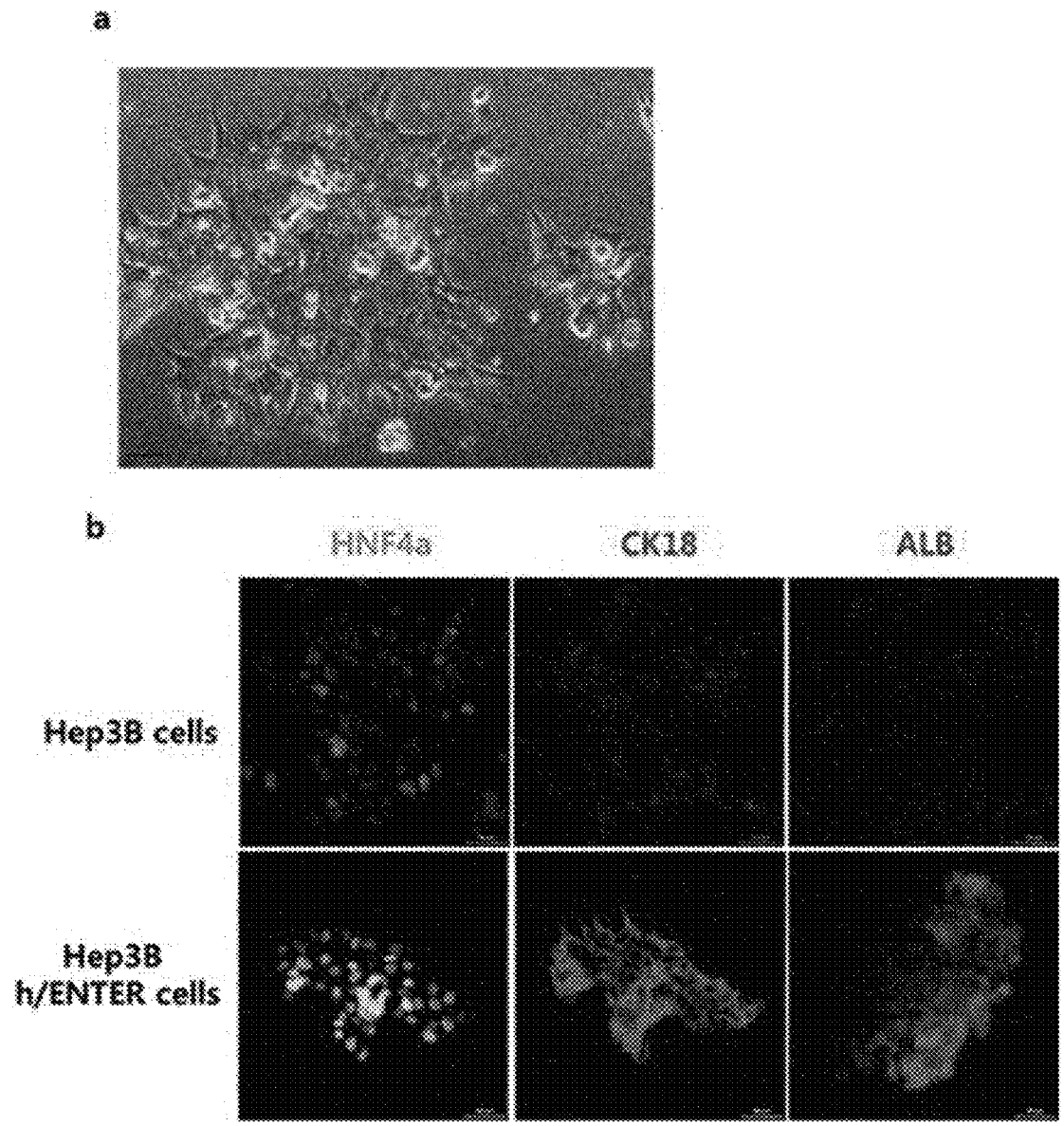
FIG. 20 shows results of differentiation of Hep3B cells treated with a hepatocyte differentiation-inducing medium and ultrasonic waves into hepatocytes (Hep3B h/ENTER cells), in which (A) shows a change in cell morphology and (B) shows expressions of a hepatocyte marker.

As shown in FIG. 20B, it was confirmed that the expression of the hepatocyte markers was increased in the differentiated Hep3B cells (Hep3B h/ENTER) compared with the Hep3B cells.

Figure 21:
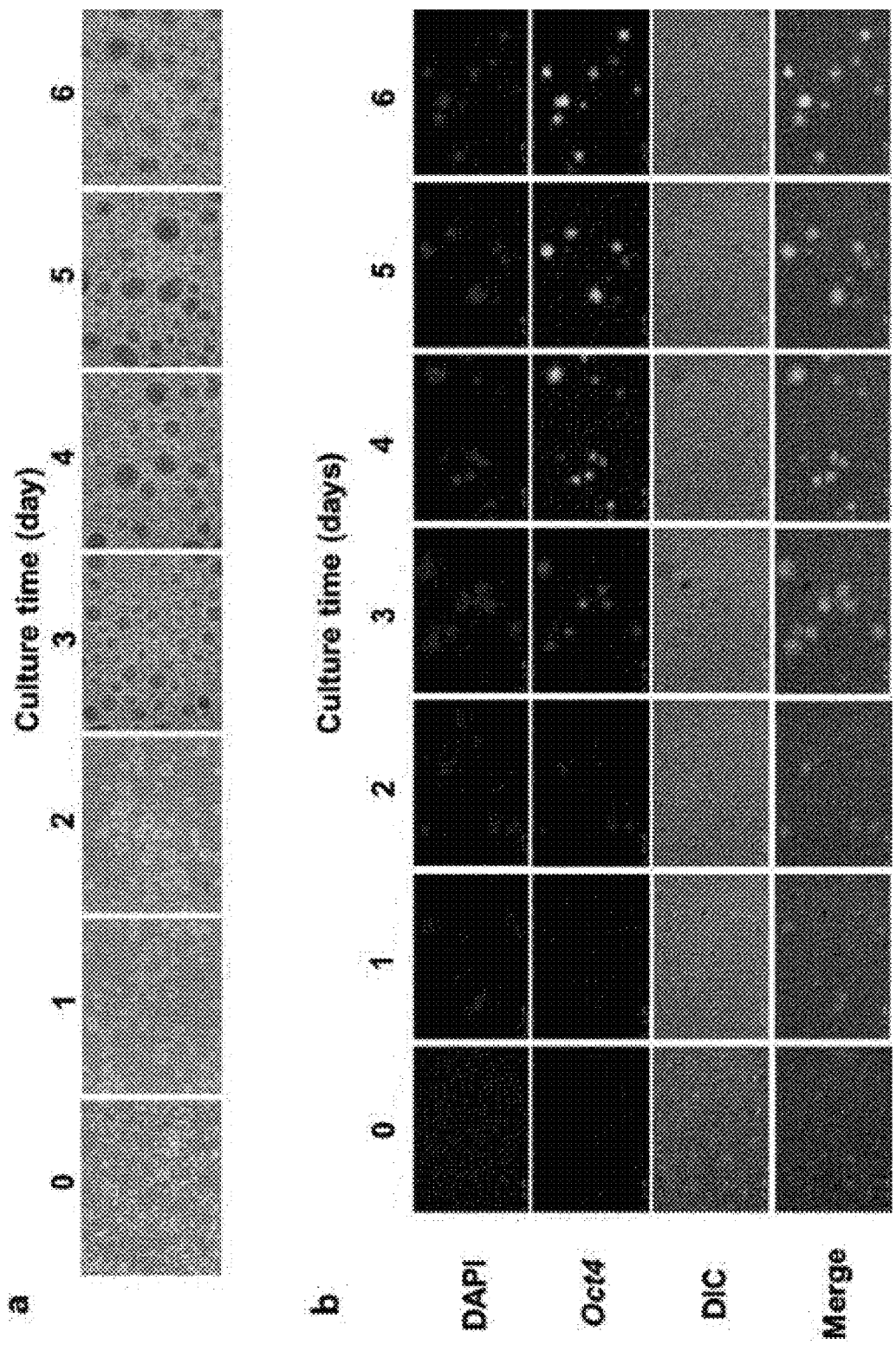
FIG. 21 shows results of differentiation of HDF cells treated with a human ES culture medium and ultrasonic waves into es/ENTER cells, in which (A) shows a change in cell morphology and (B) shows a change of Oct4 expressions according to a culture time.
Figure 22:
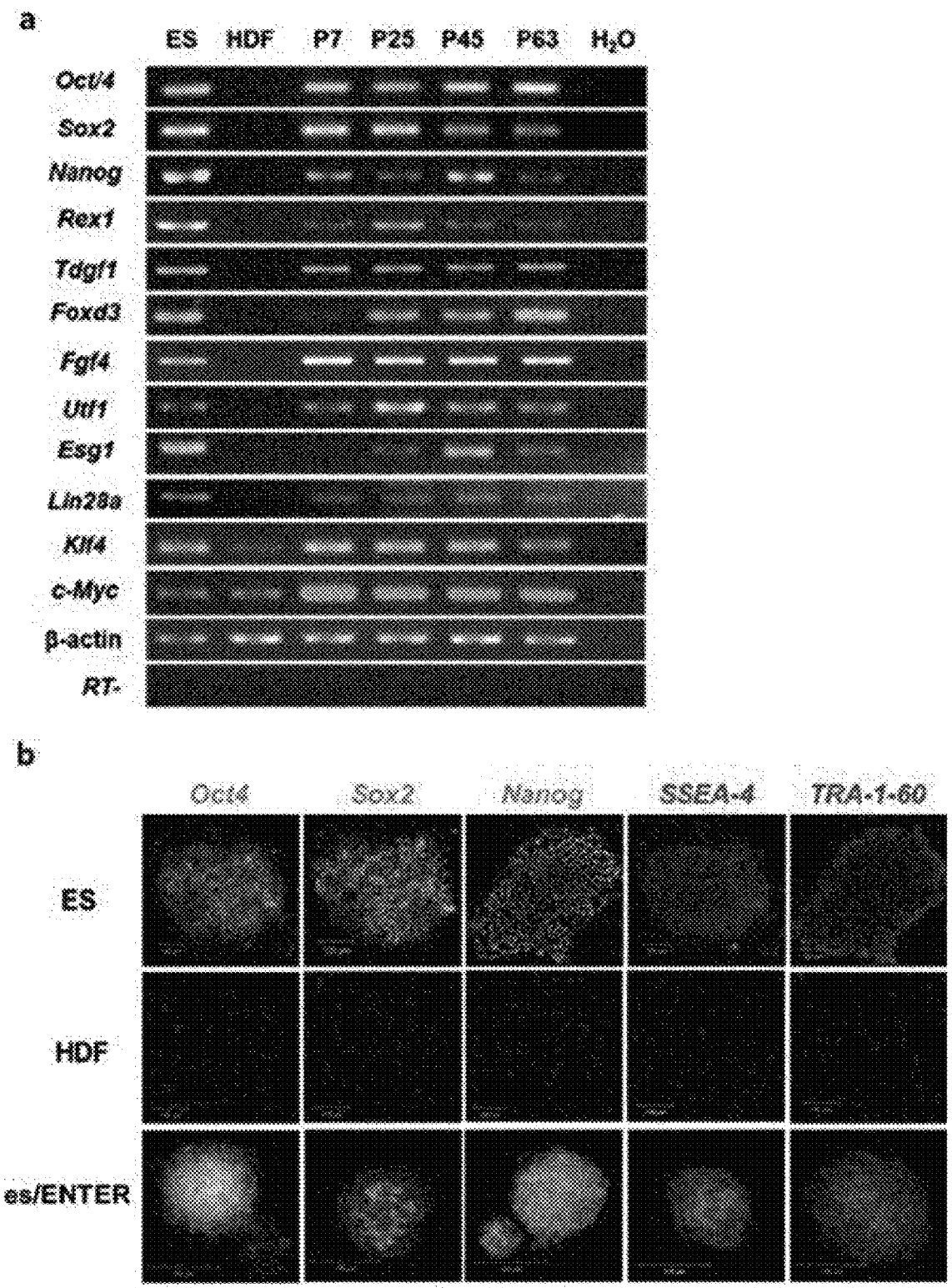
FIG. 22 shows expressions of (A) a pluripotent marker gene and (B) a protein in es/ENTER cells.

Next, differentiation of HDF cells treated with a human ES culture medium and ultrasonic waves into es/ENTER cells was induced. FIG. 21A shows a change of cell morphology according to a culture time, and FIG. 21B shows a result of having a difference in Oct4 expression according to a culture time, in which spheroid was formed on day 1 after induction of differentiation by the human ES medium, and expression of a pluripotent marker, Oct4, was increased according to a culture time.

Spheroids formed after culturing for 6 days were recovered and the expression of the pluripotent marker was confirmed by RT-PCR and ICC. As a result, in the es/ENTER cells, expression of a (A) pluripotent marker gene and (B) protein was confirmed.

Figure 23:
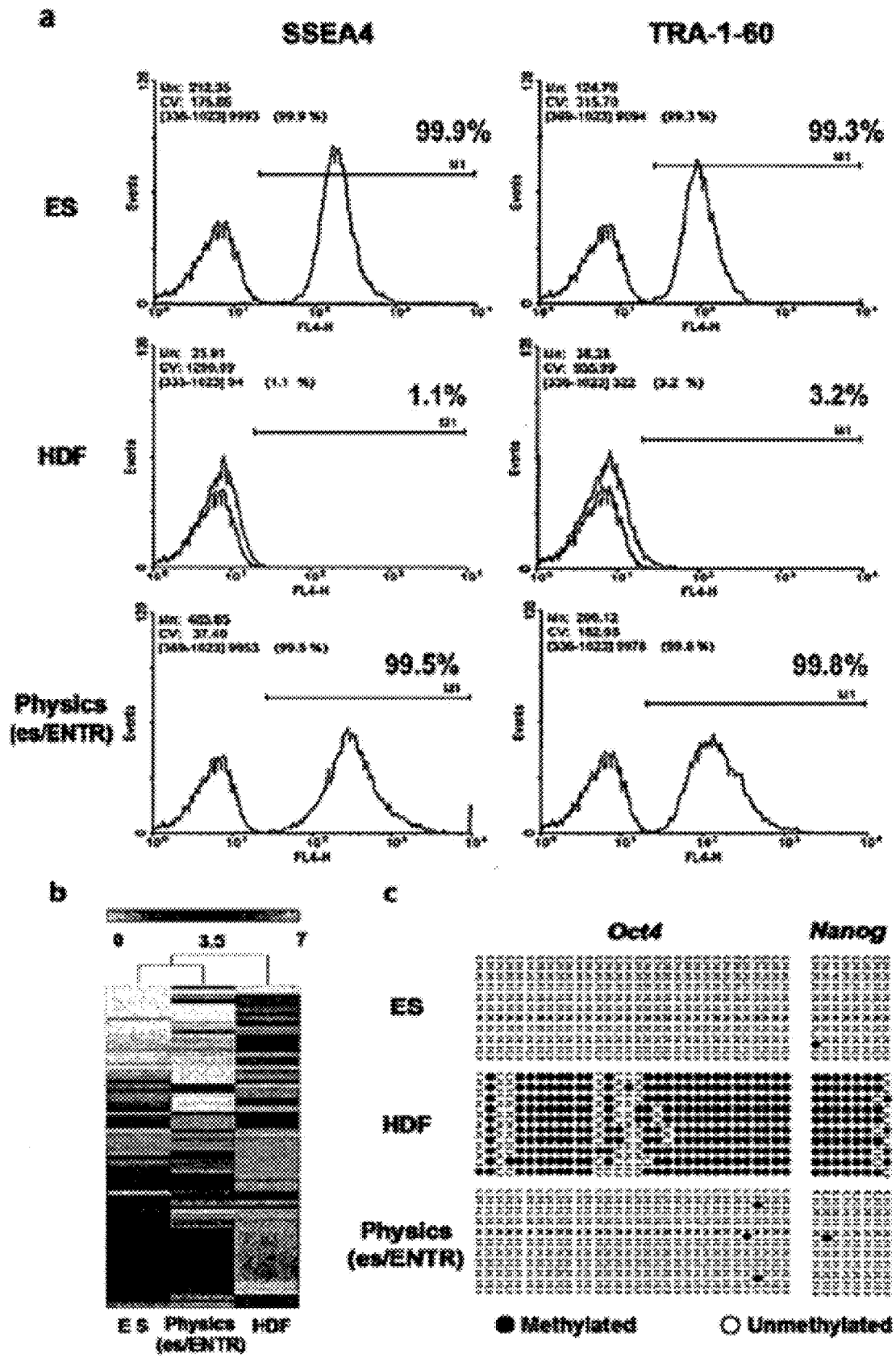
FIG. 23 shows results of analyzing pluripotent properties in es/ENTER cells, in which (A) shows a result of analyzing a pluripotent marker using flow cytometry, (B) shows a result of analyzing a pluripotent gene expression pattern using microarray, and (C) shows a result of analyzing methylation of Oct4 and Nanog promoters using bisulfite sequencing.

As a result of analyzing a pluripotent property in the es/ENTER cells, expression of SSEA4 and TRA-1-60 of es/ENTER cells was confirmed using flow cytometry (FIG. 23A), and as a result of analyzing a pattern of pluripotent gene expression by a microarray (affymetrix chip), a pattern similar to the ES cells instead of HDF was shown (FIG. 23B). In addition, as a result of confirming whether methylation of a promoter region at which the synthesis in a DNA gene expressed by bisulfate sequencing starts is loosened, it was confirmed that important pluripotent genes Oct4 and Nanog were opened. From these results, it can be seen that es/ENTER differentiation-induced by the human ES medium has pluripotent properties (FIG. 23C).

TABLE 4

List of bisulfite sequencing primers for methylation analysis

| Gene code | | Primer sequence (5'-3') Forward | Backward | Annealing temperature (° C.) |
|---|---|---|---|---|
| Oct4 | | CCAGGTTCAATGGATTCTC C (SEQ ID NO: 18) | GTATCCGACCAGGGTTAG GG (SEQ ID NO: 82) | 58 |
| Nanog | | TTCTCTCCTCCTCCCTCTC C (SEQ ID NO: 19) | CTCCCAAAATGCTGGGAT TA (SEQ ID NO: 83) | 56 |
| Tdgf1 | 1 | GTGGGTCCTCTTCAGTGC AT (SEQ ID NO: 20) | GCTGCTGGAGAGGTGCTT AG (SEQ ID NO: 84) | 60 |
| | 2 | GACCCTCGCCTTATCCTTT C (SEQ ID NO: 21) | CACTGCCCTACTGCTTGG TT (SEQ ID NO: 85) | 60 |
| | 3 | GCACAGAGGGTGTCCATC TT (SEQ ID NO: 22) | CTGCCCCTCTCACTCATCT C (SEQ ID NO: 86) | 60 |
| Afp | | CAGTCCAGCAACAAGCCT TT (SEQ ID NO: 23) | ACTGGAGTCACTGGGAGG AA (SEQ ID NO: 87) | 58 |
| Gata4 | | TAGGATGCCTGCTGGATTT C (SEQ ID NO: 24) | CATTCATTCGCCCTCTCTT C (SEQ ID NO: 88) | 58 |
| Acta2 | | GGAGCACTTGAGAAGCA AAGA (SEQ ID NO: 25) | CTCAGGAAAGCCTCCCTC TT (SEQ ID NO: 89) | 60 |
| Msx1 | | GTAGACGCGGTTTGTGGA AC (SEQ ID NO: 26) | TTGGGGCTCTGTTTTTAAC G (SEQ ID NO: 90) | 60 |
| Pax6 | | GTTGCAGCTGGTGTGTTG AC (SEQ ID NO: 27) | GCATTGTTGTGAATGCTGC T (SEQ ID NO: 91) | 60 |
| Nestin | | GGGTCAAGTGGACTTTCC TG (SEQ ID NO: 28) | CACCCTCCTTGTCACTCCT C (SEQ ID NO: 92) | 60 |

Figure 24:
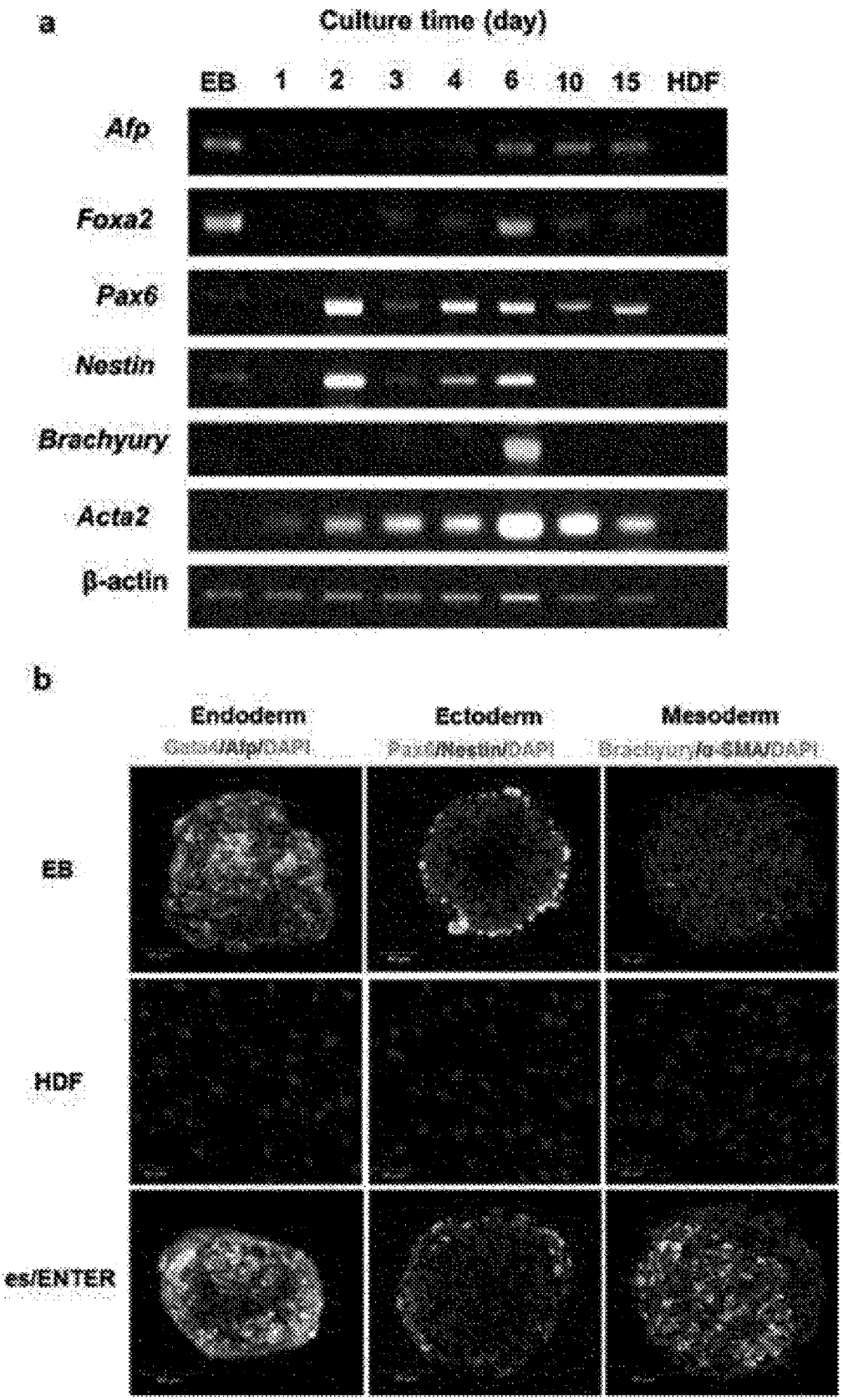
FIG. 24 shows expression of (A) a triploblastic marker gene and (B) a protein in es/ENTER cells.
Figure 25:
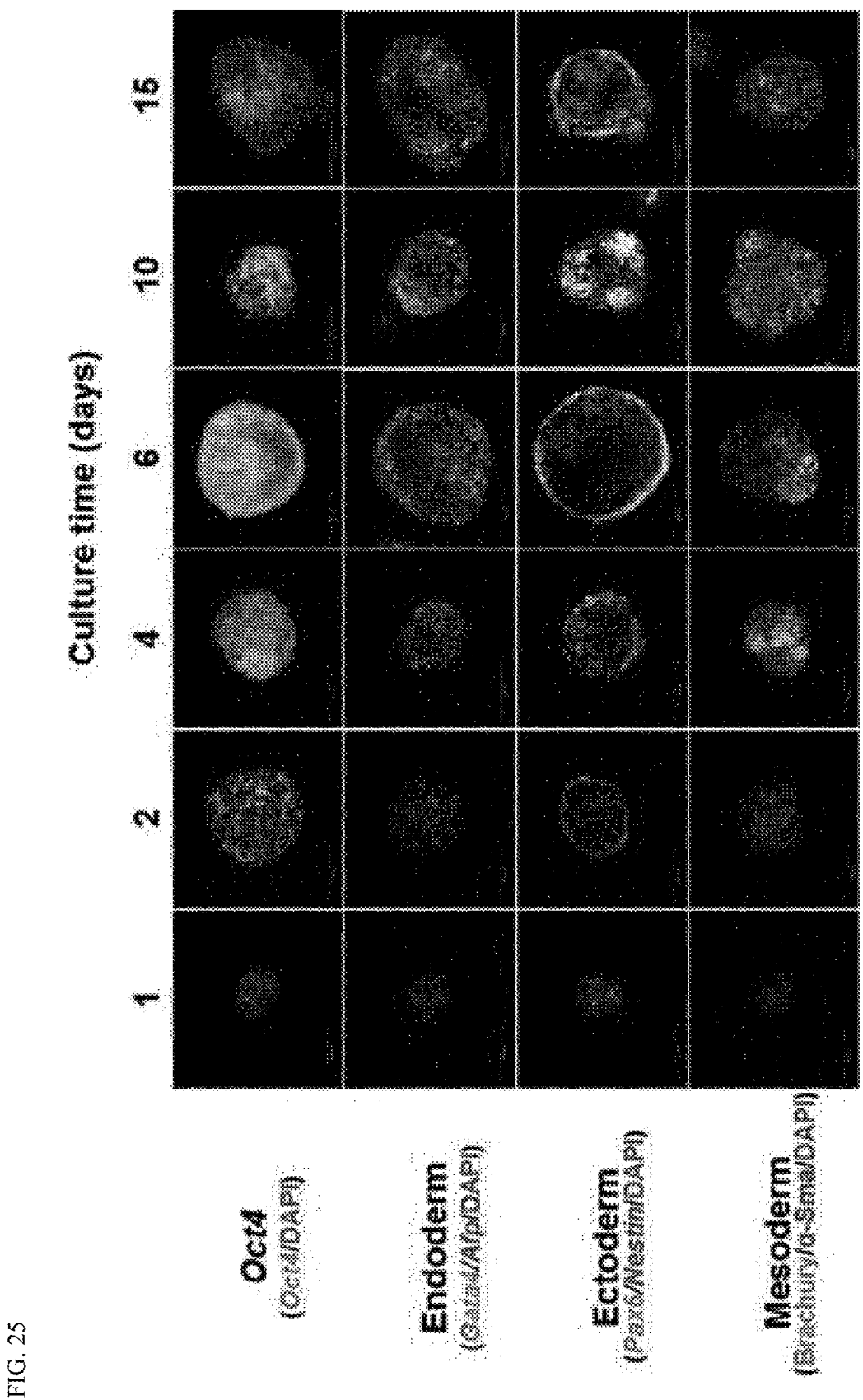
FIG. 25 shows a change in expressions of Oct4 and a triploblastic marker in es/ENTER cells for each culture time.
Figure 26:
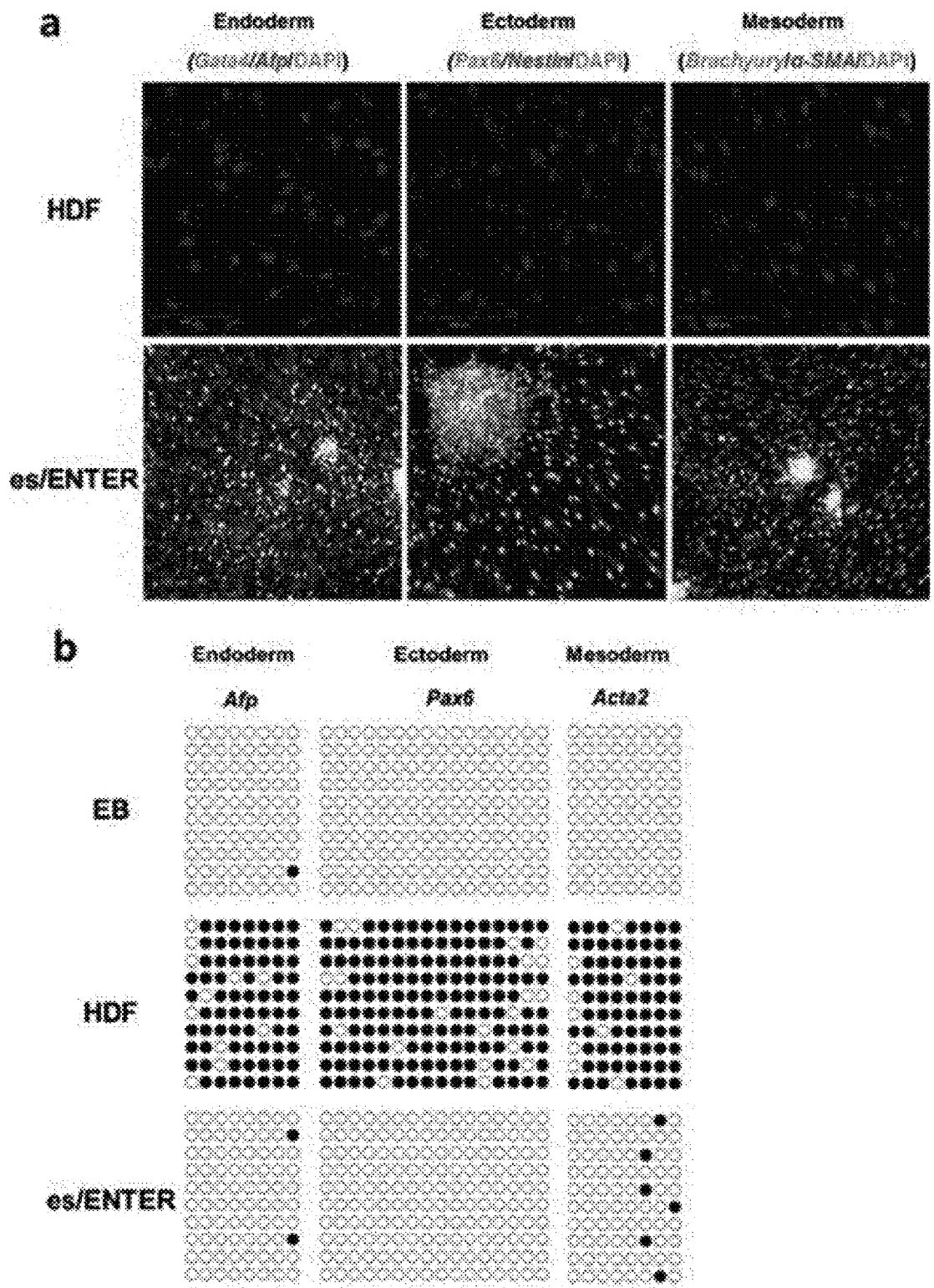
FIG. 26 shows expressions (A) of a triploblastic marker protein in monolayer-cultured es/ENTER cells and an analysis result (B) of methylation of triploblastic marker DNA in es/ENTER cells using bisulfite sequencing.

Next, the differentiation marker was confirmed in the es/ENTER cells. FIG. 24 shows (A) expression of a triploblastic marker gene and (B) expression of proteins in the es/ENTER cells, FIG. 25 shows a change in expression of Oct4 and the triploblastic marker gene in the es/ENTER cells for each culture time, and FIG. 26 shows (A) expression of a triploblastic marker protein in the monolayer-cultured es/ENTER cells and (B) a result of triploblastic marker DNA methylation analysis of es/ENTER cells using bisulfate sequencing.

TABLE 5

PCR primer list of differentiation marker genes

| | Gene code | Primer sequence (5'-3') | | Annealing temperature (° C.) |
|---|---|---|---|---|
| Endoderm | Afp | AGCAGCTTGGTGGTGGAT GA (SEQ ID NO: 29) | CCTGAGCTTGGCACAG ATCC (SEQ ID NO: 93) | 63 |
| | Foxa2 | TTCAGGCCCGGCTAACTC TG (SEQ ID NO: 30) | CCTTGCGTCTCTGCAAC ACC (SEQ ID NO: 94) | 58 |
| | Gata6 | TGTGCGTTCATGGAGAAG ATCA (SEQ ID NO: 31) | TTTGATAAGAGACCTCA TGAACCGACT (SEQ ID NO: 95) | 60 |
| Ectoderm | Nestin | GAAACAGCCATAGAGGG CAAA (SEQ ID NO: 32) | TGGTTTTCCAGAGTCTT CAGTGA (SEQ ID NO: 96) | 50 |
| | Pax6 | ACCCATTATCCAGATGTG TTTGCCCGAG (SEQ ID NO: 33) | ATGGTGAAGCTGGGCAT AGGCGGCAG (SEQ ID NO: 97) | 58 |
| Mesoderm, cardio-myocyte | Acta2 (a-SMA) | CTATGAGGGCTATGCCTT GCC (SEQ ID NO: 34) | GCTCAGCAGTAGTAAC GAAGGA (SEQ ID NO: 98) | 50 |
| Mesoderm | Brachyury (T) | GCCCTCTCCCTCCCCTCC ACGCACAG (SEQ ID NO: 35) | CGGCGCCGTTGCTCAC AGACCACAGG (SEQ ID NO: 99) | 66 |
| | Msx1 | CGAGAGGACCCCGTGGA TGCAGAG (SEQ ID NO: 36) | GGCGGCCATCTTCAGCT TCTCCAG (SEQ ID NO: 100) | 58 |

TABLE 5-continued

PCR primer list of differentiation marker genes

| | Gene code | Primer sequence (5'-3') | | Annealing temperature (° C.) |
|---|---|---|---|---|
| Cardio-myocyte | My17 | GGGCCCCATCAACTTCAC CGTCTTCC (SEQ ID NO: 37) | TGTAGTCGATGTTCCCC GCCAGGTCC (SEQ ID NO: 101) | 58 |
| | Nkx2-5 | CCAAGGACCCTAGAGCC GAA (SEQ ID NO: 38) | ATAGGCGGGGTAGGCG TTAT (SEQ ID NO: 102) | 50 |
| | TnTc | ATGAGCGGGAGAAGGAG CGGCAGAAC (SEQ ID NO: 39) | TCAATGGCCAGCACCTT CCTCCTCTC (SEQ ID NO: 103) | 63 |
| Neurons | Map2 | CAGGTGGCGGACGTGTG AAAATTGAGAGTG (SEQ ID NO: 40) | CACGCTGGATCTGCCTG GGGACTGTG (SEQ ID NO: 104) | 66.5 |
| | TuJ1 | GAGCGGATCAGCGTCTAC TACAA (SEQ ID NO: 41) | GATACTCCTCACGCACC TTGCT (SEQ ID NO: 105) | 52 |
| | Gfap | CCTCTCCCTGGCTCGAAT G (SEQ ID NO: 42) | GGAAGCGAACCTTCTC GATGTA (SEQ ID NO: 106) | 52 |
| | Vglut1 | CGACGACAGCCTTTTGTG GT (SEQ ID NO: 43) | GCCGAGACGTAGAAAA CAGAG (SEQ ID NO: 107) | 50 |
| | Vmat2 | CTTTGGAGTTGGTTTTGC G (SEQ ID NO: 44) | GCAGTTGTGGTCCATGA (SEQ ID NO: 108) | 43 |
| Adipocyte | Pparc2 | ATTGACCCAGAAAGCGAT TC (SEQ ID NO: 45) | CAAAGGAGTGGGAGTG GTCT (SEQ ID NO: 109) | 52.7 |
| | C/ebpa | GCAAACTCACCGCTCCAA TG (SEQ ID NO: 46) | TTAGGTTCCAAGCCCCA AGTC (SEQ ID NO: 110) | 56.7 |
| | aP2 | AACCTTAGATGGGGGTGT CCTG (SEQ ID NO: 47) | TCGTGGAAGTGACGCC TTTC (SEQ ID NO: 111) | 57.2 |
| | Fabp4 | ACTGGGCCAGGAATTTG ACG (SEQ ID NO: 48) | CTCGTGGAAGTGACGC CTT (SEQ ID NO: 112) | 55 |
| Hepatocyte | Alb | AGCTGTTATGGATGATTT CGCAG (SEQ ID NO: 49) | CCTCGGCAAAGCAGGT CTC (SEQ ID NO: 113) | 60 |
| | Cyp3a4 | GTGACTTTGCCCATTGTT TAGAAAG (SEQ ID NO: 50) | CAGGCGTGAGCCACTG TG (SEQ ID NO: 114) | 60 |
| | Cyp3a7 | GATTCTGTACGTGCATTG TGCTC (SEQ ID NO: 51) | ATTTGGTCATCTCCTCTA TATTACCAAGT (SEQ ID NO: 115) | 60 |
| | Tat | CCACACCCACACTCAGAT CCT (SEQ ID NO: 52) | ATTAGTGAGTCACTCTA GCAGCGC (SEQ ID NO: 116) | 60 |
| | A1AT | GGTCACAGAGGAGGCAC CC (SEQ ID NO: 53) | AGTCCCTTTCTCGTCGA TGGT (SEQ ID NO: 117) | 60 |
| | Sox7 | TGCCCACTTCATGCAACT CC (SEQ ID NO: 54) | AGGTACCCTGGGTCTTT GGTCA (SEQ ID NO: 118) | 60 |
| House keeping gene | beta-actin | CATGTACGTTGCTATCCA GGC (SEQ ID NO: 55) | CTCCTTAATGTCACGCA CGAT (SEQ ID NO: 119) | 50 |
| | Gapdh | ATGGGGAAGGTGAAGGT CG (SEQ ID NO: 56) | GGGTCATTGATGGCAAC AATATC (SEQ ID NO: 120) | 60 |

The expression of the triploblastic marker in es/ENTER spheroid was confirmed by RT-PCR and ICC, and such a result indicates that the es/ENTER cells have multi-differentiation properties.

Accordingly, the expression pattern of the pluripotent marker Oct4 according to a culture time was confirmed, and as a result, it was confirmed that after 6 days, the expression of Oct4 as the pluripotent property was decreased and the expression of the triploblastic marker was increased. Such a result shows that the es/ENTER cells are differentiated in the pluripotent property. As a result, it was confirmed that the cells released from the spheroid cultured for 2 days by attaching the es/ENTER spheroid expressed the triploblastic marker, and as a result of analyzing the DNA methylation of a representative triploblastic marker gene, it was confirmed that the triploblastic marker gene was opened.

Figure 27:
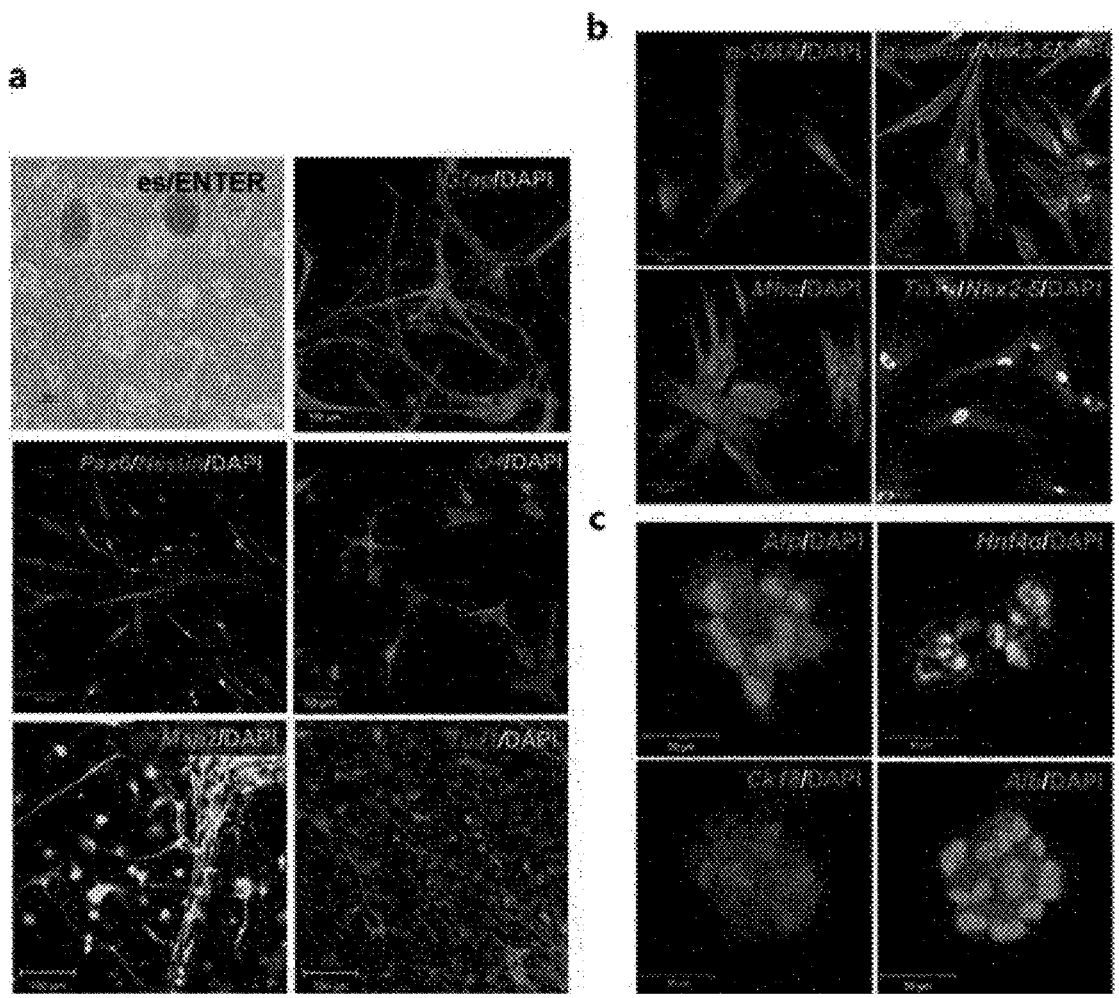
FIG. 27 shows results of in-vitro differentiation of (A) es/ENTER cells into neurons, (B) cardiomyocytes, and (C) hepatocytes.

FIG. 27 shows a result of an in-vitro differentiation experiment of es/ENTER cells into (A) neurons, (B) cardiomyocyte, and (C) hepatocytes. The es/ENTER cells were differentiation-induced using a medium differentiation-inducing into cells differentiated from each of triploblasts for 4 weeks, and as a result, the es/ENTER cells were differentiation-induced into neurons (ectoderm), cardiomyocyte (mesoderm), and hepatocytes (endoderm), and respective differentiation markers were expressed.

Figure 28:
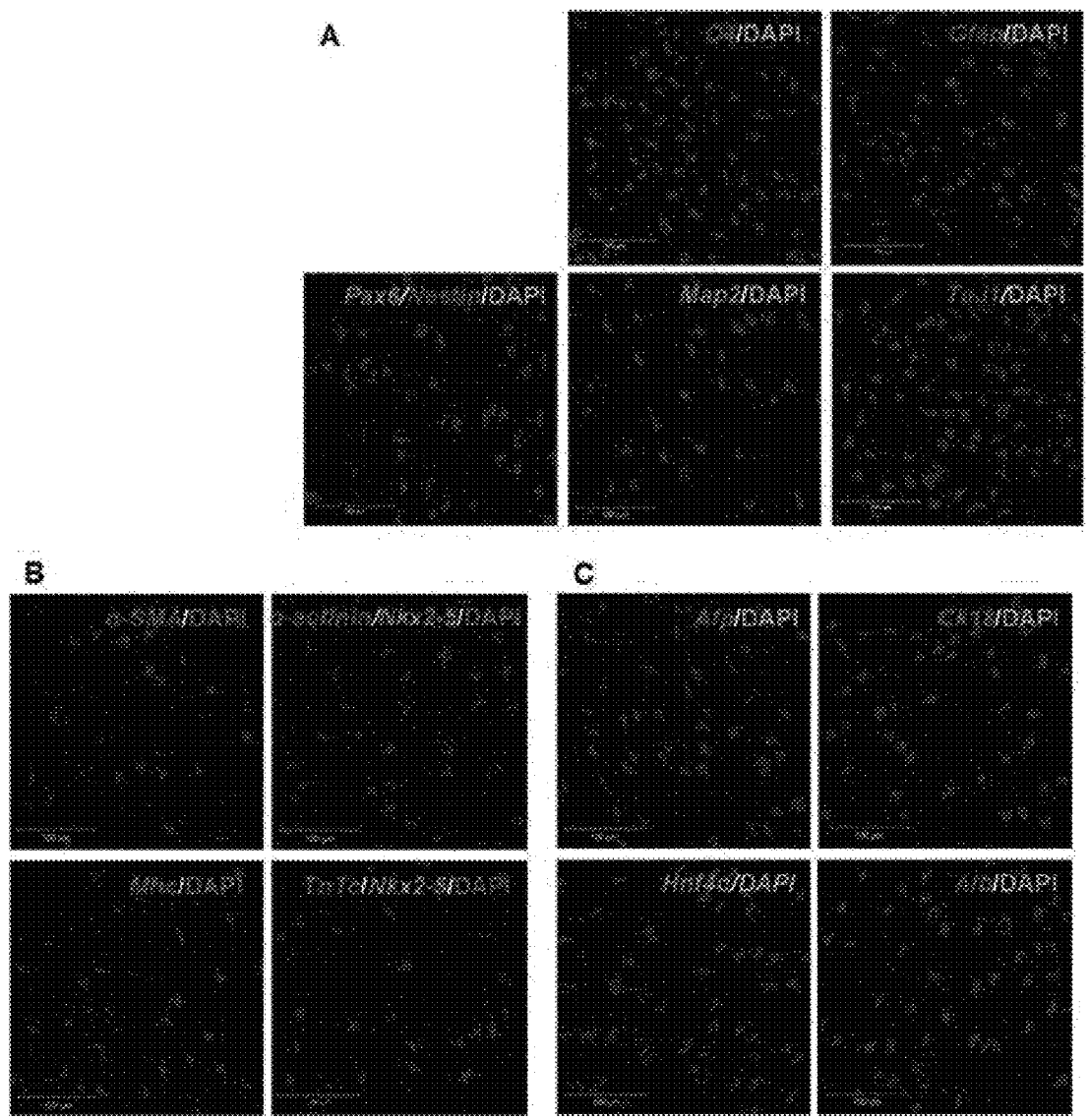
FIG. 28 shows results of analyzing expressions of (A) neuron, (B) cardiomyocyte, and (C) hepatocyte markers in HDF.

FIG. 28 shows a result of confirming expression of differentiation markers of (A) neuron, (B) cardiomyocyte, and (C) hepatocyte in HDF, and no differentiation marker was expressed in HDF.

Figure 29:
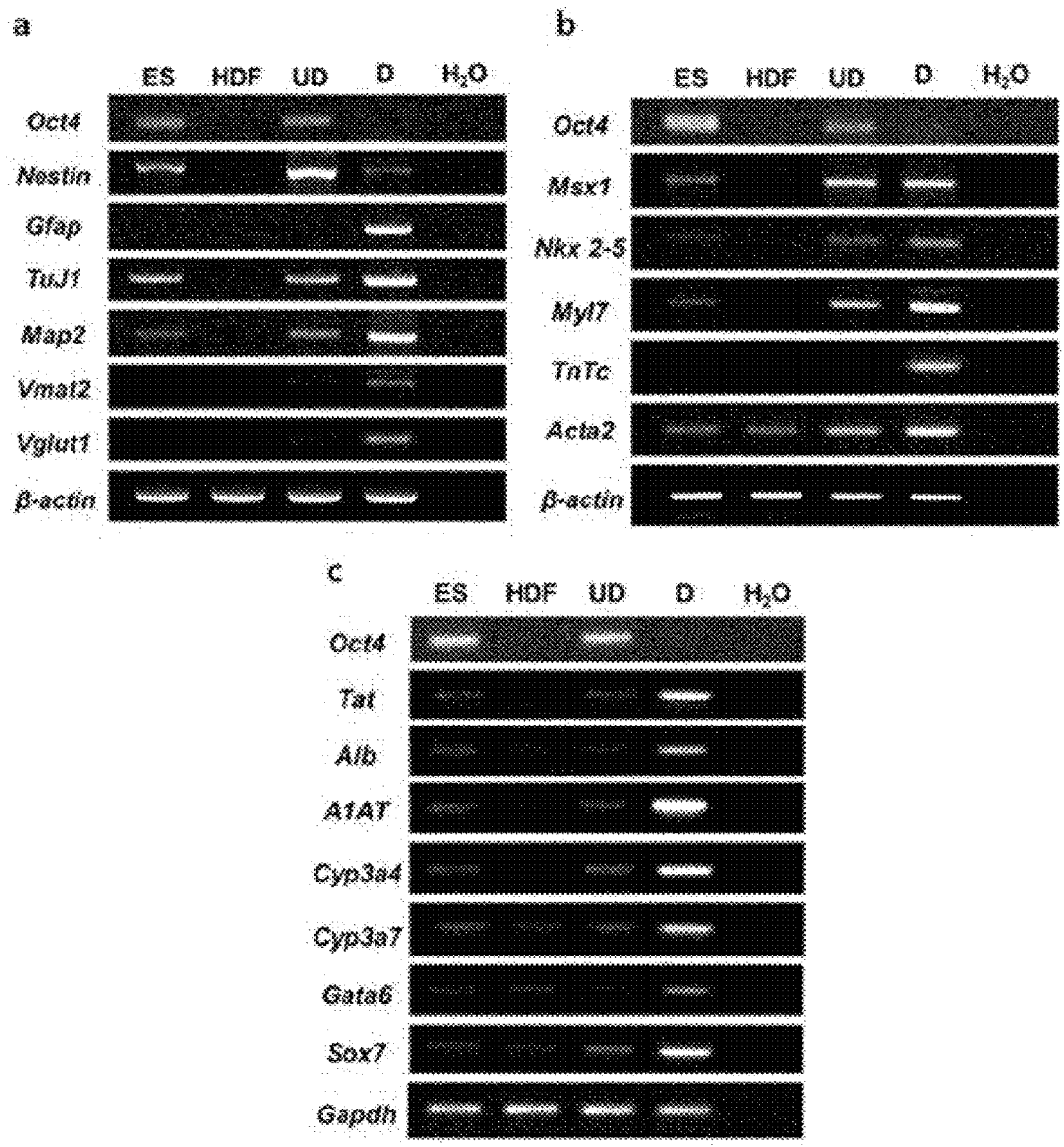
FIG. 29 shows results of RT-PCR analysis of expressions of (A) neuron, (B) cardiomyocyte, and (C) hepatocyte differentiation marker genes in differentiation-induced es/ENTER cells.

FIG. 29 shows a result of RT-PCR analysis showing the expression of differentiation marker genes of (A) neuron, (B) cardiomyocyte, and (C) hepatocyte of differentiation-induced es/ENTER cells, in which the expression of the differentiation marker genes was increased in the differentiation-induced es/ENTER. These results are results that verifies multi-differentiation ability of es/ENTER.

Figure 30:
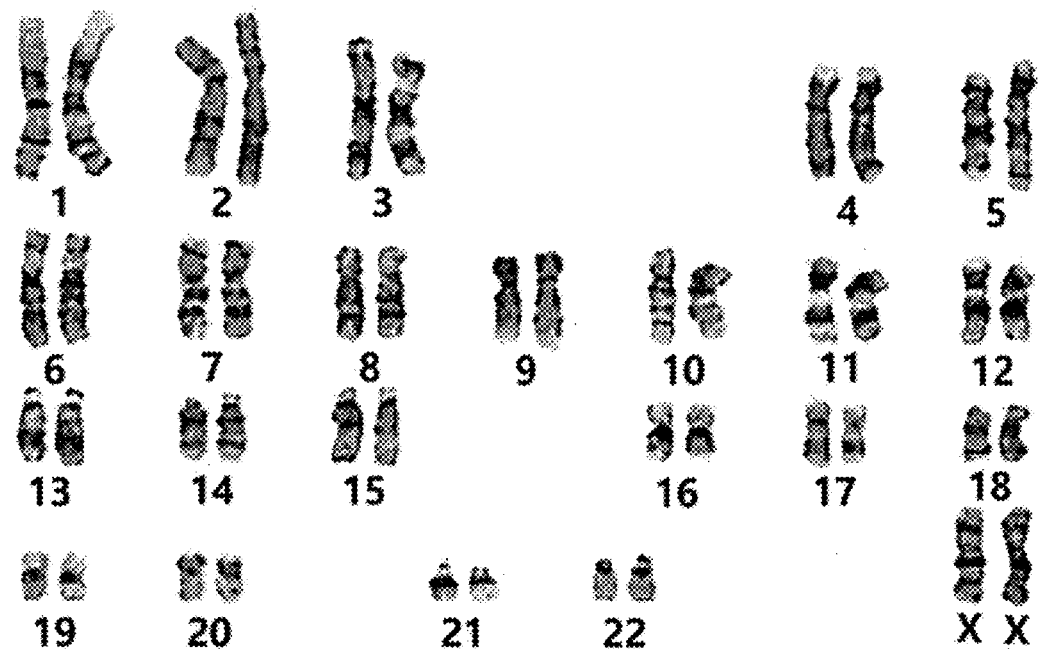
FIG. 30 shows a karyotype analysis result of es/ENTER cells by chromosome G-band analysis.

FIG. 30 shows karyotypes of the es/ENTER cells by chromosome G-band analysis, and as a result of analyzing the mutation of the cell chromosomes due to ultrasonic wave stimulation in the es/ENTER production, it was normal.

Next, es/ENTER cells were transplanted into leg muscles of 5-week-old SCID mice and after 4 weeks, the transplanted cells were confirmed using HNA.

Figure 31:
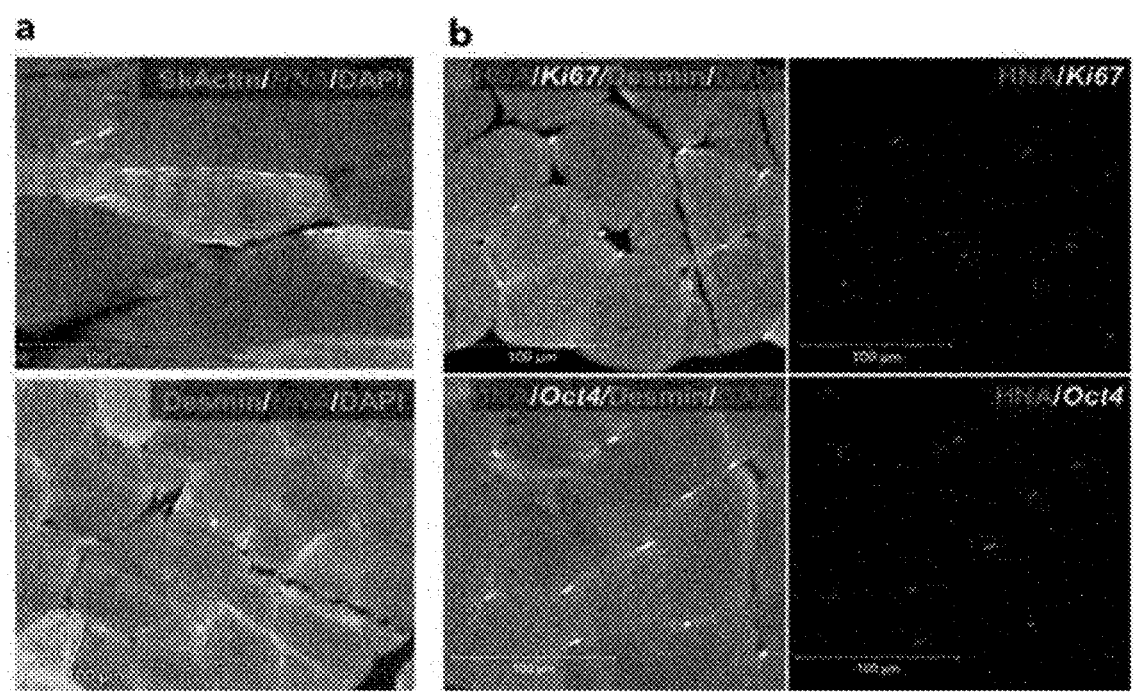
FIG. 31 shows results of muscle transplantation and in-vivo differentiation of es/ENTER cells, in which (A) shows a result of differentiation of the transplanted cells into skeletal muscle and (B) shows Oct4 expressions and proliferation (Ki67) of the transplanted cells.

As shown in FIG. 31, it was confirmed that the es/ENTER cells were differentiated into a skeletal muscle. It was also confirmed that Oct4 was not expressed and proliferated in the transplanted cells.

Next, the es/ENTER cells were transplanted into the brain of mice to confirm in vivo differentiation. To this end, the es/ENTER cells were transplanted into the brain of 5-week-old SCID mice and after 4 weeks, the transplanted cells were confirmed using HNA.

Figure 32:
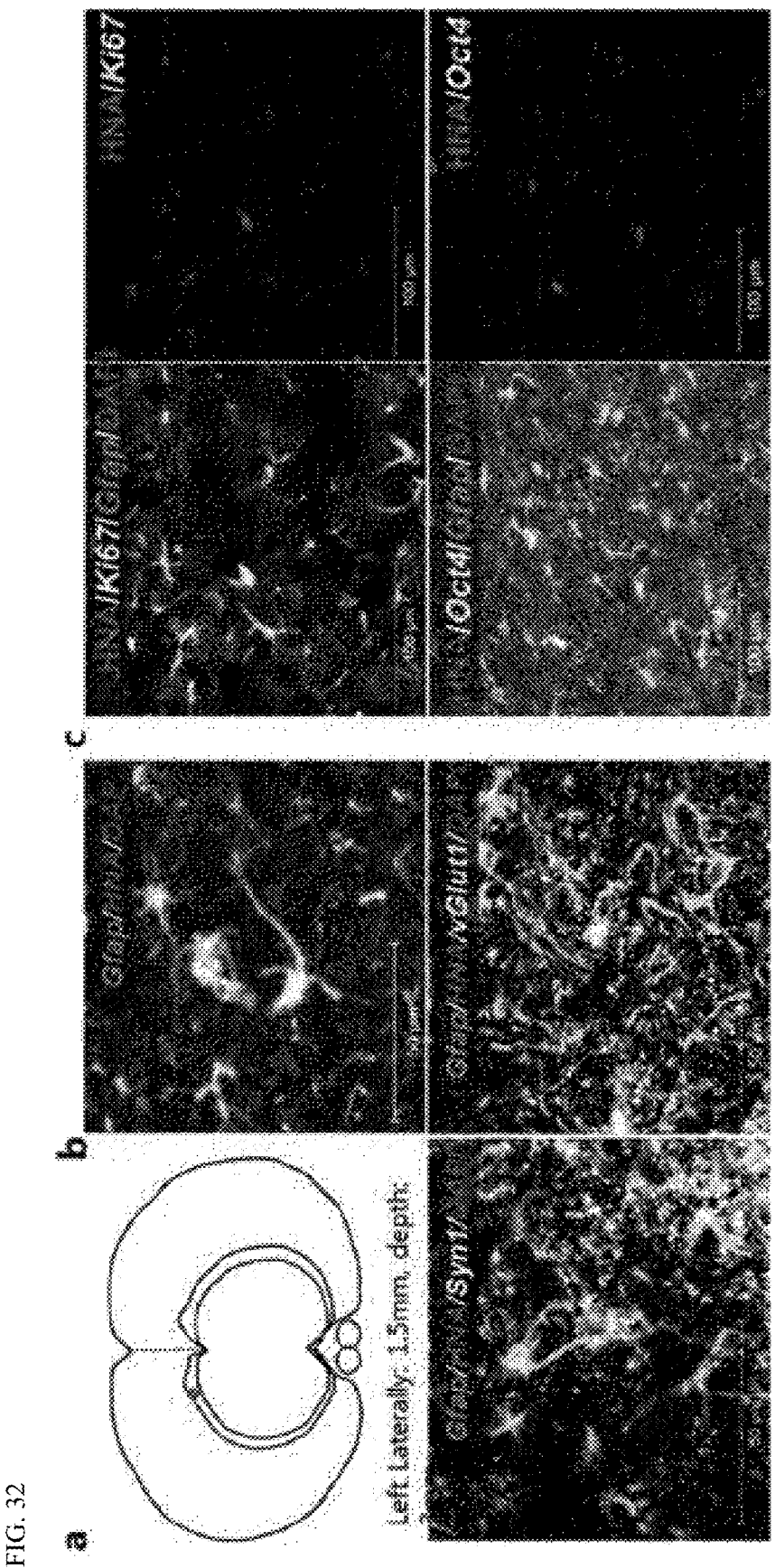
FIG. 32 shows results of transplantation of es/ENTER cells into the brain of a mouse and in-vivo differentiation thereof, in which (A) shows coordinates of transplanted cells, (B) shows secretion of an astrocyte differentiation marker (Gfap) and a neuron functional marker (synapsin, Syn1 and Vesicular Glutamate transpoter (vGlut1)) of transplanted cells, and FIG. (C) shows Oct4 expressions and proliferation (Ki67) of the transplanted cells.

As a result, it was confirmed that the es/ENTER cells were differentiated into astrocytes (Gfap) and synapsin and a vesicular glutamate transpoter were secreted. This indicates that the transplanted cells are normally differentiated and perform functions. In addition, it was confirmed that Oct4 was not expressed in the transplanted cells and not proliferated (FIG. 32).

Next, MEF (mouse embryo fibroblast) was induced to differentiate into mouse es/ENTER cells using a hES medium in the same manner as HDF. The MEF used in this experiment was OG2-MEF and was performed with an embryo fibroblast of mouse transfected with an Oct4 promoter vector. These cells express GFP fluorescence when Oct4 is expressed and were used to observe the expression of Oct4.

Figure 33:
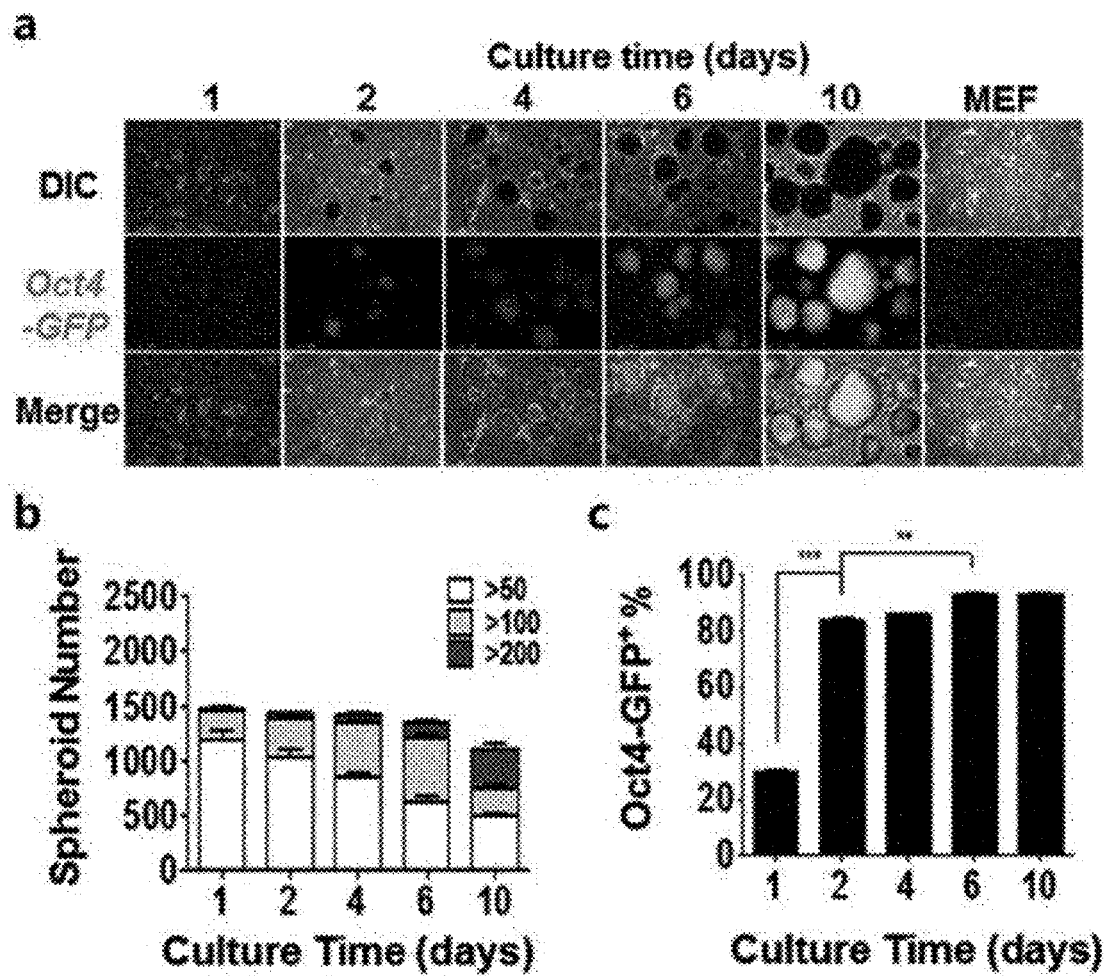
FIG. 33 shows results of differentiation of MEF into mouse es/ENTER cells by a human ES culture medium and ultrasonic wave stimulation, in which (A) shows changes in cell morphology and Oct4-GFP expressions according to a culture time, (B) shows a spheroid formation rate according to a culture time, and (C) shows a change of Oct4 expressions.

As shown in FIG. 33, the number and sizes of spheroids and GFP expression were increased over time in the cells induced by ultrasonic wave treatment.

Next, pluripotent properties were analyzed in the mouse es/ENTER cells.

Figure 34:
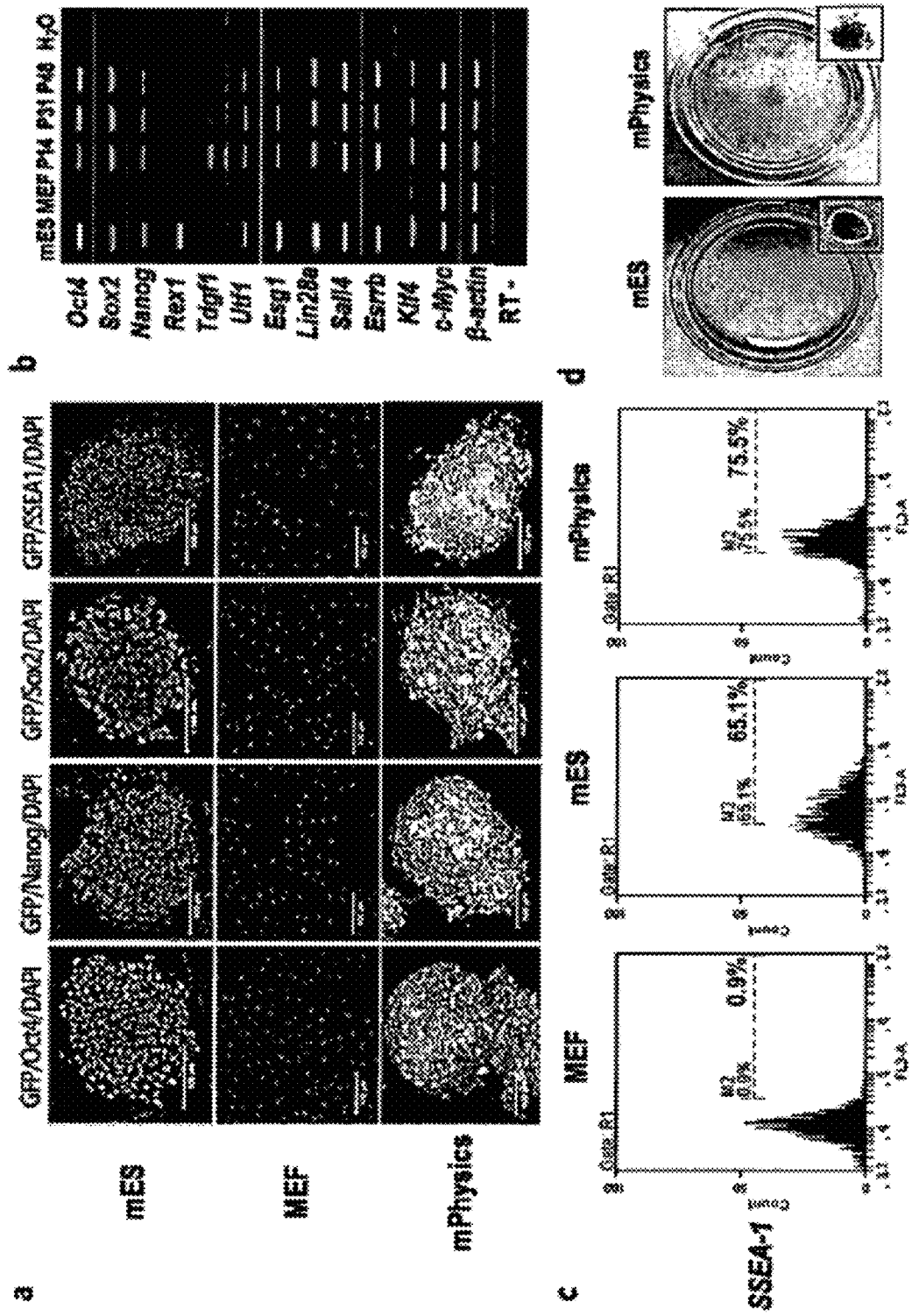
FIG. 34 shows results of analyzing pluripotent properties in mouse es/ENTER cells, in which (A) shows expressions of a pluripotent marker protein by immunocytochemistry, (B) shows expressions of a pluripotent marker gene by RT-PCR, (C) shows a result of analyzing an expression rate of a pluripotent marker gene by flow cytometry, and (D) shows a result of alkaline phosphatase (AP) staining of mouse es/ENTER cells.

As shown in FIG. 34, ICC, RT-PCR, flow cytometry, and AP staining of mouse es/ENTER showed similar tendency to mouse ES.

Next, triploblastic properties were analyzed in the mouse es/ENTER cells.

Figure 35:
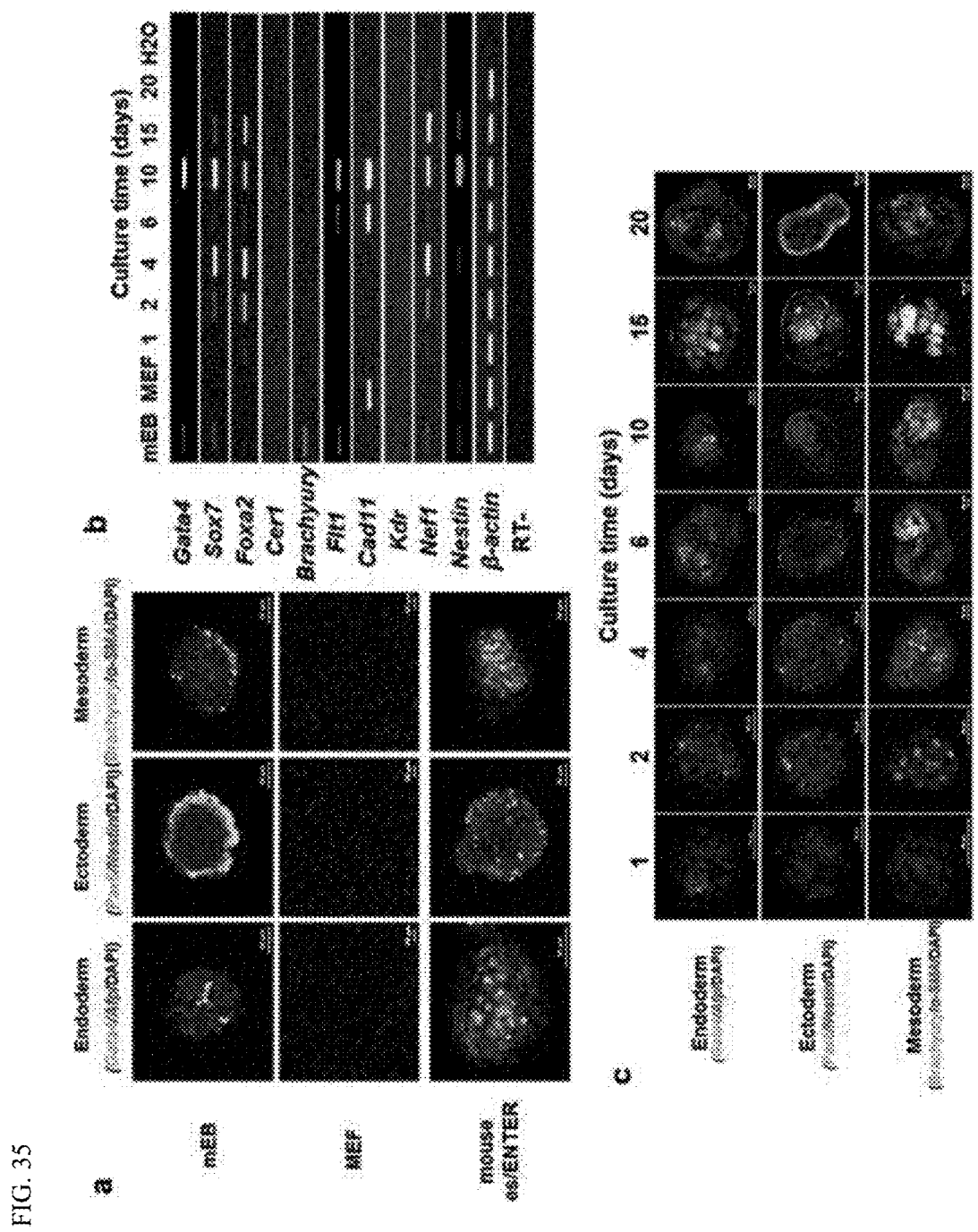
FIG. 35 shows results of analyzing triploblastic properties in mouse es/ENTER cells, in which (A) shows a result of analyzing expression of a triploblastic marker by immunocytochemistry, and (B) and (C) show results of analyzing expression patterns of (B) triploblastic marker gene and (C) protein for each culture time, respectively.

As a result, the triploblastic properties shown in the human es/ENTER were also observed even in the mouse es/ENTER cells, and a difference in expression was shown over time through RT-PCR and ICC analysis for each culture time. This result was the same as the result of human es/ENTER (FIG. 35).

Figure 36:
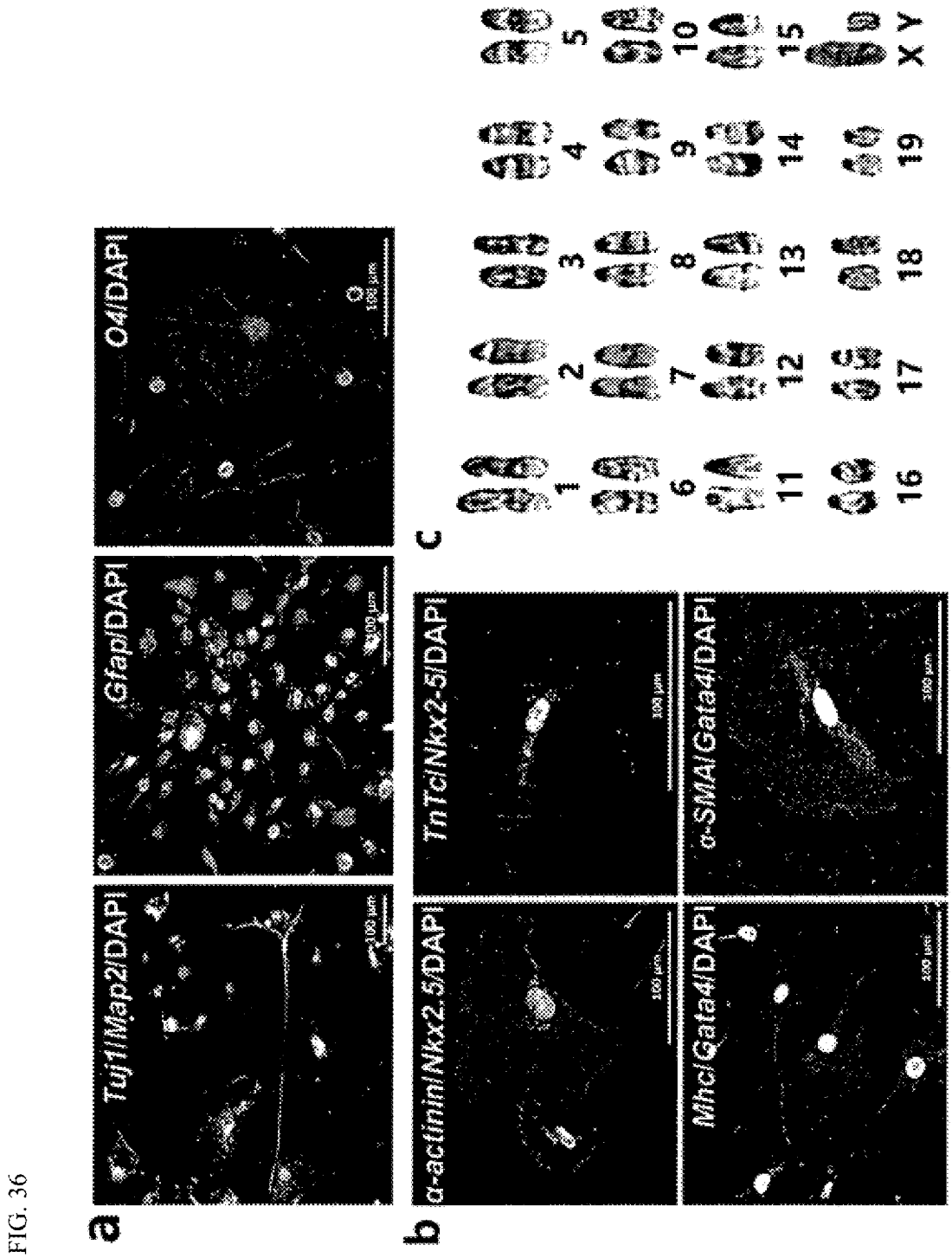
FIG. 36 shows results of in-vitro differentiation of mouse es/ENTER cells into (A) neurons and (B) cardiomyocytes and (C) a karyotype analysis result by chromosome G-band analysis of mouse es/ENTER cells.

FIG. 36 shows in-vitro differentiation of mouse es/ENTER into (A) neuron and (B) cardiomyocyte, and FIG. 36C shows a karyotype analysis result by chromosome G band analysis of mouse es/ENTER. The karyotype analysis was performed using a GTG banding chromosome analysis (GenDix, Inc. Seoul, Korea).

As an experimental result, the differentiation markers of neurons and cardiomyocytes were confirmed in mouse es/ENTER cells to be differentiated, and as a result of karyotype analysis of chromosomal mutations by ultrasonic waves, it was confirmed that there was no mutation.

<Example 10> Experiment for Differentiation Induction of Es/ENTER Using Other Cells These results show that this method is applicable to cells of other individuals as well as HDF, and applied to various cells (L132, MSC, patient skin fibroblasts).

Cell differentiation was induced in the same manner as es/ENTER using L132 (pulmonary epithelial cells), mesenchymal stem cells (MSCs), and skin fibroblasts (patient-derived skin fibroblasts), and as a result, it was shown that cell spheroids were formed, and the pluripotent markers and the triploblastic markers were expressed similar to es/ENTER.

Figure 37:
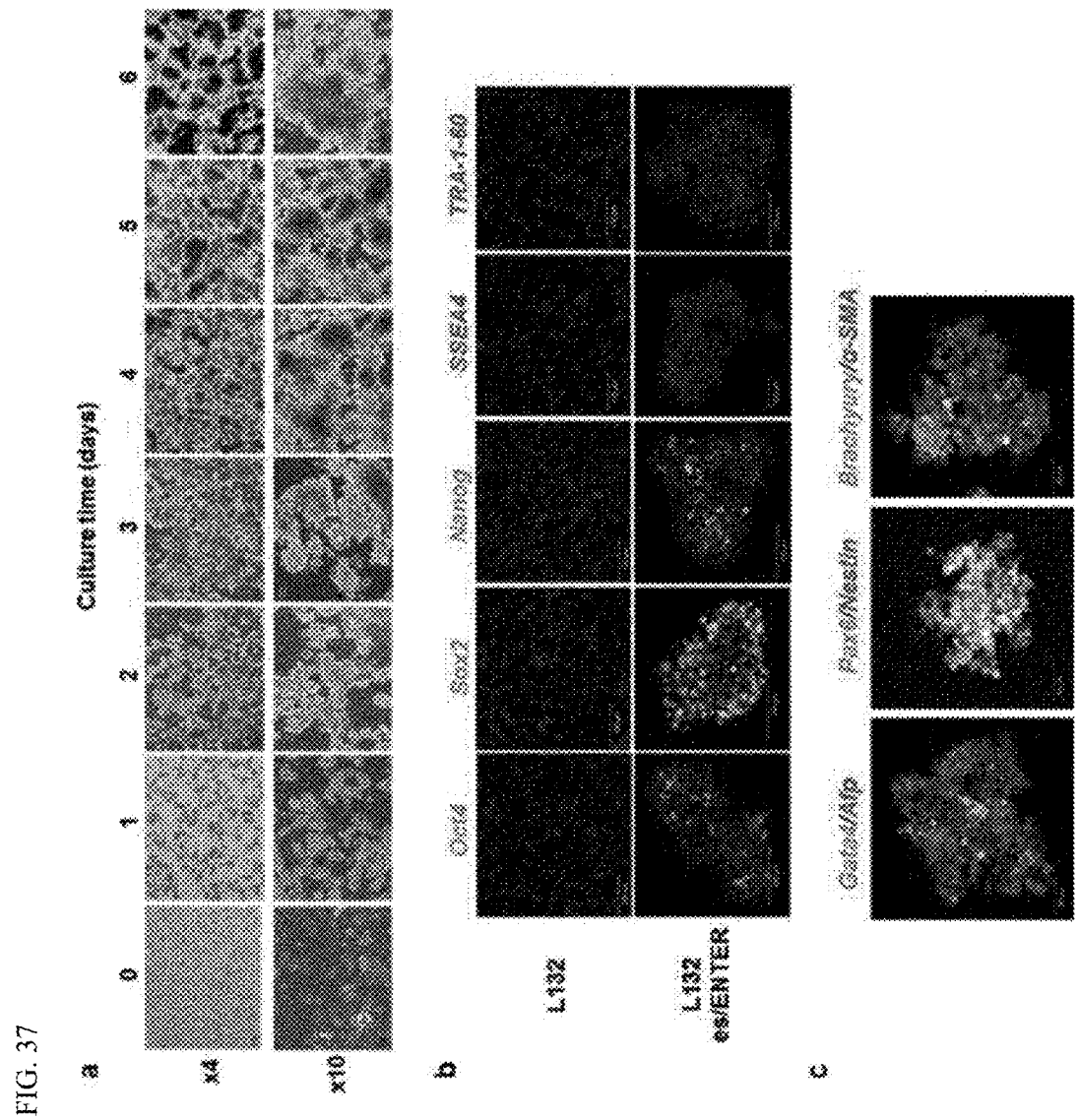
FIG. 37 shows results of differentiation of L132 cells into L132 es/ENTER cells by a human ES culture medium and ultrasonic wave stimulation, in which (A) shows a change in cell morphology according to a culture time, and (B) and (C) show changes in pluripotent (B) and triploblastic (C) properties of the L132 es/ENTER cells.

FIG. 37 shows a result of the differentiation of L132 cells into L132 es/ENTER cells by a human ES culture medium and ultrasonic wave stimulation, in which FIG. 37A shows a change in cell morphology according to a culture time, and FIGS. 37B and 37C show changes in (B) pluripotent and (C) triploblastic properties of the L132 es/ENTER cells.

Figure 38:
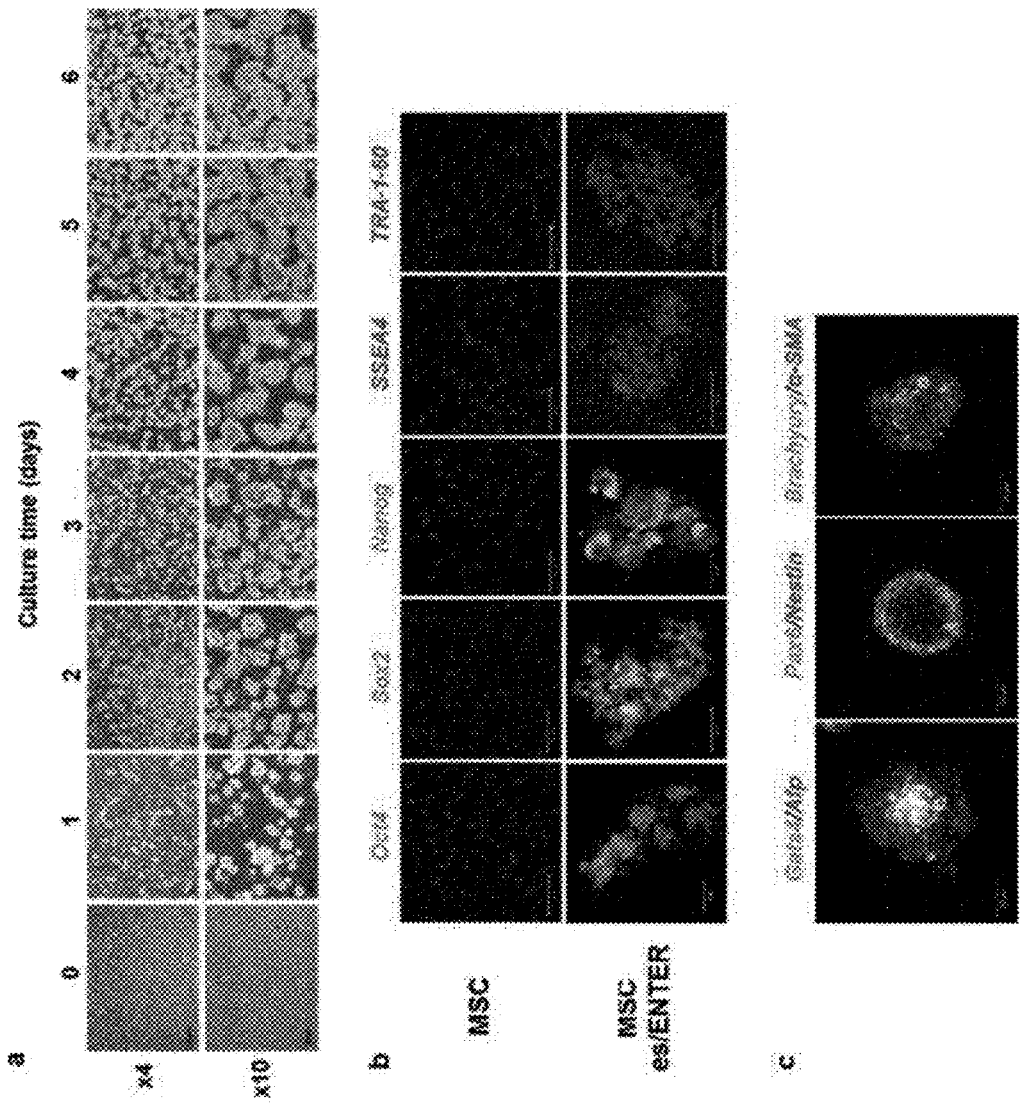
FIG. 38 shows results of differentiation of MSC into MSC es/ENTER cells by a human ES culture medium and ultrasonic wave stimulation, in which (A) shows a change in cell morphology according to a culture time, and (B) and (C) show changes in pluripotent (B) and triploblastic (C) properties of the MSC es/ENTER cells.

FIG. 38 shows a result of the differentiation of MSC into MSC es/ENTER cells by a human ES culture medium and ultrasonic wave stimulation, in which FIG. 38A shows a change in cell morphology according to a culture time, and FIGS. 38B and 38C show changes in (B) pluripotent and (C) triploblastic properties of the MSC es/ENTER cells.

Figure 39:
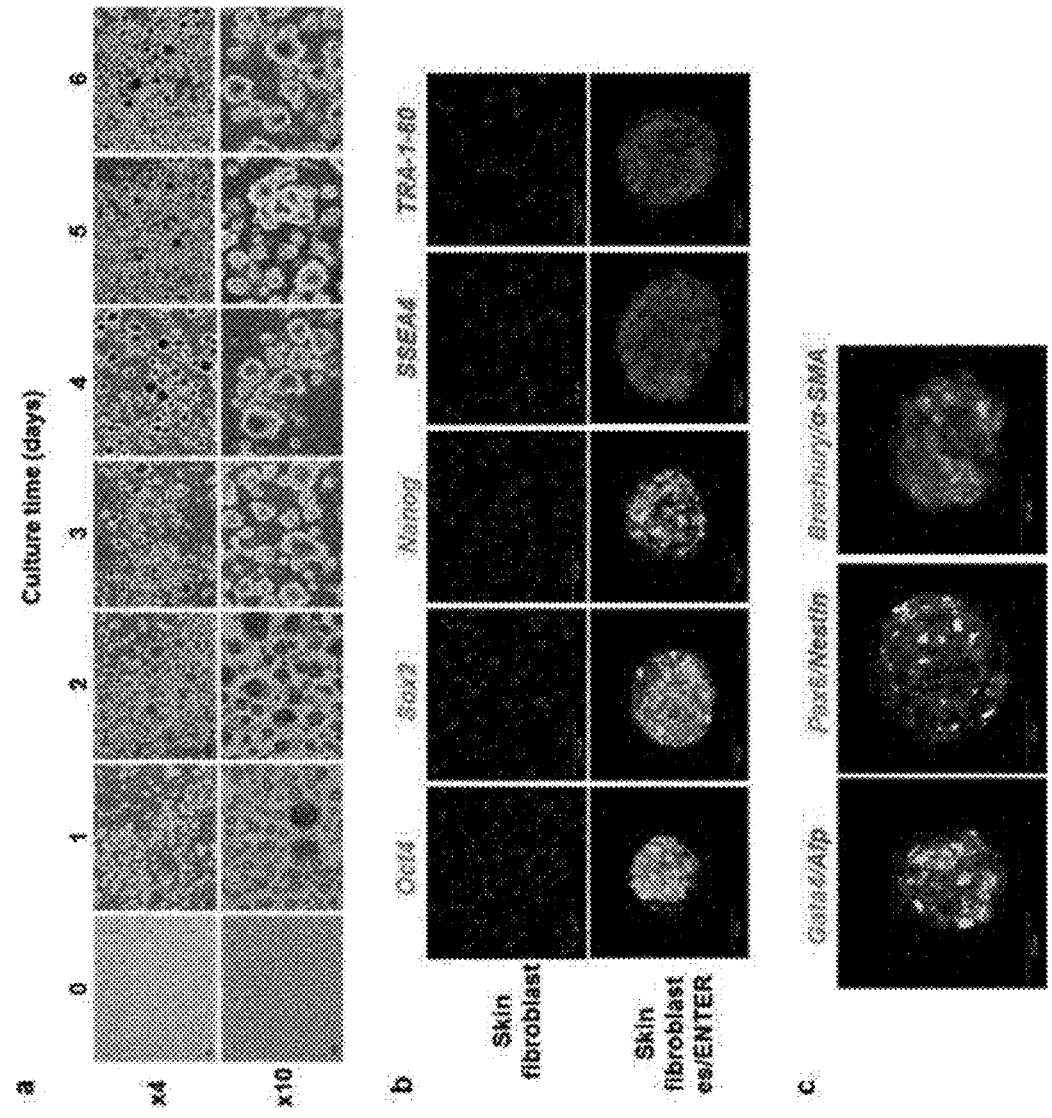
FIG. 39 shows results of differentiation of human skin fibroblasts into SF es/ENTER cells by a human ES culture medium and ultrasonic wave stimulation, in which (A) shows a change in cell morphology according to a culture time, and (B) and (C) show changes in (B) pluripotent and (C) triploblastic properties of the SF es/ENTER cells.

FIG. 39 shows a result of the differentiation of human skin fibroblasts into SF es/ENTER cells by a human ES culture medium and ultrasonic wave stimulation, in which FIG. 39A shows a change in cell morphology according to a culture time, and FIGS. 39B and 39C show changes in (B) pluripotent and (C) triploblastic properties of the SF es/ENTER cells.

<Example 11> Differentiation Induction into Es/ENTER Cells Using Other Physical Stimulation Heat shock and laser were used as physical stimulation for induction of differentiation into the same medium as the human ES medium.

First, differentiation of HDF into es/ENTER cells was induced by heat shock and a hES medium. For heat shock, HDF was exposed at 42° C. for 2 minutes and then left for about 5 seconds on ice. FIG. 40A shows differentiation-induced HDF spheroid, and FIGS. 40B and 40C show (B) pluripotent and (C) triploblastic properties of es/ENTER cells.

Next, differentiation of es/ENTER cells of HDF was induced by laser stimulation and a hES medium. As the laser treatment condition, an Ocla treatment laser (Ndlux) was used, and the cells were cultured after irradiating a laser at 808 nm for 5 seconds. FIG. 41A shows differentiation-induced HDF spheroid, and FIGS. 41B and 41C show (B) pluripotent and (C) triploblastic properties of es/ENTER cells.

Figure 40:
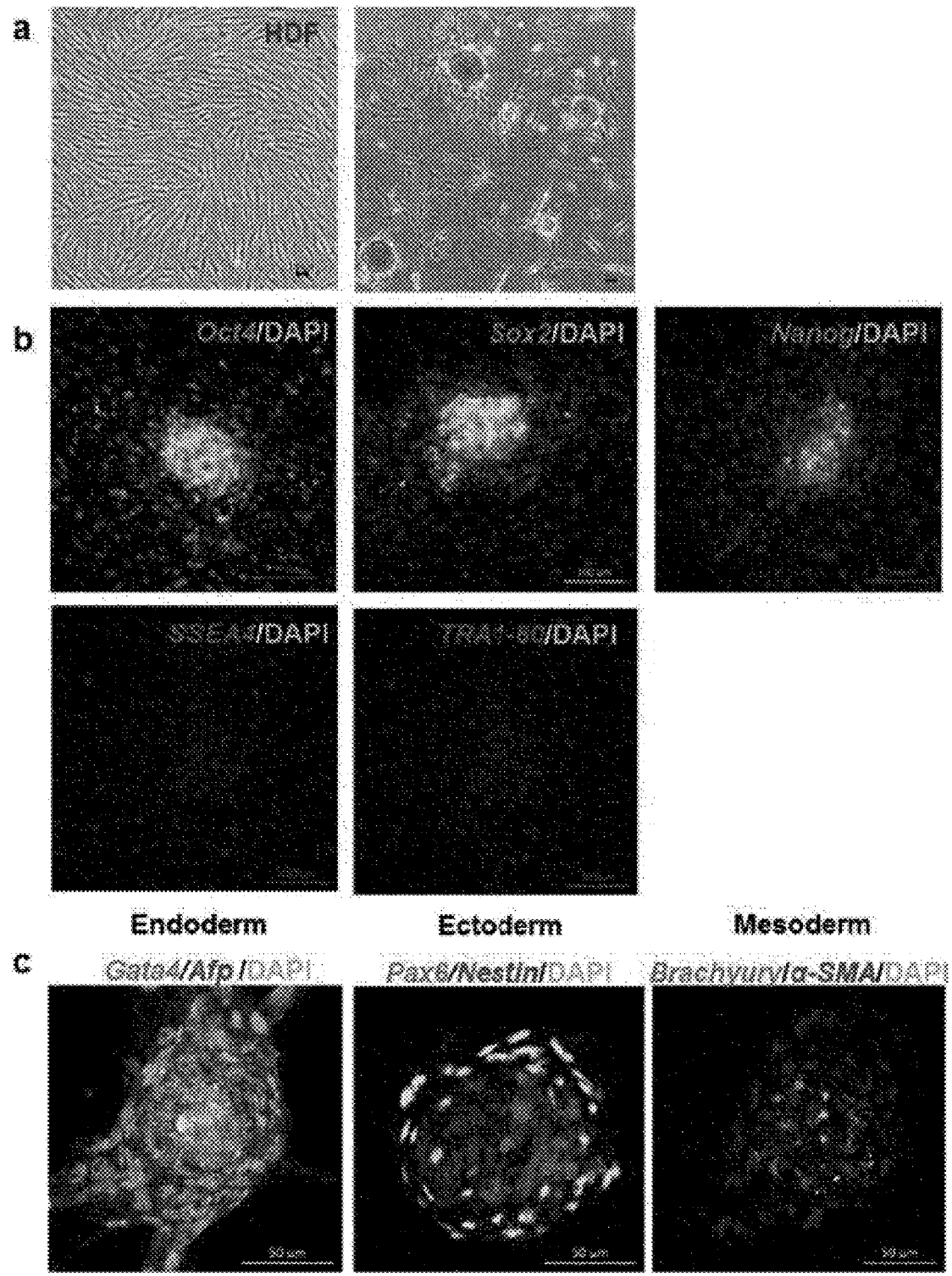
FIG. 40 shows results of differentiation into es/ENTER cells of HDF using heat shock and a hEs medium, in which (A) shows differentiation-induced HDF spheroid, and (B) and (C) show (B) pluripotent and (C) triploblastic properties of the es/ENTER cells.
Figure 41:
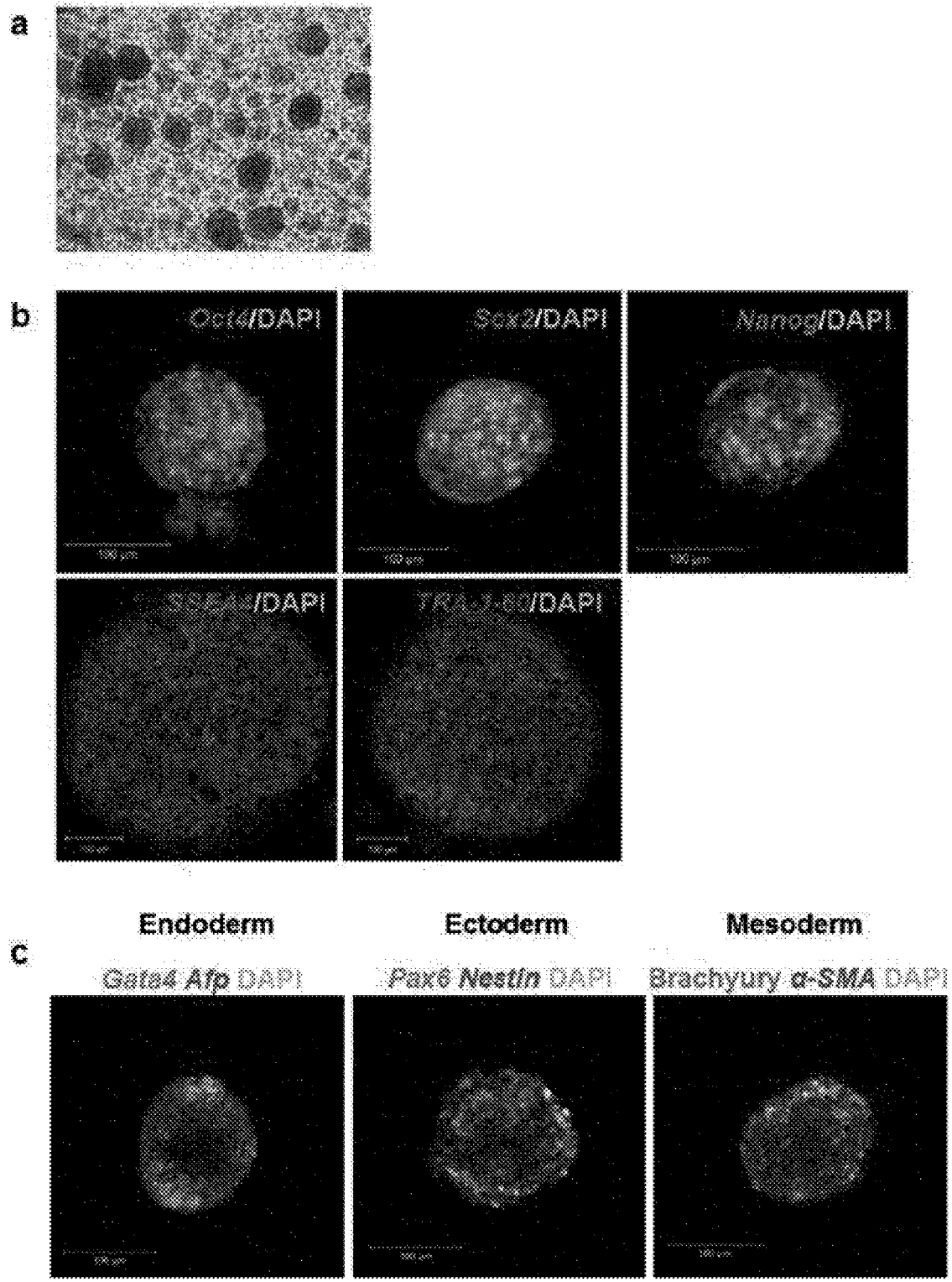
FIG. 41 shows results of differentiation into es/ENTER cells of HDF using laser stimulation and a hEs medium, in which (A) shows differentiation-induced HDF spheroid, and (B) and (C) show (B) pluripotent and (C) triploblastic properties of the es/ENTER cells.

As shown in FIGS. 40 and 41, it was confirmed that cell spheroids were formed by both stimulations similarly to the effects by ultrasonic waves, and the pluripotent and triploblastic markers were expressed. These results indicate that cell reprogramming due to a medium environmental influx is applicable to various cells and that various methods are possible as the physical stimulation for environmental influx with the medium environment, and like the previous result, the properties of the cells may be changed by the environment.

<Example 12> Reprogramming of Cells Using Extracellular Vesicles (EVs)

The cells, primary HDFs purchased from Invitrogen, were cultured in a DMEM added with 10% FBS (Gibco) and 1% penicillin/streptomycin (Gibco), ultrasonic wave treatment to the culture medium was performed at 5 W/cm$^2$, for 10 minutes, the cell treatment was performed in 1×10 6 HDFs at 1 W/cm$^2$ for 5 seconds, and then 2×10$^5$ cells were cultured in a 35 mm culture dish together with the ultrasonic wave-treated culture medium under conditions of 37° C. and 5% $CO_2$ for 1 day. The culture medium was recovered, put in an Amicon Ultra centrifugal filter (Millipore), and centrifuged at 14000 rpm for 20 minutes, and then the EVs in the culture medium were filtered and recovered by a filter.

Next, the HDF was cultured in a culture dish so as to be filled with about 70 to 80%, and the culture medium was recovered and washed twice with D-PBS. Thereafter, 10 µl/mL (v/v) of concentrated EVs recovered from the culture medium on day 1 of es/ENTER and n/ENTER were added to an embryonic stem cell medium or a neural stem cell differentiation medium (Gibco), mixed with the HDF washed above, and then cultured for 3 days.

<Example 13> Experiment of Delivery of EVs in Normal Somatic Cells (HDF)

In order to confirm reprogramming of somatic cells using EVs, EVs obtained after one day of culturing in cells subjected to physical stimulation as in Example 12 were concentrated, the EVs were labeled using Did dye, and the EVs was delivered to normal somatic cells, and the expression of Oct4, a pluripotent marker, and Pax6, a neural stem cell marker, was confirmed in the delivered cells.

Figure 42:
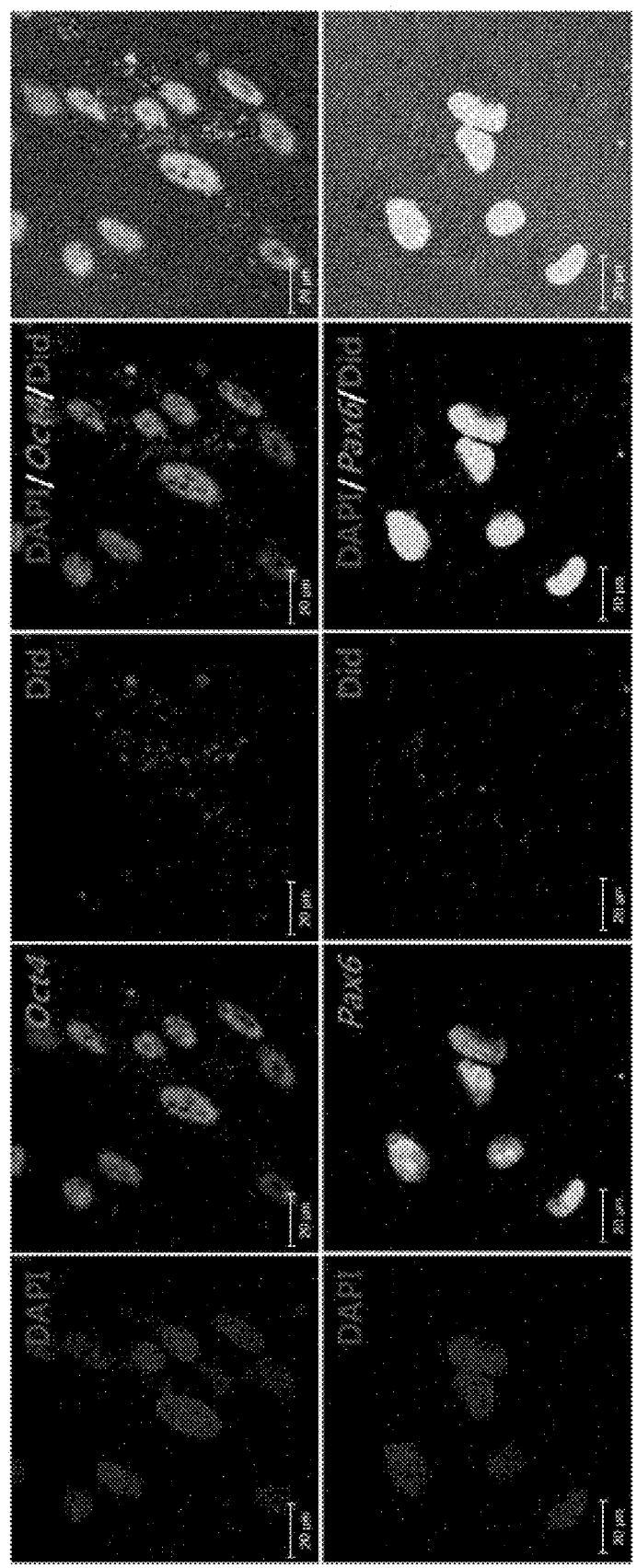
FIG. 42 shows a result of confirming whether or not extracellular vesicles (EVs) are delivered to normal somatic cells.

To this end, 50 µl of EVs obtained in Example 12 was mixed with 450 µl of D-PBS and diluted, and 2.5 µl of a Vybrant DiD cell-labelling solution (molecular probe, excitation/emission, 644/667 nm) was added thereto and exosomes were stained at 37° C. for 30 minutes. After staining, the Did-stained EVs were concentrated by centrifugation at 14,000 rpm for 20 minute by an Amicon Ultra centrifugal filter (Millipore), diluted with D-PBS twice, added to 3 mL of a HDF medium (DMEM (Gibco) culture medium containing 5% FBS), and then cultured at 37° C. and 5% $CO_2$ for 24 hours. The HDF cultured for 24 hours was immobilized with 4% paraformaldehyde for 10 minutes and permeabilized with a 0.2% triton X100 in PBS buffer for 10 minutes. Thereafter, the cells were blocked with 3% BSA in PBS buffer for 1 hour, stained overnight at 4° C. with primary antibodies, anti-rabbit Oct4 (1:250, abeam) and Pax6 (1:200, abeam), and then stained with a secondary antibody, an anti-rabbit conjugated Alexa-488 (1:1000, Thermo, excitation/emission, 495/519 nm) for 1 hour. The images of samples stained with secondary antibodies were analyzed by a confocal laser scanning microscope (LSM 700; Carl Zeiss) using a mounting solution containing DAPI (4',6-diamidino-2-phenylindole dihydrochloride, Vector Laboratories, excitation/emission, 420/480 nm), and the results are shown in FIG. 42. In the drawing, green is Oct4, and red is EVs stained with Did dye.

As shown in FIG. 42, it was confirmed that EVs secreted from cells after physical stimulation include genes and proteins of various pluripotent markers according to a cell culture medium environment, and these factors may be delivered to adjacent cells by the EVs. These results suggest that EVs secreted from cells subjected to the physical stimulation in various medium conditions have a possibility to induce reprogramming of normal somatic cells.

<Example 14> Reprogramming Effect of Human Fibroblasts by EVs

Since the EVs secreted from the cells subjected to the physical stimulation in various media environments in Example 13 above have a possibility to induce reprogramming of normal somatic cells, in order to verify the possibility, the experiment was performed using a DMEM medium, which is a human fibroblast culture medium, and a hESC medium, which is a culture medium of human embryonic stem cells or iPS cells. A control group was cultured for 3 days in each medium without adding EVs, and a treated group was cultured for 3 days by adding 10 µl/mL (v/v) of EVs.

Figure 43:
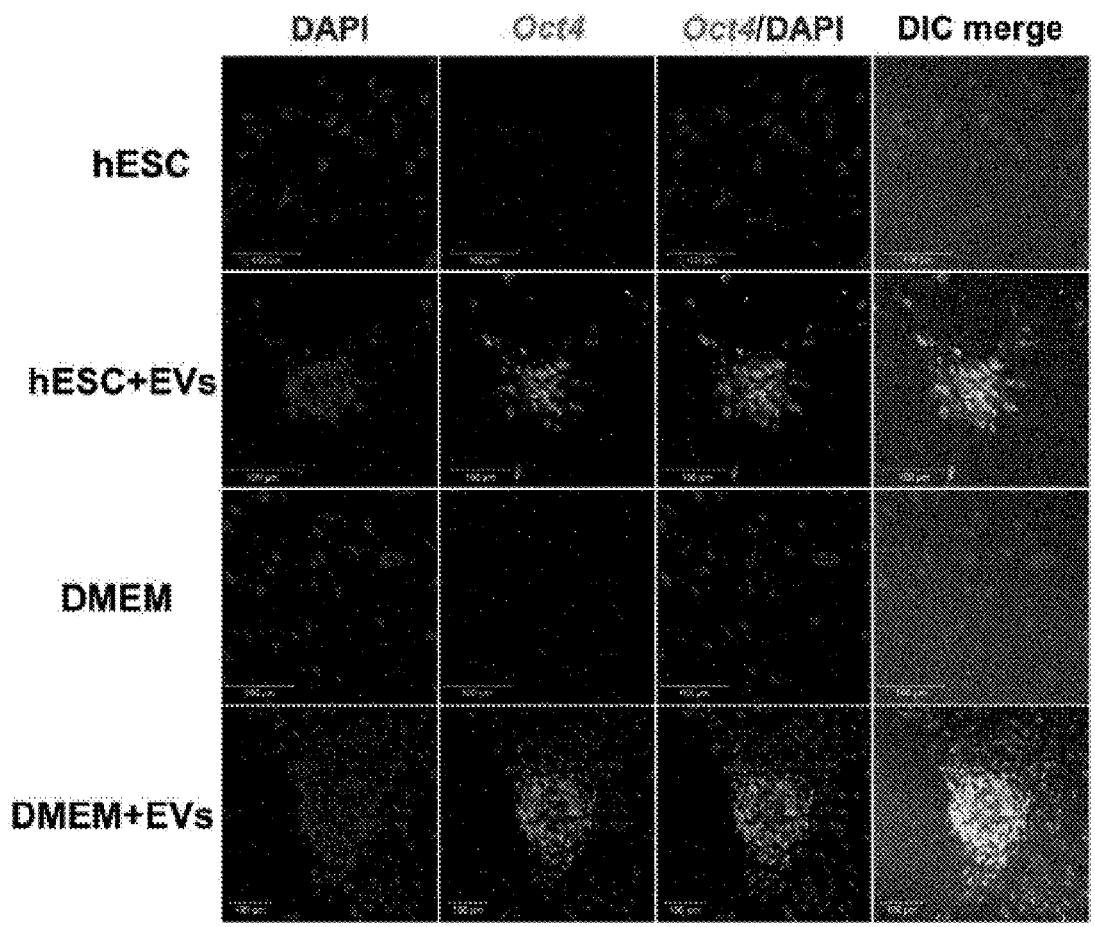
FIG. 43 shows a result of confirming reprogramming induction of human fibroblasts by EVs.

The cultured cells were stained with a primary antibody, rabbit-anti-Oct4 (1:250, abeam) and a secondary antibody, anti-rabbit conjugated Alexa-488 (1:1000, Thermo excitation/emission, 495/519 nm), mounted with a mounting solution containing DAPI, then images were analyzed with a confocal laser microscope, and the results are shown in FIG. 43. In FIG. 43, hESC indicates a human ESC medium, DMEM indicates a fibroblast culture medium, and EVs indicates EVs recovered upon es/ENTER induction.

As shown in FIG. 43, the expression of Oct4 was not observed in the control group, but the expression of Oct4 and the formation of spheroid from the cells were observed in the treated group. These results indicate that cell reprogramming was induced only by EVs, not by culture medium.

<Example 15> Change in Cell Morphology of EVs-Treated Human Fibroblasts for Each Culture Time Human fibroblasts were treated with 10 µl/mL (v/v) of EVs recovered during es/ENTER induction and cultured for 6 days, and then changes in morphology of cells were observed.

Figure 44:
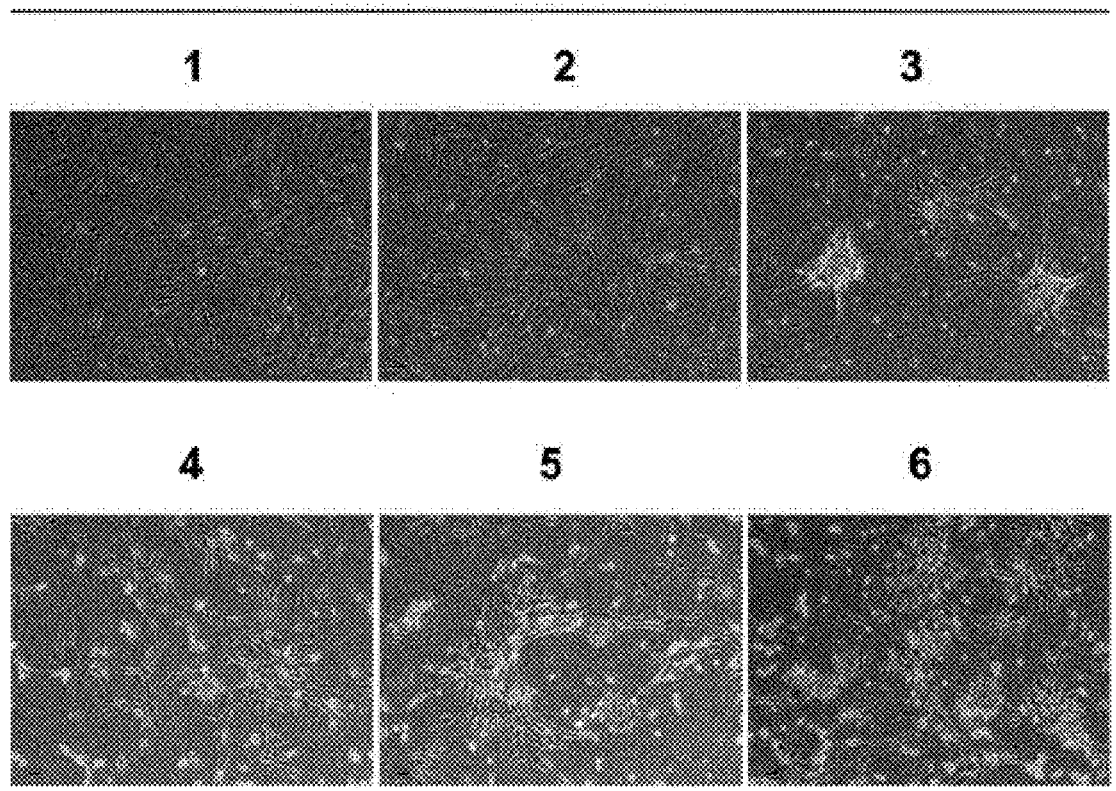
FIG. 44 shows changes in cell morphology of the EV-treated human fibroblasts recovered upon es/ENTER induction for each culture time.

As shown in FIG. 44, the morphology of the cells varied according to a culture time, and the formation of spheroid was observed on day 3.

<Example 16> Experiment for Verifying Expression of Pluripotent Marker of HDF Cultured for 6 Days According to EV-Adding Amount Recovered During Es/ENTER Induction To determine an appropriate concentration of EVs for cell reprogramming, the cells were treated with HDF and cultured for 6 days by varying the adding amount of EVs. In addition, since the EVs recovered during es/ENTER induction are used, cells expressing the pluripotent marker Oct4 were analyzed by flow cytometry.

To this end, the EVs recovered during es/ENTER induction were added during fibroblast culturing at concentrations of 0, 5, 12.5, 25, 50, and 100 µl/mL (v/v) and cultured under conditions of 37° C. and 5% $CO_2$ for 6 days. The cultured cells were stained with a primary antibody, rabbit-anti-Oct4 (1:250, abeam) and a secondary antibody, anti-rabbit conjugated Alexa-488 (1:1000, Thermo excitation/emission, 495/519 nm) like Example 13 and analyzed with a BD Accuri™ C6 flow cytometry (BD biosciences).

Figure 45:
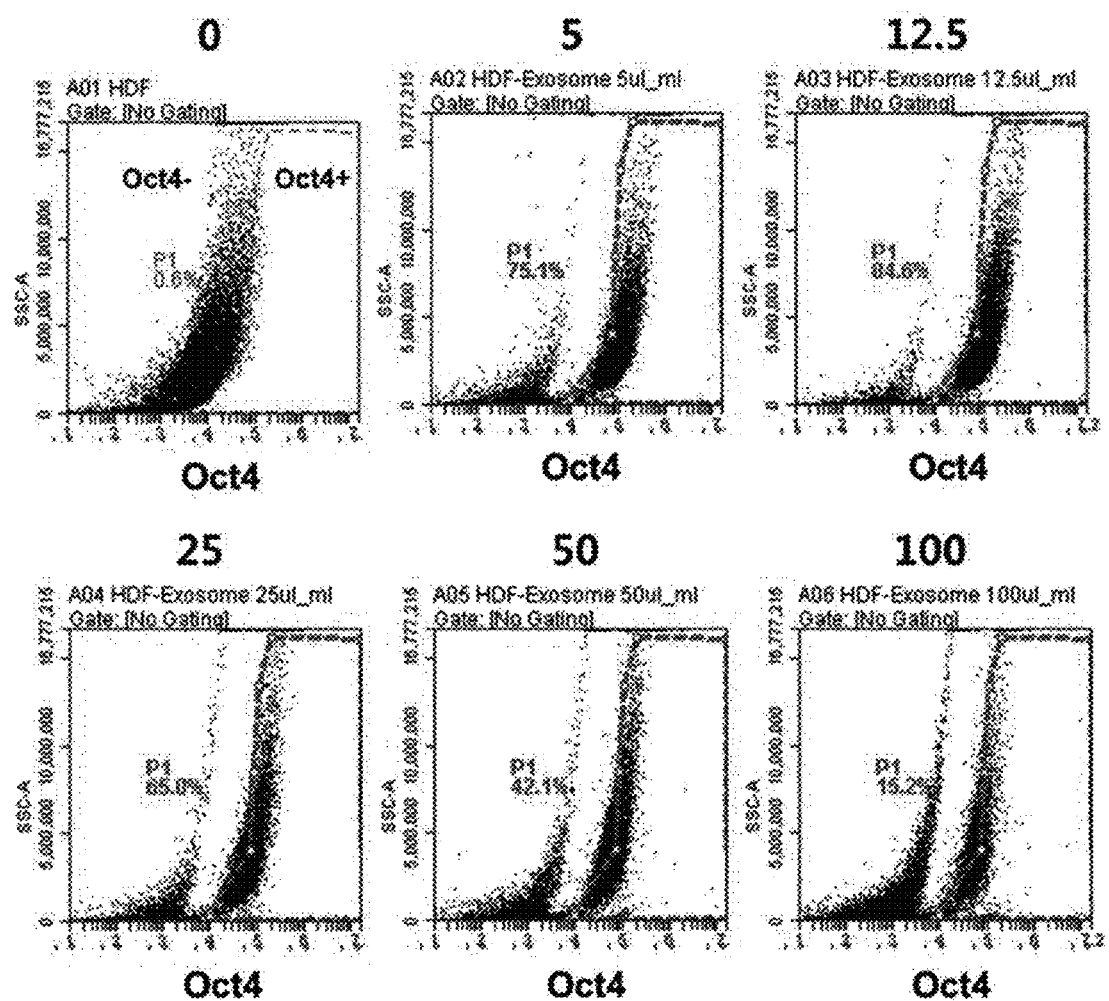
FIG. 45 shows a flow cytometry analysis result of confirming expression of Oct4 in HDF cultured for 6 days according to an EV-adding amount.

As shown in FIG. 45, when the EVs of 12.5 µl/mL (v/v) were treated, the expression of Oct4 was confirmed in 84.6% of the cells, which was the most.

<Example 17> Experiment for Verifying Expression of Pluripotent Marker of HDF Treated with EVs Recovered During Es/ENTER Induction Cultured for 3 Days Human fibroblasts were treated with 10 µl/mL (v/v) of EVs recovered during es/ENTER induction and cultured for 3 days, and a cell reprogramming effect was confirmed. For ICC analysis, like Example 13, the cultured cells used rabbit-anti-Oct4 (1:250, abeam), Sox2 (1:250, abeam), and Nanog (1:250, abeam) as primary antibodies and anti-rabbit conjugated Alexa-488 (1:1000, Thermo excitation/emission, 495/519 nm) as a secondary antibody, mounted with a mounting solution containing DAPI, and then images were analyzed with a confocal laser microscope. For qPCR analysis, total RNA was recovered using Trizol (Takara) in cells cultured for 3 days, and then cDNA was synthesized with Superscrip 2 kit (Invitrogen). PCR analysis was performed with real time PCR instrument (ab step one plus, AB) with respect to the pluripotent markers Oct4, Sox2, and Nanog.

Figure 46:
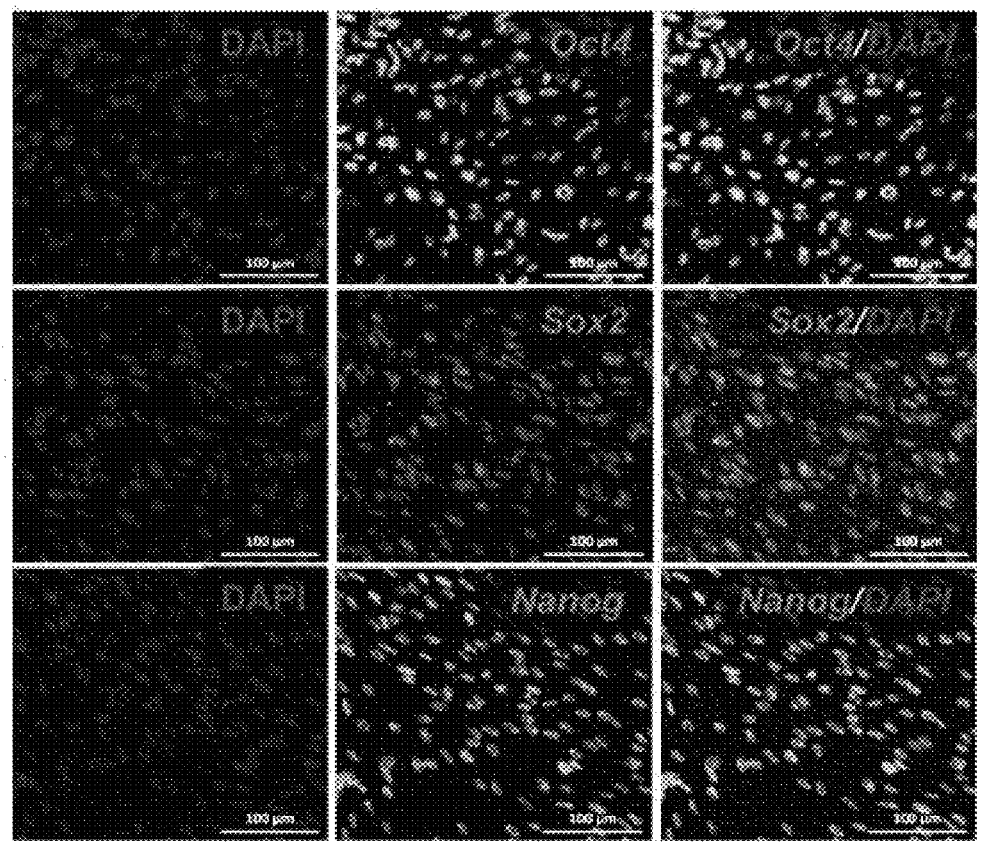
FIG. 46 shows results of confirming expression of a pluripotent marker protein (A: ICC image) and gene (B: qPCR assay) in EV-treated HDF cultured for 3 days recovered in es/ENTER induction.
Figure 46:
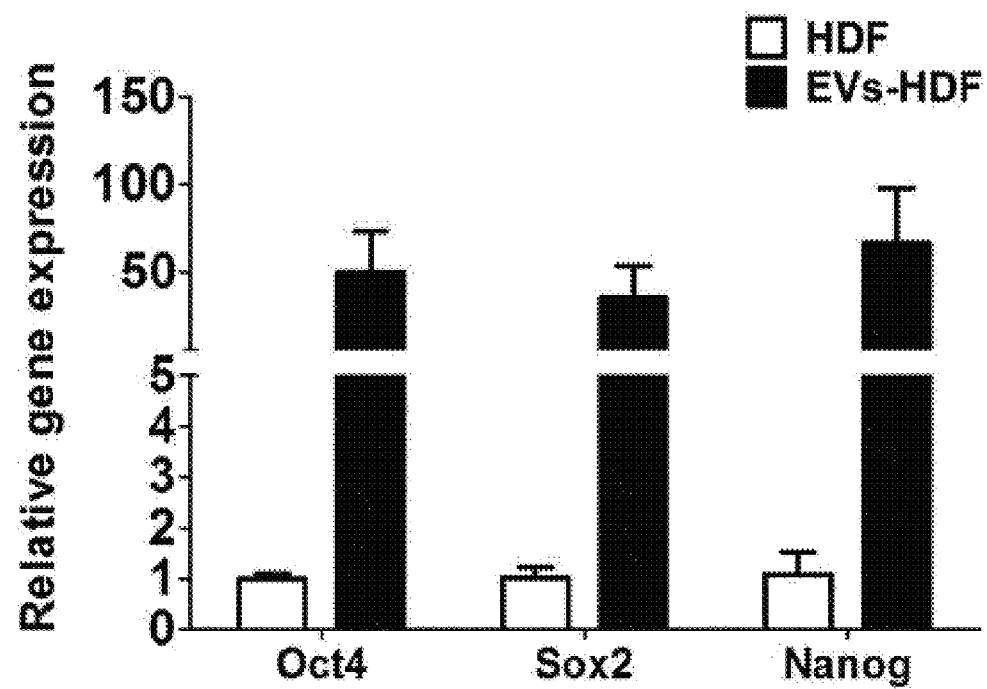

As shown in FIG. 46, the ICC analysis result shows that the expression of the pluripotent markers Oct4, Sox2 and Nanog was observed in the human fibroblast nucleus, and the qPCR analysis result of gene expression by real time PCR shows that the genes Oct4, Sox2 and Nanog were overexpressed by about 50 times as much as normal fibroblasts which were not treated with EVs.

<Example 18> Experiment for Verifying Expression of Neural Stem Cell Marker of HDF Treated with EVs Recovered During n/ENTER Induction and Cultured for 3 Days Human fibroblasts were treated with 10 µl/mL (v/v) of EVs recovered upon n/ENTER induction and cultured for 3 days, and a cell reprogramming effect was confirmed. For ICC analysis, like Example 13 above, the cultured cells used rabbit-anti-Sox1 (1:200, abeam), Sox2 (1:250, abeam), Pax6 (1:200, abeam), and mouse-anti-Nestin (1:250, Thermo Scientific) as primary antibodies and anti-rabbit conjugated Alexa-488 (1:1000, Thermo excitation/emission, 495/519 nm) and anti-mouse conjugated Alexa-594 (1:1000, Thermo, alexa 488 excitation/emission, 495/519 nm; alexa 594 excitation/emission, 590/617 nm) as secondary antibodies, mounted with a mounting solution containing DAPI, and then images were analyzed with a confocal laser microscope. For qPCR analysis, total RNA was recovered using Trizol (Takara) in cells cultured for 3 days, and then cDNA was synthesized with Superscrip 2 kit (Invitrogen). PCR analysis was performed with real time PCR instrument (ab step one plus, AB) with respect to the neural stem cell markers Sox1, Sox2, Pax6 and Nestin.

Figure 47:
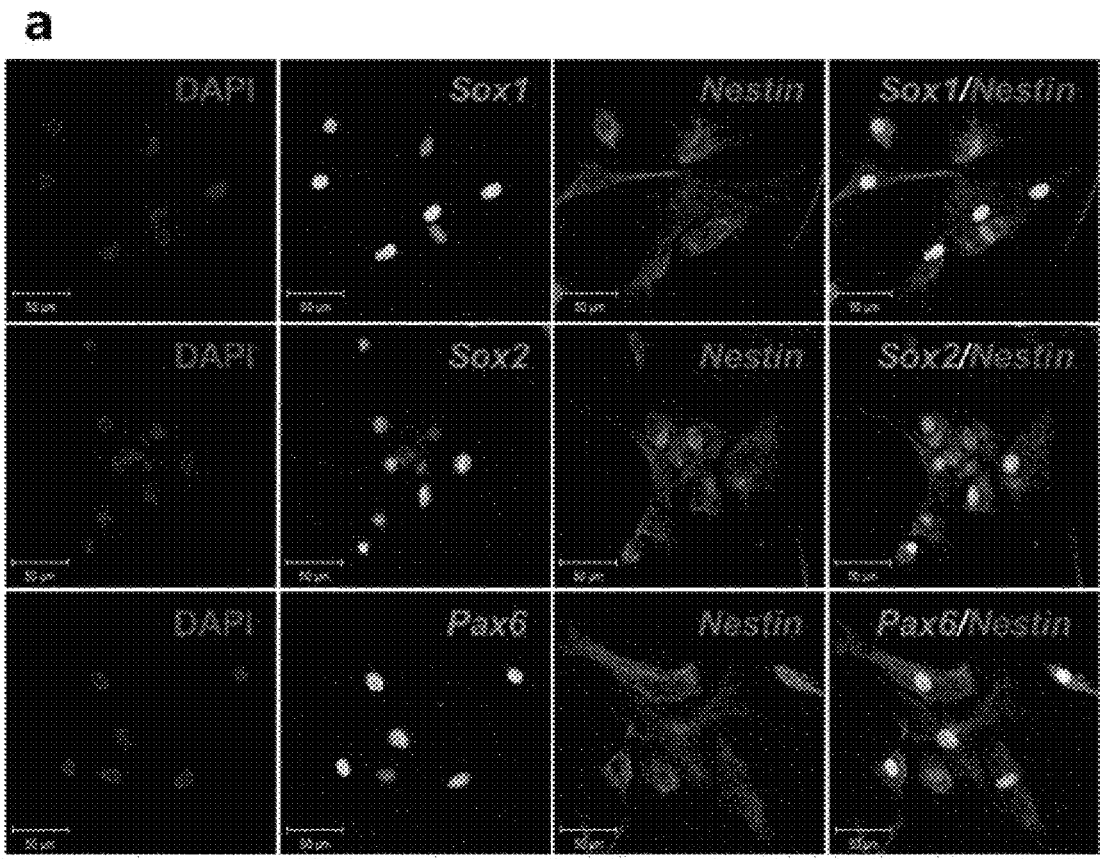
FIG. 47 shows results of confirming expression of a neural stem cell marker protein (A: ICC image) and gene (B: qPCR assay) in EV-treated HDF cultured for 3 days recovered in n/ENTER induction.
Figure 47:
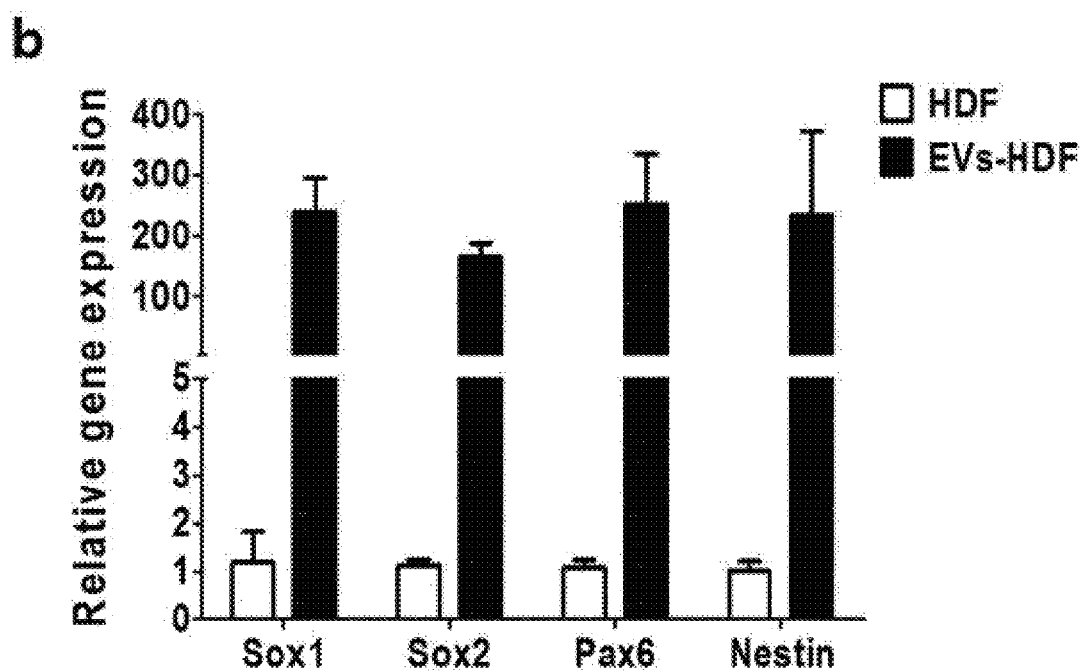

As shown in FIG. 47, the expression of the neural stem cell markers Sox1, Sox2, and Pax6 was observed in the human fibroblast nucleus, and the expression of Nestin was observed in the cytoplasm through ICC analysis. As the qPCR analysis result of gene expression by real time PCR, Sox1, Sox2, Pax6 and Nestin genes were overexpressed about 200 times as compared to normal fibroblasts which were not treated with EVs.

TABLE 6 qPCR primer list

| Gene code | | Primer sequence (5'-3') | |
|---|---|---|---|
| | | Forward | Backward |
| Pluripotent marker | Oct4 | GGGTTTTTGGGATTAAGTTCTTCA (SEQ ID NO: 57) | GCCCCCACCCTTTGTGTT (SEQ ID NO: 121) |
| | Sox2 | CAAAAATGGCCATGCAGGTT (SEQ ID NO: 58) | AGTTGGGATCGAACAAAAGCTATT (SEQ ID NO: 122) |
| | Nanog | ACAACTGGCCGAAGAATAGCA (SEQ ID NO: 59) | GGTTCCCAGTCGGGTTCAC (SEQ ID NO: 123) |
| Neural stem cell marker | Sox1 | TCTGTTAACTCACCGGGACC (SEQ ID NO: 60) | ACTCCAGGGTACACACAGGG (SEQ ID NO: 124) |
| | Sox2 | GGAGTGCAATAGGGCGGAAT (SEQ ID NO: 61) | CCAGTTGTAGACACGCACCT (SEQ ID NO: 125) |
| | Pax6 | GTCCATCTTTGCTTGGGAAA (SEQ ID NO: 62) | TAGCCAGGTTGCGAAGAACT (SEQ ID NO: 126) |
| | Nestin | CTCCAGAAACTCAAGCACC (SEQ ID NO: 63) | TCCTGATTCTCCTCTTCCA (SEQ ID NO: 127) |
| Gapdh | | ATGGGGAAGGTGAAGGTCG (SEQ ID NO: 64) | ATGGGGAAGGTGAAGGTCG (SEQ ID NO: 128) |

INDUSTRIAL APPLICABILITY

The present invention can be used for a cell therapeutic agent field.

The invention claimed is:

1. A cell reprogramming method comprising:
subjecting a mixture of human dermal fibroblasts (HDF) and a culture medium to ultrasonic waves treatment having an output intensity of 0.5 W/cm$^2$ to 3 W/cm$^2$ for 1 to 5 seconds which promote an environmental influx for a cell reprogramming, wherein the ultrasonic waves treatment induces damage of the cell membrane which is recovered 2 hours after being subjected to the ultrasonic waves treatment; and
culturing, immediately after the ultrasonic waves treatment, the mixture subjected to the ultrasonic waves treatment for a predetermined time to obtain reprogrammed cells,
wherein the culture medium is any one of a hepatocyte differentiation-inducing medium, an adipocyte differentiation-inducing medium, or a neuronal cell differentiation-inducing medium,
wherein the ultrasonic treatment promotes the environmental influx without introduction of a reprogramming inducing factor other than any one of the differentiation-inducing medium,
wherein the reprogrammed cells are any one of neurons expressing any one of PAX6, Nestin, Sox1, Sox2, MAP2, TuJ1, GFAP or O4; hepatocytes expressing any one of AFP, HNF1a, HNF4a, CK18 or ALB; or adipocytes stained with oil red O and expressing any one of Pparc2, C/ebpa, aP2 or Fabp4.

2. The cell reprogramming method of claim 1, wherein the environmental influx includes an intracellular influx of genetic materials, chemicals, small molecules, exosomes, or extracellular vesicles containing exosomes released from differentiated or non-differentiated cells subjected to the ultrasonic waves treatment; or culture medium components.

3. The cell reprogramming method of claim 1, further comprising:
  subjecting the culture medium to the ultrasonic waves treatment having an output intensity of 1 $W/cm^2$ to 20 $W/cm^2$ for 1 to 20 minutes before mixing the HDF with the culture medium.

4. The cell reprogramming method of claim 1, wherein the mixture subjected to the ultrasonic waves treatment is cultured for 1 to 20 days by a suspended culture or monolayer culture method.

\* \* \* \* \*